US012590315B2

(12) United States Patent (10) Patent No.: US 12,590,315 B2
Qi et al. (45) Date of Patent: Mar. 31, 2026

(54) **COMPOSITIONS AND METHODS BASED ON *QPT* ENGINEERING FOR PRODUCING TOBACCO PLANTS AND PRODUCTS HAVING ALTERED ALKALOID LEVELS**

(71) Applicant: Altria Client Services LLC, Richmond, VA (US)

(72) Inventors: Dong Qi, Henrico, VA (US); Chengalrayan Kudithipudi, Midlothian, VA (US); Yanxin Shen, Henrico, VA (US)

(73) Assignee: Altria Client Services LLC, Richmond, VA (US)

( * ) Notice: Subject to any disclaimer, the term of this patent is extended or adjusted under 35 U.S.C. 154(b) by 765 days.

(21) Appl. No.: 17/767,692

(22) PCT Filed: Oct. 9, 2020

(86) PCT No.: PCT/US2020/055105
§ 371 (c)(1),
(2) Date: Apr. 8, 2022

(87) PCT Pub. No.: WO2021/072288
PCT Pub. Date: Apr. 15, 2021

(65) Prior Publication Data
US 2023/0399651 A1 Dec. 14, 2023

Related U.S. Application Data

(60) Provisional application No. 62/913,357, filed on Oct. 10, 2019.

(51) Int. Cl.
*C12N 15/82* (2006.01)
*A24B 13/00* (2006.01)
*A24B 15/12* (2006.01)

(52) U.S. Cl.
CPC .......... *C12N 15/8243* (2013.01); *A24B 13/00* (2013.01); *A24B 15/12* (2013.01)

(58) Field of Classification Search
None
See application file for complete search history.

(56) References Cited

U.S. PATENT DOCUMENTS 4,516,590 A 5/1985 Teng
4,528,993 A 7/1985 Sensabaugh
(Continued)

FOREIGN PATENT DOCUMENTS

CN 1257542 A 6/2000
CN 1638655 A 7/2005
(Continued)

OTHER PUBLICATIONS

Sequence published as UniProtKB Accession No. A0A1S4DFD3 (version 10 dated Jul. 31, 2019; 1 total page). (Year: 2019).*
(Continued)

*Primary Examiner* — Matthew R Keogh
*Assistant Examiner* — Rebecca Stephens
(74) *Attorney, Agent, or Firm* — Arnold & Porter Kaye Scholer LLP; David R. Marsh

(57) ABSTRACT

The present disclosure provides compositions and methods related to tobacco plants with altered total alkaloid and nicotine levels and commercially acceptable leaf grade, their development via breeding or transgenic approaches, and production of tobacco products from these tobacco plants.

19 Claims, 3 Drawing Sheets
Specification includes a Sequence Listing.

(56) References Cited

U.S. PATENT DOCUMENTS

| | | | |
|---|---|---|---|
| 4,660,577 A | 4/1987 | Sensabaugh et al. | |
| 4,732,856 A | 3/1988 | Federoff | |
| 4,848,373 A | 7/1989 | Lenkey | |
| 4,987,907 A | 1/1991 | Townend | |
| 5,013,658 A | 5/1991 | Dooner et al. | |
| 5,149,645 A | 9/1992 | Hoekema et al. | |
| 5,372,149 A | 12/1994 | Roth et al. | |
| 5,491,081 A | 2/1996 | Webb | |
| 5,689,035 A | 11/1997 | Webb | |
| 6,586,661 B1 * | 7/2003 | Conkling | C12N 15/8243 800/278 |
| 8,124,851 B2 | 2/2012 | Dewey et al. | |
| 8,319,011 B2 | 11/2012 | Xu et al. | |
| 9,187,759 B2 | 11/2015 | Dewey et al. | |
| 9,228,194 B2 | 1/2016 | Dewey et al. | |
| 9,228,195 B2 | 1/2016 | Dewey et al. | |
| 9,247,706 B2 | 2/2016 | Dewey et al. | |
| 2004/0118422 A1 | 6/2004 | Lundin et al. | |
| 2005/0178398 A1 | 8/2005 | Breslin et al. | |
| 2006/0157072 A1 | 7/2006 | Albino et al. | |
| 2006/0191548 A1 | 8/2006 | Strickland et al. | |
| 2007/0240728 A1 | 10/2007 | Hashimoto et al. | |
| 2008/0120737 A1 | 5/2008 | Hashimoto et al. | |
| 2010/0273171 A1 | 10/2010 | Jorgensen et al. | |
| 2011/0173721 A1 * | 7/2011 | Albino | A24B 13/00 536/23.6 |
| 2014/0283165 A1 | 9/2014 | Kudithipudi et al. | |
| 2016/0010103 A1 | 1/2016 | Kudithipudi et al. | |
| 2016/0374387 A1 * | 12/2016 | Adams | C12N 15/8218 131/336 |
| 2017/0233756 A1 | 8/2017 | Begemann et al. | |
| 2018/0119163 A1 | 5/2018 | Kudithipudi et al. | |
| 2024/0229053 A1 * | 7/2024 | Seo | C12N 9/1077 |

FOREIGN PATENT DOCUMENTS

| | | | | |
|---|---|---|---|---|
| CN | 1812811 A | 8/2006 | | |
| CN | 101155920 A | 4/2008 | | |
| CN | 106381327 A | 2/2017 | | |
| CN | 108271341 A | 7/2018 | | |
| WO | WO 98/56923 A1 | 12/1998 | | |
| WO | WO 02/100199 A2 | 12/2002 | | |
| WO | WO 2004/041006 A1 | 5/2004 | | |
| WO | WO 2005/000352 A1 | 1/2005 | | |
| WO | WO 2007/064636 A1 | 6/2006 | | |
| WO | WO 2007/072224 A2 | 6/2007 | | |
| WO | WO 2011/027315 A1 | 3/2011 | | |
| WO | WO 2018/067985 A1 | 4/2018 | | |
| WO | WO 2018/237107 A1 | 12/2018 | | |
| WO | WO-2018222667 A1 * | 12/2018 | | C12N 15/11 |
| WO | WO 2019/140297 A1 | 7/2019 | | |

OTHER PUBLICATIONS

Sequence published as UniProtKB Accession No. A0A1S4CL59 (version 10 dated Jul. 31, 2019; 1 total page) (Year: 2019).*

Ryan et al. (2012 "Structure and expression of the quinolinate phosphoribosyltransferase (QPT) gene family in Nicotiana" Plant Science 188(189):102-110). (Year: 2012).*

Kajikawa et al. 2017 ("Genomic Insights into the Evolution of the Nicotine Biosynthesis Pathway in Tobacco" Plant Physiology 174: 999-1011). (Year: 2017).*

Xia & Fan (2016 "Nicotine biosynthesis is regulated by two more layers: Small and long non-protein-coding RNAs" Plant Signaling & Behavior 11(6):e1184811 (3 total pages)). (Year: 2016).*

Smith et al. 2022 "Knockout of a key gene of the nicotine biosynthetic pathway severely affects tobacco growth under field, but not greenhouse conditions" BMC Research Notes 15:291; https://doi.org/10.1186/s13104-022-06188-9 (6 total pages). (Year: 2022).*

"Coresta Recommended Method No. 7: Determination of Nicotine in the Mainstream Smoke of Cigarettes by Gas Chromatographic Analysis," pp. 1-5, (1987) (updated Aug. 1991) (Paris, France).

"Coresta Recommended Method No. 62: Determination of Nicotine in Tobacco and Tobacco Products by Gas Chromatographic Analysis," *Coresta Cooperation Centre for Scientific Research Relative to Tobacco* (Feb. 2005) (Version 2: Apr. 2020) (Paris, FR).

"Draft for Diplomatic Conference for the Revision of the International Convention for the Protection of New Varieties of Plants," (of Dec. 2, 1961, as revised at Geneva on Nov. 10, 1972; on Oct. 23, 1978; and on Mar. 19, 1991),54 pages, Mar. 4-19, 1991 (Geneva, Switzerland).

International Search Report and Written Opinion issued in International Patent Application No. PCT/US2020/055105, mailed Nov. 27, 2020, 16 pages.

Miller "Memorandum: Proposed Burley Tobacco Grade Index," Legacy Tobacco Document Library, The University of Tennessee Agricultural Experiment Station (Bates Document #523267826-523267833) (Jul. 1988) (Knoxville, USA).

Search Report issued in Chinese Patent Application No. 202080080757X, dated Sep. 5, 2023, with English translation, 5 pages.

Bowman et al., "Revised North Carolina grade index for flue-cured tobacco," *Tobacco Science*, 32: 39-40 (1988).

Centers for Disease Control and Prevention's *Protocol for Analysis of Nicotine, Total Moisture and pH in Smokeless Tobacco Products*, as published in the Federal Register vol. 64, No. Mar. 2, 553, 1999.

Cermak et al., "Efficient design and assembly of custom TALEN and other TAL effector-based constructs for DNA targeting," *Nucleic Acids Research*, 39(12): e82 (2011).

Chaplin et al., "Association Between Percent Total Alkaloids and Other Traits in Flue-cured Tobacco," *Crop Science*, 16(3): 416-418 (1976).

Collins et al., "Determination of nicotine alkaloids in tobacco using the Autoanalyzer," *Tobacco Science* 13: 79-81 (1969).

Davis, "A combined automated procedure for the determination of reducing sugars and nicotine alkaloids in tobacco products using a new reducing sugar method," *Tobacco Science*, 20: 139-144 (1976).

Doyle et al., "TAL Effector-Nucleotide Targeter (TALE-NT) 2.0: tools for TAL effector design and target prediction," *Nucleic Acids Research*, 40: W117-122 (2012).

Estruch et al., "Transgenic plants: An emerging approach to pest control," *Nature Biotechnology*, 15: 137-141 (1997).

Fedoroff et al., "Cloning of the bronze locus in maize by a simple and generalizable procedure using the transposable controlling element Activator (Ac)," *Proceeding of the National Academy of Science, USA*, 81(12): 3825-3829 (1984).

Gaj et al., "ZFN, TALEN and CRISPR/Cas-based methods for genome engineering," *Trends in Biotechnology*, 31(7): 397-405 (2013).

Hibi et al., "Putrescine N-Methyltransferase in Cultured Roots of Hyoscyamus albus 1: n-Butylamine as a Potent Inhibitor of the Transferase both in Vitro and in Vivo," *Plant Physiology*, 100(2): 826-835 (1992).

Hildering et al., "Chimeric Structure of the Tomato Plant After Seed Treatmnt with EMS and X-Rays," in *The Use of Induced Mutations in Plant Breeding*, Pergamon Press, pp. 317-320 (1965).

Hoekema et al., "A binary plant vector strategy based on separation of vir- and T-region of the Agrobacterium tumefaciens Ti-plasmid," *Nature*, 303: 179-180 (1983).

International Search Report and International Preliminary Report on Patentability dated Oct. 9, 2020, PCT/US202/055105.

Kajikawa et al., "Genomic Insights into the Evolution of the Nicotine Biosynthesis Pathway in Tobacco ," *Plant Physiology*, 174(2): 999-1011 (2017).

Legg et al., "Registration of La Burley 21 Tobacco Germplasm1 Registration No. (GP 8)," *Crop Science*, 10(2): 212 (1970).

McCallum et al., "Targeted screening for induced mutations," *Nature Biotechnology*, 18: 455-457 (2000).

Miller et al., "A Grade Index for Type 22 and 23 Fire-Cured Tobacco," *Tobacco Intern*, 192:55-571990.

Morita et al., "Vacuolar transport of nicotine is mediated by a multidrug and toxic compound extrusion (MATE) transporter in Nicotiana tabacum ," *Proceeding of the National Academy of Science, USA*, 106(7): 2447-52 (2009).

(56)  References Cited

OTHER PUBLICATIONS

Official Standard Grades for Burley Tobacco (U.S. Type 31 and Foreign Type 93), effective Nov. 5, 1990 (55 F.R. 40645).

Official Standard Grades for Flue-Cured Tobacco (U.S. Types 11, 12, 13, 14 and Foreign Type 92), effective Mar. 27, 1989 (54 F.R. 7925).

Official Standard Grades for Georgia and Florida Shade-Grown Cigar-Wrapper Tobacco (U.S. Type 62), Effective Apr. 1971.

Official Standard Grades for Ohio Cigar-Leaf Tobacco (U.S. Types 42, 43, and 44), effective Dec. 8, 1963 (28 F.R. 11719 and 28 F.R. 11926).

Official Standard Grades for Pennsylvania Seedleaf Tobacco (U.S. Type 41), effective Jan. 8, 1965 (29 F.R. 16854).

Official Standard Grades for Wisconsin Cigar-Binder Tobacco (U.S. Types 54 and 55), effective Nov. 20, 1969 (34 F.R. 17061).

Poehlman, "Breeding Field Crops," Third Edition (3.sup.rd ed), Springer, New York, NY (1987).

Shoji et al., "Clustered Transcription Factor Genes Regulate Nicotine Biosynthesis in Tobacco," *Plant Cell*, 22(10): 3390-409 (2010).

Smith, "Chapters 4B and 4C of Tobacco: Production" in *Chemistry and Technology*, Davis & Nielsen, eds., Blackwell Publishing, Oxford, pp. 70-103 (1999).

Tso, "Chapter 1: Seed to Smoke," in *Tobacco, Production, Chemistry and Technology*, Davis & Nielsen, eds., Blackwell Publishing, Oxford, pp. 1-31(1999).

Verkerk, "Chimerism of the tomato plant after seed irradiation with fast neutrons," *Netherlands Journal of Agricultural Science*, 19(4): 197-203 (1971).

Wernsman et al., "Chapter Seventeen: Tobacco," in *Principles of Cultivar Development, Volume 2 Crop Species*, W.H. Fehr ed., MacMillan Publishing Go., Inc., New York, N.Y. pp. 669-698 (1987).

Ryan et al., Structure and Expression of the Quinolinate Phosphoribosyltransferase (QPT) gene family in Nicotiana, *Plant Science*, 188-189, pp. 102-110, (Feb. 2012) (electronic publication), available online: DOI: 10.1016/j.plantsci.2012.02.008.

Search Report issued in Chinese Patent Application No. 202080080757X, dated Mar. 1, 2024, with English translation, 4 pages.

Schachtsiek et al., "Brief Communication: Nicotine-free, nontransgenic tobacco (*Nicotiana tabacum* L.) edited by CRISPR-Cas9," *Plant Biotechnology Journal*, 17(12), pp. 2228-2230, (Jul. 2019).

* cited by examiner

COMPOSITIONS AND METHODS BASED ON *QPT* ENGINEERING FOR PRODUCING TOBACCO PLANTS AND PRODUCTS HAVING ALTERED ALKALOID LEVELS

CROSS-REFERENCE TO RELATED APPLICATION AND INCORPORATION OF SEQUENCE LISTING

This application is the U.S. National Stage Application of International Application No. PCT/US2020/055105 filed Oct. 9, 2020, which claims the benefit of U.S. Provisional Application No. 62/913,357, filed Oct. 10, 2019, both of which are incorporated by reference in their entireties herein. A sequence listing contained in the file named "P34736US01_SL.txt" which is 49,978 bytes (measured in MS-Windows R and created on Apr. 8, 2022, is filed electronically herewith and incorporated by reference in its entirety.

FIELD

The present disclosure provides tobacco genetic engineering for modulating alkaloid and nicotine levels.

BACKGROUND

Nicotine is the predominant alkaloid, usually accounting for more than 90-95% of the total alkaloids in commercial tobacco cultivars. The remaining alkaloid fraction is primarily comprised three additional alkaloids: nornicotine, anabasine, and anatabine. Tobacco plants with reduced nicotine levels have been achieved with varying and inconsistent results by modulating different nicotine biosynthetic genes and transcriptional regulators. There is a need for new technologies to reduce nicotine levels in tobacco leaves.

SUMMARY

The present disclosure provides tobacco plants with altered total alkaloid and nicotine levels and commercially acceptable leaf grade, their development via breeding or transgenic approaches, and production of tobacco products from these tobacco plants.

In an aspect, the present disclosure provides a tobacco plant, or part thereof, comprising one or more mutant alleles in at least one QPT gene selected from the group consisting of QPT1a (g98654), QPT1b (g82210), QPT2a (g82211), and QPT2b (g98655), wherein the tobacco plant is capable of producing a leaf comprising a nicotine level less than the nicotine level of a leaf from a control tobacco plant not having the one or more mutant alleles when grown and processed under comparable conditions.

In another aspect, a tobacco plant comprises one or more mutant alleles in at least two QPT genes selected from the group consisting of QPT1a, QPT1b, QPT2a, and QPT2b.

In a further aspect, a tobacco plant comprises one or more mutant alleles in at least three QPT genes selected from the group consisting of QPT1a, QPT1b, QPT2a, and QPT2b.

In another aspect, a tobacco plant comprises one or more mutant alleles in at least four QPT genes selected from the group consisting of QPT1a, QPT1b, QPT2a, and QPT2b.

In an aspect, the present disclosure provides a tobacco plant selected from the group consisting of a single qpt mutant, a double qpt mutant, a triple qpt mutant, and a quadruple qpt mutant.

In an aspect, the present disclosure provides a tobacco plant as listed in Tables 11A and 11B. In another aspect, the present disclosure provides a progeny plant of a tobacco plant in Tables 11A and 11B, from either selfing or a cross with another plant in Tables 11A and 11B.

In another aspect, the present disclosure provides a tobacco plant comprising various combinations of the qpt mutant alleles listed in Tables 11A and 11B to give rise to a single qpt mutant or a double qpt mutant.

The present disclosure further provides cured tobacco, tobacco blends, tobacco products comprising plant material from tobacco plants, lines, varieties or hybrids disclosed.

BRIEF DESCRIPTION OF THE SEQUENCES

SEQ ID NOs: 1 to 4 set forth exemplary genomic sequences of QPT1a, QPT1b, QPT2a, and QPT2b, respectively, from a TN90 reference genome.

SEQ ID NOs: 5 to 8 set forth exemplary cDNA sequences of QPT1a, QPT1b, QPT2a, and QPT2b, respectively, from TN90.

SEQ ID NOs: 9 to 12 set forth exemplary polypeptide sequences of QPT1a, QPT1b, QPT2a, and QPT2b, respectively, from TN90.

SEQ ID NO: 13 sets forth an example guide RNA sequence.

DETAILED DESCRIPTION

Figure 1:
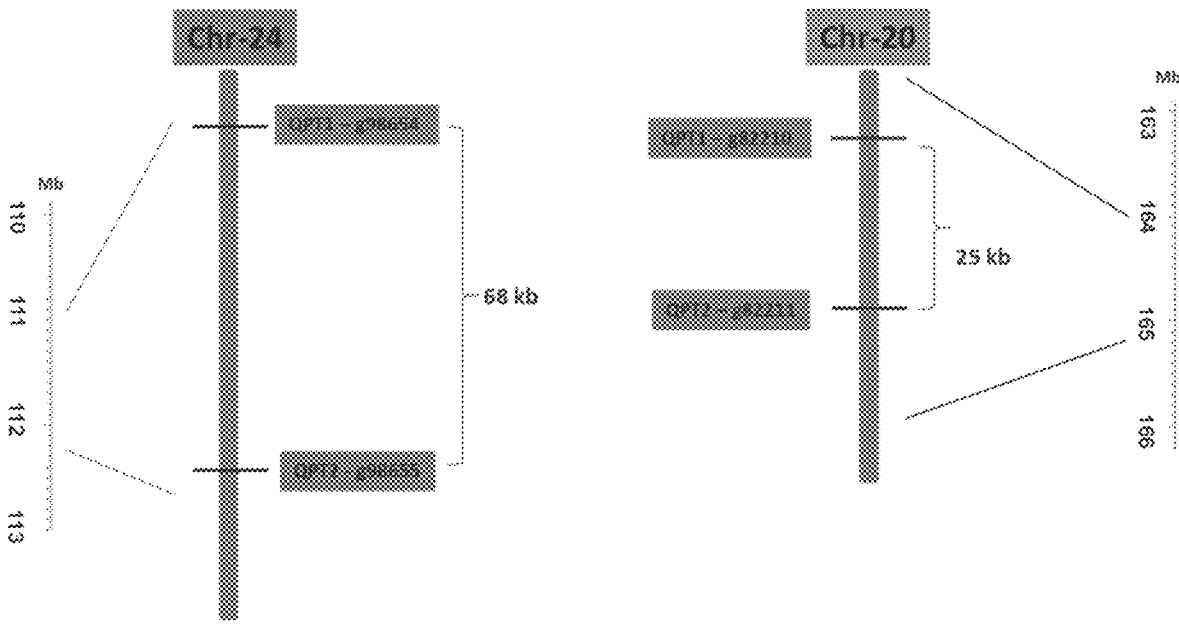
FIG. 1: Genetic map of QPT genes in the tobacco genome.

Unless defined otherwise, technical and scientific terms used herein have the same meaning as commonly understood by one of ordinary skill in the art. One skilled in the art will recognize many methods can be used in the practice of the present disclosure. Indeed, the present disclosure is in no way limited to the methods and materials described. For purposes of the present disclosure, the following terms are defined below.

Any references cited herein, including, e.g., all patents and publications are incorporated by reference in their entirety.

As used herein, the singular form "a," "an,' and "the" include plural references unless the context clearly dictates otherwise. For example, the term "a compound" or "at least one compound" may include a plurality of compounds, including mixtures thereof.

When the term "about" is used in conjunction with a numerical range, it modifies that range by extending the boundaries above and below the numerical values set forth by 10%.

As used herein, phrases such as "less than", "more than", "at least", "at most", "approximately", "below", "above", and "about", when used in conjunction with a series of numerical values, modify each and every value within the series. For example, an expression of "less than 1%, 2%, or 3%" is equivalent to "less than 1%, less than 2%, or less than 3%."

As used herein, a tobacco plant refers to a plant from the species *Nicotiana tabacum*.

Nicotine biosynthesis in tobacco involves the conversion of aspartate to α-iminosuccinate by the enzymes ASPARTATE OXIDASE1 (AO1) and (AO2). From there, α-iminosuccinate is converted to quinolinate by QUINOLINATE SYNTHASE (QS). Quinolate is then converted to nicotianate mononucleotide by QUINOLINATE PHOSPHORIBOSYL TRANSFERASE1 (QPT1) and QPT2. Nicotianate mononucleotide can then be used by tobacco as a direct precursor of nicotine.

QPT enzymes are classified under the enzyme classification system as EC 2.4.2.19. In *Nicotiana tabacum*, four genes encode quinolinate phosphoribosyl transferases, designated QPT1a, QPT1b, QPT2a, and QPT2b. Table 8A lists genomic DNA sequences, cDNA sequences, and protein sequences of these four QPT genes in a TN90 plant. The present disclosure describes compositions and methods that are used to edit QPT genes to produce qpt mutant plants having reduced nicotine levels while maintaining leaf quality.

As used herein, "QPT1a" or the "QPT1a gene" refers to a genic locus in tobacco encoding a polypeptide having an exemplary amino acid sequence in TN90 as set forth in SEQ ID No. 9.

As used herein, "QPT1b" or the "QPT1b gene" refers to a genic locus in tobacco encoding a polypeptide having an exemplary amino acid sequence in TN90 as set forth in SEQ ID No. 10.

As used herein, "QPT2a" or the "QPT2a gene" refers to a genic locus in tobacco encoding a polypeptide having an exemplary amino acid sequence in TN90 as set forth in SEQ ID No. 11.

As used herein, "QPT2b" or the "QPT2b gene" refers to a genic locus in tobacco encoding a polypeptide having an exemplary amino acid sequence in TN90 as set forth in SEQ ID No. 12.

As used herein, a mutation refers to an inheritable genetic modification introduced into a gene to reduce, inhibit, or eliminate the expression or activity of a product encoded by the gene. Such a modification can be in any sequence region of a gene, for example, in a promoter, 5' UTR, exon, intron, 3' UTR, or terminator region. In an aspect, mutations are not natural polymorphisms that exist in a particular tobacco variety or cultivar. As used herein, a "mutant allele" refers to an allele from a locus where the allele comprises a mutation.

As used herein, a "qpt mutant" refers to a tobacco plant comprising one or more mutations in one or more QPT genes. A qpt mutant can be a single mutant, a double mutant, a triple mutant, or a quadruple mutant. As used herein, a single, double, triple, or quadruple qpt mutant refers to a mutant having modifications in one, two, three, or four QPT genes, respectively. A qpt mutant can also be a homozygous mutant, a heterozygous mutant, or a heteroallelic mutant combination in one or more QPT genes.

As used herein, a gene name or a genic locus name is capitalized and shown in italic, e.g., QPT1a, QPT1b, QPT2a, and QPT2b. A protein or polypeptide name is capitalized without being italicized, e.g., QPT1a, QPT1b, QPT2a, and QPT2b. A mutant name (for either referencing to a general mutation in a gene or a group of genes, or referencing to a specific mutant allele) is shown in lower case and italic, e.g., qpt, qpt1a, qpt1b, qpt2a, and qpt2b.

In an aspect, the present disclosure provides a tobacco plant, or part thereof, comprising one or more mutant alleles in at least one QPT gene selected from the group consisting of QPT1a, QPT1b, QPT2a, and QPT2b, wherein the tobacco plant is capable of producing a leaf comprising a nicotine level less than the nicotine level of a leaf from a control tobacco plant not having the one or more mutant alleles when grown and processed under comparable conditions. In an aspect, a single qpt mutant tobacco plant is provided. In another aspect, a single qpt mutant tobacco plant comprises nicotine at a level below 1%, below 2%, below 5%, below 8%, below 10%, below 12%, below 15%, below 20%, below 25%, below 30%, below 40%, below 50%, below 60%, below 70%, below 80%, below 90%, or below 95% of the nicotine level of a control plant not having the single qpt mutation when grown in similar growth conditions. In a further aspect, a single qpt mutant tobacco plant comprises nicotine at a level between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 95% of the nicotine level of a control plant not having the single qpt mutation when grown in similar growth conditions.

In another aspect, a tobacco plant comprises one or more mutant alleles in at least two QPT genes selected from the group consisting of QPT1a, QPT1b, QPT2a, and QPT2b. In an aspect, a double qpt mutant tobacco plant is provided. In another aspect, a double qpt mutant tobacco plant comprises nicotine at a level below 1%, below 2%, below 5%, below 8%, below 10%, below 12%, below 15%, below 20%, below 25%, below 30%, below 40%, below 50%, below 60%, below 70%, below 80%, below 90%, or below 95% of the nicotine level of a control plant not having the double qpt mutations when grown in similar growth conditions. In a further aspect, a double qpt mutant tobacco plant comprises nicotine at a level between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 95% of the nicotine level of a control plant not having the double qpt mutations when grown in similar growth conditions.

In a further aspect, a tobacco plant comprises one or more mutant alleles in at least three QPT genes selected from the group consisting of QPT1a, QPT1b, QPT2a, and QPT2b. In an aspect, a triple qpt mutant tobacco plant is provided. In another aspect, a triple qpt mutant tobacco plant comprises nicotine at a level below 1%, below 2%, below 5%, below 8%, below 10%, below 12%, below 15%, below 20%, below 25%, below 30%, below 40%, below 50%, below 60%, below 70%, below 80%, below 90%, or below 95% of the nicotine level of a control plant not having the triple qpt mutations when grown in similar growth conditions. In a further aspect, a triple qpt mutant tobacco plant comprises nicotine at a level between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 95% of the nicotine level of a control plant not having the triple qpt mutations when grown in similar growth conditions.

In another aspect, a tobacco plant comprises one or more mutant alleles in at least four QPT genes selected from the group consisting of QPT1a, QPT1b, QPT2a, and QPT2b. In an aspect, a quadruple qpt mutant tobacco plant is provided. In another aspect, a quadruple qpt mutant tobacco plant comprises nicotine at a level below 1%, below 2%, below 5%, below 8%, below 10%, below 12%, below 15%, below 20%, below 25%, below 30%, below 40%, below 50%, below 60%, below 70%, below 80%, below 90%, or below 95% of the nicotine level of a control plant not having the quadruple qpt mutations when grown in similar growth conditions. In a further aspect, a quadruple qpt mutant tobacco plant comprises nicotine at a level between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 95% of the nicotine level of a control plant not having the quadruple qpt mutations when grown in similar growth conditions.

In an aspect, a tobacco plant provided herein is a single qpt mutant, a double qpt mutant, a triple qpt mutant, or a quadruple qpt mutant. In another aspect, a tobacco plant comprises one or more qpt mutant alleles listed in Tables 11A and 11B. Each and every combination of the qpt mutant alleles listed in Tables 11A and 11B is also provided to give rise to a single qpt mutant, a double qpt mutant, a triple qpt mutant, or a quadruple qpt mutant. Each of the mutated loci can be either homozygous or heterozygous, or comprises a heteroallelic combination. In another aspect, a tobacco plant comprises a qpt mutant genotype combination as shown for each individual line listed in Tables 11A and 11B.

In an aspect, a tobacco plant is capable of producing a leaf comprising a nicotine level less than 90%, 80%, 70%, 60%, 50%, 40%, 30%, 20%, 15%, 10%, 9%, 8%, 7%, 6%, 5%, 4%, 3%, 2%, 1%, 0.5%, or 0.25% of the nicotine level of a leaf from a control tobacco plant when grown and processed under comparable conditions. In another aspect, a tobacco plant is capable of producing a leaf comprising a nicotine level between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 95% of the nicotine level of a control tobacco plant when grown and processed under comparable conditions.

In another aspect, a tobacco plant is capable of producing a leaf comprising a total alkaloid level less than 90%, 80%, 70%, 60%, 50%, 40%, 30%, 20%, 15%, 10%, 9%, 8%, 7%, 6%, 5%, 4%, 3%, 2%, 1%, 0.5%, or 0.25% of the total alkaloid level of a leaf from a control tobacco plant when grown and processed under comparable conditions. In another aspect, a tobacco plant is capable of producing a leaf comprising a total alkaloid level between 1% and 5%, between 5% and 10%, between 10% and 20%, between 20% and 30%, between 30% and 40%, between 40% and 50%, between 50% and 60%, between 60% and 70%, between 70% and 80%, between 80% and 90%, or between 90% and 95% of the total alkaloid level of a control tobacco plant when grown and processed under comparable conditions.

In a further aspect, a tobacco plant is capable of producing a leaf comprising a total alkaloid level less than 40%, 35%, 30%, 25%, 20%, 15%, 10%, or 5% of the total alkaloid level of a leaf from a control tobacco plant when grown and processed under comparable conditions.

In an aspect, a mutant qpt allele comprises a mutation in a QPT sequence region selected from the group consisting of a promoter, 5' UTR, first exon, first intron, second exon, second intron, third exon, third intron, fourth exon, fourth intron, fifth exon, fifth intron, sixth exon, sixth intron, seventh exon, seventh intron, eighth exon, 3' UTR, terminator, and any combination thereof. In another aspect, a mutant qpt allele comprises a mutation in a QPT genomic sequence region listed in Tables 8D, 8E, 8F, and 8G.

In another aspect, a mutant qpt allele comprises one or more mutation types selected from the group consisting of a nonsense mutation, a missense mutation, a frameshift mutation, a splice-site mutation, and any combination thereof. In an aspect, a mutant qpt allele is a null allele or a knock-out allele.

In an aspect, a mutant qpt allele results in one or more of the following: a QPT protein truncation, a non-translatable QPT gene transcript, a non-functional QPT protein, a premature stop codon in a QPT gene, and any combination thereof.

In another aspect, a mutant qpt allele comprises a mutation selected from the group consisting of a substitution, a deletion, an insertion, a duplication, and an inversion of one or more nucleotides relative to a wild-type QPT gene.

In an aspect, a qpt mutant comprises a zygosity status selected from the group consisting of homozygous, heterozygous, and heteroallelic. In another aspect, a qpt mutant is homozygous or heteroallelic in at least one, two, three, or four QPT genes. In an aspect, a qpt mutant is homozygous or heteroallelic in at least one QPT gene. In an aspect, a qpt mutant is homozygous or heteroallelic in at least two QPT genes. In an aspect, a qpt mutant is homozygous or heteroallelic in at least three QPT genes. In an aspect, a qpt mutant is homozygous or heteroallelic in at least four QPT genes.

In an aspect, a qpt mutant comprises at least one mutation in QPT1a. In another aspect, a qpt mutant comprises at least one mutation in QPT1b. In another aspect, a qpt mutant comprises at least one mutation in QPT2a. In another aspect, a qpt mutant comprises at least one mutation in QPT2b.

In an aspect, a qpt mutant comprises mutations in QPT2a and QPT2b. In another aspect, a qpt mutant comprises mutations in QPT1a and QPT1b. In another aspect, a qpt mutant comprises mutations in QPT1a and QPT2a. In another aspect, a qpt mutant comprises mutations in QPT1a and QPT2b. In another aspect, a qpt mutant comprises mutations in QPT2a and QPT1b. In another aspect, a qpt mutant comprises mutations in QPT1b and QPT2b.

In an aspect, a qpt mutant comprises mutations in QPT1a, QPT1b, and QPT2a. In another aspect, a qpt mutant comprises mutations in QPT1a, QPT1b, and QPT2b. In another aspect, a qpt mutant comprises mutations in QPT1a, QPT2a, and QPT2b. In another aspect, a qpt mutant comprises mutations in QPT1b, QPT2a, and QPT2b.

In another aspect, a qpt mutant comprises mutations in QPT1a, QPT1b, QPT2a, and QPT2b.

In an aspect, a tobacco plant is capable of producing a leaf comprising a nicotine level selected from the group consisting of less than 0.15%, less than 0.125%, less than 0.1%, less than 0.08%, less than 0.06%, less than 0.05%, less than 0.04%, less than 0.03%, less than 0.02%, and less than 0.01% dry weight.

In another aspect, a tobacco plant is capable of producing a leaf comprising a total alkaloid level selected from the group consisting of less than 1%, less than 0.8%, less than 0.7%, less than 0.6%, less than 0.5%, less than 0.4%, less than 0.3%, and less than 0.2% dry weight.

In a further aspect, a tobacco plant is capable of producing a cured leaf comprising a total TSNA level of between 2 and 0.05, between 1.9 and 0.05, between 1.8 and 0.05, between 1.7 and 0.05, between 1.6 and 0.05, between 1.5 and 0.05, between 1.4 and 0.05, between 1.3 and 0.05, between 1.2 and 0.05, between 1.1 and 0.05, between 1.0 and 0.05, between 0.9 and 0.05, between 0.8 and 0.05, between 0.7 and 0.05, between 0.6 and 0.05, between 0.5 and 0.05, between 0.4 and 0.05, between 0.3 and 0.05, between 0.2 and 0.05, between 0.15 and 0.05, or between 0.1 and 0.05 parts per million (ppm).

In an aspect, a tobacco plant is capable of producing leaves, when cured, having a USDA grade index value selected from the group consisting of 50 or more, 55 or more, 60 or more, 65 or more, 70 or more, 75 or more, 80 or more, 85 or more, 90 or more, and 95 or more. In another aspect, a tobacco plant is capable of producing leaves, when cured, having a USDA grade index value comparable to that of a control plant when grown and cured in similar conditions, where the control plant shares an essentially identical genetic background with the tobacco plant except for the modification. In a further aspect, a tobacco plant is capable of producing leaves, when cured, having a USDA grade index value of at least about 65%, at least about 70%, at least about 75%, at least about 80%, at least about 85%, at least about 90%, at least about 95%, or at least about 98% of the USDA grade index value of a control plant when grown in similar conditions, where the control plant shares an essentially identical genetic background with the tobacco plant except the modification. In a further aspect, a tobacco plant is capable of producing leaves, when cured, having a USDA grade index value of between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the USDA grade index value of a control plant. In a further aspect, a tobacco plant is capable of producing leaves, when cured, having a USDA grade index value of between 70% and 125%, between 75% and 120%, between 80% and 115%, between 85% and 110%, or between 90% and 100% of the USDA grade index value of a control plant.

In an aspect, a tobacco plant comprises nicotine at a level below 1%, below 2%, below 5%, below 8%, below 10%, below 12%, below 15%, below 20%, below 25%, below 30%, below 40%, below 50%, below 60%, below 70%, or below 80% of the nicotine level of a control plant when grown in similar growth conditions, where the control plant shares an essentially identical genetic background with the tobacco plant except for the modification.

In a further aspect, a tobacco plant comprises one or more qpt mutant alleles and further comprises a transgene or mutation directly suppressing the expression or activity of one or more genes encoding a product selected from the group consisting of N-methylputrescine oxidase (MPO), putrescine N-methyltransferase (PMT), berberine bridge enzyme-like (BBL), A622, aspartate oxidase (AO), agmatine deiminase (AIC), arginase, diamine oxidase (DAO), ornithine decarboxylase (ODC), arginine decarboxylase, nicotine uptake permease (NUP), and MATE transporter.

In an aspect, a tobacco plant comprises one or more qpt mutant alleles and further comprises a mutation in an ERF gene of Nic2 locus. In an aspect, a tobacco plant further comprises one or more mutations in two or more, three or more, four or more, five or more, six or more, or all seven genes selected from the group consisting of ERF189, ERF115, ERF221, ERF104, ERF179, ERF17, and ERF168. See Shoji et al., *Plant Cell*, (10):3390-409 (2010); and Kajikawa et al., *Plant physiol.* 2017, 174:999-1011. In an aspect, a tobacco plant further comprises one or more mutations in ERF189, ERF115, or both.

In an aspect, a tobacco plant comprises one or more qpt mutant alleles and further comprises a mutation in an ERF gene of Nic1 locus (or Nic1b locus as in PCT/US2019/013345 filed on Jan. 11, 2019, published as WO/2019/140297). See also WO/2018/237107. In an aspect, a tobacco plant further comprises one or more mutations in two or more, three or more, four or more, five or more, six or more, or seven or more genes selected from the group consisting of ERF101, ERF110, ERFnew, ERF199, ERF19, ERF130, ERF16, ERF29, ERF210, and ERF91L2. See Kajikawa et al., *Plant physiol.* 2017, 174:999-1011. In an aspect, a tobacco plant further comprises one or more mutations in one or more, two or more, three or more, four or more, five or more, or all six genes selected from the group consisting of ERFnew, ERF199, ERF19, ERF29, ERF210, and ERF91L2.

A variety of factors affect tobacco alkaloid levels including genotype, environment, fertilization, and agronomic practices (for example, nicotine production is stimulated by topping, wounding, and herbivore damage). Low-alkaloid traits initially found in strains of Cuban cigar tobacco varieties were introduced into cigarette varieties through a series of backcrosses. Low-alkaloid tobacco germplasm was subsequently registered in the genetic background of cultivar Burley 21 (Legg et al., *Crop Science,* 10:212 (1970)). Genetic studies using the low alkaloid Burley 21 (LA BU21) lines indicated that two unlinked loci contribute to nicotine levels in the tobacco leaf. These two loci are referred to as Nic1 and Nic2. nic1 and nic2 (same as nicotine 1 and nicotine 2, respectively) mutations in LA BU21 are semidominant. They show dose-dependent effects on nicotine levels, with the effects of nic1 about 2.4 times stronger than those of nic2. Molecular characterization of Nic2 locus has been reported. The nic2 mutation was shown to contain a deletion of a cluster of transcription factor genes from the ethylene responsive factor (ERF) family, e.g., ERF 189, ERF115, ERF221, ERF104, ERF179, ERF 17, and ERF168 (Shoji et al., *Plant Cell*, (10):3390-409 (2010)).

Reducing total alkaloid content in tobacco can have many benefits. It can increase the value of tobacco as a biomass resource. Increases in nicotinic alkaloid in tobacco plants may play an important role in protecting plants against insects and herbivores.

Consistent with alkaloids' role in insect defense, LA BU21 was reported to be extremely susceptible to insect damage (Legg et al., *Crop Science,* 10:212 (1970)). A further study comparing isogenic lines of flue-cured tobacco with low total alkaloids percentage (approximately 0.20%) with their "normal" recurring parents (total alkaloids 1.85 to 2.70%) reported that yield, grade index, total N, and reducing sugar content in the low alkaloid lines were lower than in the normal flue-cured cultivars (Chaplin and Weeks, *Crop Science*, 16(3):416-18 (1976)).

As used herein, a "low alkaloid variety" of tobacco refers to tobacco variety comprising one or more genetic modifications reducing the total alkaloids (measured via dry weight) to a level less than 25% of the total alkaloid level in a control tobacco variety of a substantially similar genetic background except for the one or more genetic modifications. As a non-limiting example, KY171 can serve as a control for the low-alkaloid variety LA KY171.

In an aspect, the present disclosure further provides a qpt mutant tobacco plant, or part thereof, comprising a nicotine or total alkaloid level selected from the group consisting of less than 3%, less than 2.75%, less than 2.5%, less than 2.25%, less than 2.0%, less than 1.75%, less than 1.5%, less than 1.25%, less than 1%, less than 0.9%, less than 0.8%, less than 0.7%, less than 0.6%, less than 0.5%, less than 0.4%, less than 0.3%, less than 0.2%, less than 0.1%, less than 0.05%, less than 0.025%, less than 0.01%, and less than 0.005%, where the tobacco plant is capable of producing leaves, when cured, having a USDA grade index value of 50 or more 55 or more, 60 or more, 65 or more, 70 or more, 75 or more, 80 or more, 85 or more, 90 or more, and 95 or more. In another aspect, such qpt mutant tobacco plant comprises a nicotine level of less than 0.02% and are capable of producing leaves, when cured, having a USDA grade index value of 70 or more. In a further aspect, such tobacco plant comprises a nicotine level of less than 0.01% and are capable of producing leaves, when cured, having a USDA grade index value of 70 or more.

In an aspect, the present disclosure also provides a tobacco plant, or part thereof, comprising a non-transgenic mutation, where the non-transgenic mutation reduces the nicotine or total alkaloid level of the tobacco plant to below 1%, below 2%, below 5%, below 8%, below 10%, below 12%, below 15%, below 20%, below 25%, below 30%, below 40%, below 50%, below 60%, below 70%, or below 80% of the nicotine level of a control plant when grown in similar growth conditions, where the tobacco plant is capable of producing leaves, when cured, having a USDA grade index value comparable to the USDA grade index value of the control plant, and where the control plant shares an essentially identical genetic background with the tobacco plant except the non-transgenic mutation.

In an aspect, a tobacco plant comprises a qpt mutation introduced by an approach selected from the group consisting of random mutagenesis and targeted mutagenesis. In another aspect, a qpt mutation is introduced by a targeted mutagenesis approach selected from the group consisting of meganuclease, zinc finger nuclease, TALEN, and CRISPR.

Unless specified otherwise, measurements of alkaloid or nicotine levels (or another leaf chemistry or property characterization) or leaf grade index values mentioned herein for a tobacco plant, variety, cultivar, or line refer to average measurements, including, for example, an average of multiple leaves of a single plant or an average measurement from a population of tobacco plants from a single variety, cultivar, or line.

Unless specified otherwise, the nicotine or alkaloid level (or another leaf chemistry or property characterization) of a tobacco plant is measured after topping in a pooled leaf sample collected from leaf number 3, 4, and 5 after topping. As used herein, whenever a comparison between leaves from two plants (e.g., a mutant plant versus a control plant) is mentioned, leaves from the same or comparable stalk position(s) and developmental stage(s) are intended so that the comparison can demonstrate effects due to genotype differences, not from other factors. As an illustration, leaf 3 of a wild-type control plant is intended as a reference point for comparing with leaf 3 of a qpt mutant plant. In an aspect, a tobacco plant comprising at least one qpt mutation is compared to a control tobacco plant of the same tobacco variety.

Nicotine or alkaloid level (or another leaf chemistry or property characterization) of a tobacco plant can also be measured in alternative ways. In an aspect, the nicotine or alkaloid level (or another leaf chemistry or property characterization) of a tobacco plant is measured after topping in a leaf having the highest level of nicotine or alkaloid (or another leaf chemistry or property characterization). In an aspect, the nicotine or alkaloid level of a tobacco plant is measured after topping in leaf number 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In another aspect, the nicotine or alkaloid level (or another leaf chemistry or property characterization) of a tobacco plant is measured after topping in a pool of two or more leaves with consecutive leaf numbers selected from the group consisting of leaf number 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30. In another aspect, the nicotine or alkaloid level (or another leaf chemistry or property characterization) of a tobacco plant is measured after topping in a leaf with a leaf number selected from the group consisting of between 1 and 5, between 6 and 10, between 11 and 15, between 16 and 20, between 21 and 25, and between 26 and 30. In another aspect, the nicotine or alkaloid level (or another leaf chemistry or property characterization) of a tobacco plant is measured after topping in a pool of two or more leaves with leaf numbers selected from the group consisting of between 1 and 5, between 6 and 10, between 11 and 15, between 16 and 20, between 21 and 25, and between 26 and 30. In another aspect, the nicotine or alkaloid level (or another leaf chemistry or property characterization) of a tobacco plant is measured after topping in a pool of three or more leaves with leaf numbers selected from the group consisting of between 1 and 5, between 6 and 10, between 11 and 15, between 16 and 20, between 21 and 25, and between 26 and 30.

As used herein, leaf numbering is based on the leaf position on a tobacco stalk with leaf number 1 being the youngest leaf (at the top) after topping and the highest leaf number assigned to the oldest leaf (at the bottom).

A population of tobacco plants or a collection of tobacco leaves for determining an average measurement (e.g., alkaloid or nicotine level or leaf grading) can be of any size, for example, 5, 10, 15, 20, 25, 30, 35, 40, or 50. Industry-accepted standard protocols are followed for determining average measurements or grade index values.

As used herein, "topping" refers to the removal of the stalk apex, including the shoot apical meristem, flowers, and up to several adjacent leaves, when a tobacco plant is near vegetative maturity and around the start of reproductive growth. Typically, tobacco plants are topped in the button stage (soon after the flower begins to appear). For example, greenhouse or field-grown tobacco plants can be topped when 50% of the plants have at least one open flower. Topping a tobacco plant results in the loss of apical dominance and also induces increased alkaloid production.

Unless indicated otherwise, the nicotine or alkaloid level (or another leaf chemistry or property characterization) of a tobacco plant is measured two weeks after topping. Alternatively, other time points can be used. In an aspect, the nicotine or alkaloid level (or another leaf chemistry or property characterization) of a tobacco plant is measured about 1, 2, 3, 4, or 5 weeks after topping. In another aspect, the nicotine, alkaloid, or polyamine level (or another leaf chemistry or property characterization) of a tobacco plant is measured about 3, 5, 7, 10, 12, 14, 17, 19 or 21 days after topping.

As used herein, "similar growth conditions" or "comparable growth conditions" refer to similar environmental conditions and/or agronomic practices for growing and making meaningful comparisons between two or more plant genotypes so that neither environmental conditions nor agronomic practices would contribute to or explain any difference observed between the two or more plant genotypes. Environmental conditions include, for example, light, temperature, water (humidity), and nutrition (e.g., nitrogen and phosphorus). Agronomic practices include, for example, seeding, clipping, undercutting, transplanting, topping, and suckering. See Chapters 4B and 4C of Tobacco, Production, Chemistry and Technology, Davis & Nielsen, eds., Blackwell Publishing, Oxford (1999), pp 70-103.

"Alkaloids" are complex, nitrogen-containing compounds that naturally occur in plants, and have pharmacological effects in humans and animals. "Nicotine" is the primary natural alkaloid in commercialized cigarette tobacco and accounts for about 90 percent of the alkaloid content in *Nicotiana tabacum*. Other major alkaloids in tobacco include cotinine, nornicotine, myosmine, nicotyrine, anabasine and anatabine. Minor tobacco alkaloids include nicotine-n-oxide, N-methyl anatabine, N-methyl anabasine, pseudooxynicotine, 2,3 dipyridyl and others.

Alkaloid levels can be assayed by methods known in the art, for example by quantification based on gas-liquid chromatography, high performance liquid chromatography, radio-immunoassays, and enzyme-linked immunosorbent assays. For example, nicotinic alkaloid levels can be measured by a GC-FID method based on CORESTA Recommended Method No. 7, 1987 and ISO Standards (ISO TC 126N 394 E. See also Hibi et al., *Plant Physiology* 100: 826-35 (1992) for a method using gas-liquid chromatography equipped with a capillary column and an FID detector.

Unless specifically indicated otherwise, alkaloids and nicotine levels are measured using a method in accordance with CORESTA Method No 62, *Determination of Nicotine in Tobacco and Tobacco Products by Gas Chromatographic Analysis*, February 2005, and those defined in the Centers for Disease Control and Prevention's *Protocol for Analysis of Nicotine, Total Moisture and pH in Smokeless Tobacco Products*, as published in the Federal Register Vol. 64, No. 55 Mar. 23, 1999 (and as amended in Vol. 74, No. 4, Jan. 7, 2009). Alternatively, tobacco total alkaloids can be measured using a segmented-flow colorimetric method developed for analysis of tobacco samples as adapted by Skalar Instrument Co (West Chester, PA) and described by Collins et al., *Tobacco Science* 13:79-81 (1969). In short, samples of tobacco can be dried, ground, and extracted prior to analysis of total alkaloids and reducing sugars. The method then employs an acetic acid/methanol/water extraction and charcoal for decolorization. Determination of total alkaloids is based on the reaction of cyanogen chloride with nicotine alkaloids in the presence of an aromatic amine to form a colored complex which is measured at 460 nm. Unless specified otherwise, total alkaloid levels or nicotine levels shown herein are on a dry weight basis (e.g., percent total alkaloid or percent nicotine).

In an aspect, a tobacco plant comprises an average nicotine or total alkaloid level selected from the group consisting of about 0.01%, 0.02%, 0.05%, 0.75%, 0.1%, 0.15%, 0.2%, 0.35%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 5%, 6%, 7%, 8%, and 9% on a dry weight basis. In another aspect, a tobacco plant comprises an average nicotine or total alkaloid level selected from the group consisting of about between 0.01% and 0.02%, between 0.02% and 0.05%, between 0.05% and 0.75%, between 0.75% and 0.1%, between 0.1% and 0.15%, between 0.15% and 0.2%, between 0.2% and 0.3%, between 0.3% and 0.35%, between 0.35% and 0.4%, between 0.4% and 0.5%, between 0.5% and 0.6%, between 0.6% and 0.7%, between 0.7% and 0.8%, between 0.8% and 0.9%, between 0.9% and 1%, between 1% and 1.1%, between 1.1% and 1.2%, between 1.2% and 1.3%, between 1.3% and 1.4%, between 1.4% and 1.5%, between 1.5% and 1.6%, between 1.6% and 1.7%, between 1.7% and 1.8%, between 1.8% and 1.9%, between 1.9% and 2%, between 2% and 2.1%, between 2.1% and 2.2%, between 2.2% and 2.3%, between 2.3% and 2.4%, between 2.4% and 2.5%, between 2.5% and 2.6%, between 2.6% and 2.7%, between 2.7% and 2.8%, between 2.8% and 2.9%, between 2.9% and 3%, between 3% and 3.1%, between 3.1% and 3.2%, between 3.2% and 3.3%, between 3.3% and 3.4%, between 3.4% and 3.5%, and between 3.5% and 3.6% on a dry weight basis. In a further aspect, a tobacco plant comprises an average nicotine or total alkaloid level selected from the group consisting of about between 0.01% and 0.1%, between 0.02% and 0.2%, between 0.03% and 0.3%, between 0.04% and 0.4%, between 0.05% and 0.5%, between 0.75% and 1%, between 0.1% and 1.5%, between 0.15% and 2%, between 0.2% and 3%, and between 0.3% and 3.5% on a dry weight basis.

The present disclosure also provides a tobacco plant having an altered nicotine level without negative impacts over other tobacco traits, e.g., leaf grade index value. In an aspect, a low-nicotine or nicotine-free tobacco variety provides cured tobacco of commercially acceptable grade. Tobacco grades are evaluated based on factors including, but not limited to, the leaf stalk position, leaf size, leaf color, leaf uniformity and integrity, ripeness, texture, elasticity, sheen (related with the intensity and the depth of coloration of the leaf as well as the shine), hygroscopicity (the faculty of the tobacco leaves to absorb and to retain the ambient moisture), and green nuance or cast. Leaf grade can be determined, for example, using an Official Standard Grade published by the Agricultural Marketing Service of the US Department of Agriculture (7 U.S.C. § 511). See, e.g., Official Standard Grades for Burley Tobacco (U.S. Type 31 and Foreign Type 93), effective Nov. 5, 1990 (55 F.R. 40645); Official Standard Grades for Flue-Cured Tobacco (U.S. Types 11, 12, 13, 14 and Foreign Type 92), effective Mar. 27, 1989 (54 F.R. 7925); Official Standard Grades for Pennsylvania Seedleaf Tobacco (U.S. Type 41), effective January 8, 1965 (29 F.R. 16854); Official Standard Grades for Ohio Cigar-Leaf Tobacco (U.S. Types 42, 43, and 44), effective Dec. 8, 1963 (28 F.R. 11719 and 28 F.R. 11926); Official Standard Grades for Wisconsin Cigar-Binder Tobacco (U.S. Types 54 and 55), effective Nov. 20, 1969 (34 F.R. 17061); Official Standard Grades for Wisconsin Cigar-Binder Tobacco (U.S. Types 54 and 55), effective Nov. 20, 1969 (34 F.R. 17061); Official Standard Grades for Georgia and Florida Shade-Grown Cigar-Wrapper Tobacco (U.S. Type 62), Effective April 1971. A USDA grade index value can be determined according to an industry accepted grade index. See, e.g., Bowman et al, *Tobacco Science,* 32:39-40(1988); Legacy Tobacco Document Library (Bates Document #523267826-523267833, Jul. 1, 1988, Memorandum on the Proposed Burley Tobacco Grade Index); and Miller et al., 1990, *Tobacco Intern.,* 192:55-57 (all foregoing references are incorporated by inference in their entirety). In an aspect, a USDA grade index is a 0-100 numerical representation of federal grade received and is a weighted average of all stalk positions. A higher grade index indicates higher quality. Alternatively, leaf grade can be determined via hyperspectral imaging. See e.g., WO 2011/027315 (published on Mar. 10, 2011, and incorporated by inference in its entirety).

In an aspect, a tobacco plant provided herein comprises a similar level of one or more tobacco aroma compounds compared to a control tobacco plant when grown in similar growth conditions. In another aspect, a tobacco plant provided herein comprise a similar level of one or more tobacco aroma compounds selected from the group consisting of 3-methylvaleric acid, valeric acid, isovaleric acid, a labdenoid, a cembrenoid, a sugar ester, and a reducing sugar, compared to a control tobacco plant when grown in similar growth conditions.

As used herein, tobacco aroma compounds are compounds associated with the flavor and aroma of tobacco smoke. These compounds include, but are not limited to, 3-methylvaleric acid, valeric acid, isovaleric acid, cembrenoid and labdenoid diterpenes, and sugar esters. Concentrations of tobacco aroma compounds can be measured by any known metabolite profiling methods in the art including, without limitation, gas chromatography mass spectrometry (GC-MS), Nuclear Magnetic Resonance Spectroscopy, liquid chromatography-linked mass spectrometry. See The Handbook of Plant Metabolomics, edited by Weckwerth and Kahl, (Wiley-Blackwell) (May 28, 2013).

As used herein, "reducing sugar(s)" are any sugar (monosaccharide or polysaccharide) that has a free or potentially free aldehyde or ketone group. Glucose and fructose act as nicotine buffers in cigarette smoke by reducing smoke pH and effectively reducing the amount of "free" unprotonated nicotine. Reducing sugars balances smoke flavor, for example, by modifying the sensory impact of nicotine and other tobacco alkaloids. An inverse relationship between sugar content and alkaloid content has been reported across tobacco varieties, within the same variety, and within the same plant line caused by planting conditions. Reducing sugar levels can be measured using a segmented-flow colorimetric method developed for analysis of tobacco samples as adapted by Skalar Instrument Co (West Chester, PA) and described by Davis, *Tobacco Science* 20:139-144 (1976). For example, a sample is dialyzed against a sodium carbonate solution. Copper neocuproin is added to the sample and the solution is heated. The copper neocuproin chelate is reduced in the presence of sugars resulting in a colored complex which is measured at 460 nm.

In an aspect, a tobacco plant comprises one or more non-naturally existing mutant alleles in one or more QPT gene loci which reduce or eliminate QPT enzymatic activity from the one or more QPT gene loci. In an aspect, these mutant alleles result in lower nicotine levels. Mutant qpt alleles can be introduced by any method known in the art including random or targeted mutagenesis approaches.

Such mutagenesis methods include, without limitation, treatment of seeds with ethyl methylsulfate (EMS) (Hildering and Verkerk, In, The use of induced mutations in plant breeding. Pergamon press, pp 317-320, 1965) or UV-irradiation, X-rays, and fast neutron irradiation (see, for example, Verkerk, *Neth. J. Agric. Sci.* 19:197-203, 1971; and Poehlman, Breeding Field Crops, Van Nostrand Reinhold, New York (3.sup.rd ed), 1987), transposon tagging (Fedoroff et al., 1984; U.S. Pat. No. 4,732,856 and U.S. Pat. No. 5,013,658), as well as T-DNA insertion methodologies (Hoekema et al., 1983; U.S. Pat. No. 5,149,645). EMS-induced mutagenesis consists of chemically inducing random point mutations over the length of the genome. Fast neutron mutagenesis consists of exposing seeds to neutron bombardment which causes large deletions through double stranded DNA breakage. Transposon tagging comprises inserting a transposon within an endogenous gene to reduce or eliminate expression of the gene. The types of mutations that may be present in a tobacco gene include, for example, point mutations, deletions, insertions, duplications, and inversions. Such mutations desirably are present in the coding region of a tobacco gene; however mutations in the promoter region, and intron, or an untranslated region of a tobacco gene may also be desirable.

In addition, a fast and automatable method for screening for chemically induced mutations, TILLING (Targeting Induced Local Lesions In Genomes), using denaturing HPLC or selective endonuclease digestion of selected PCR products is also applicable to the present disclosure. See, McCallum et al. (2000) *Nat. Biotechnol.* 18:455-457. Mutations that impact gene expression or that interfere with the function of genes can be determined using methods that are well known in the art. Insertional mutations in gene exons usually result in null-mutants. Mutations in conserved residues can be particularly effective in inhibiting the function of a protein. In an aspect, tobacco plants comprise a nonsense (e.g., stop codon) mutation in one or more QPT genes described herein.

It will be appreciated that, when identifying a mutation, the endogenous reference DNA sequence should be from the same variety of tobacco. For example, if a modified tobacco plant comprising a mutation is from the variety TN90, then the endogenous reference sequence must be the endogenous TN90 sequence, not a homologous sequence from a different tobacco variety (e.g., K326). Similarly, if a modified tobacco cell comprising a mutation is a TN90 cell, then the endogenous reference sequence must be the endogenous TN90 sequence, not a homologous sequence from a tobacco cell from a different tobacco variety (e.g., K326).

In an aspect, the present disclosure also provides a tobacco line with altered nicotine levels while maintaining commercially acceptable leaf quality. This line can be produced by introducing mutations into one or more QPT genes via precise genome engineering technologies, for example, Transcription activator-like effector nucleases (TALENs), meganuclease, zinc finger nuclease, and a clustered regularly-interspaced short palindromic repeats (CRISPR)/Cas9 system, a CRISPR/Cpf1 system, a CRISPR/Csm1 system, and a combination thereof (see, for example, U.S. Patent Application publication 2017/0233756). See, e.g., Gaj et al., *Trends in Biotechnology,* 31(7):397-405 (2013).

The screening and selection of mutagenized tobacco plants can be through any methodologies known to those having ordinary skill in the art. Examples of screening and selection methodologies include, but are not limited to, Southern analysis, PCR amplification for detection of a polynucleotide, Northern blots, RNase protection, primerextension, RT-PCR amplification for detecting RNA transcripts, Sanger sequencing, Next Generation sequencing technologies (e.g., Illumina, PacBio, Ion Torrent, 454), enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

In an aspect, a tobacco plant or plant genome provided herein is mutated or edited by a nuclease selected from the group consisting of a meganuclease, a zinc-finger nuclease (ZFN), a transcription activator-like effector nuclease (TALEN), a CRISPR/Cas9 nuclease, a CRISPR/Cpf1 nuclease, or a CRISPR/Csm1 nuclease.

As used herein, "editing" or "genome editing" refers to targeted mutagenesis of at least 1, at least 2, at least 3, at least 4, at least 5, at least 6, at least 7, at least 8, at least 9, or at least 10 nucleotides of an endogenous plant genome nucleic acid sequence, or removal or replacement of an endogenous plant genome nucleic acid sequence. In an aspect, an edited nucleic acid sequence provided has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with an endogenous nucleic acid sequence. In an aspect, an edited nucleic acid sequence provided has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with a polynucleotide selected from the group consisting of SEQ ID NOs: 1 to 8, and fragments thereof. In another aspect, an edited nucleic acid sequence provided has at least 99.9%, at least 99.5%, at least 99%, at least 98%, at least 97%, at least 96%, at least 95%, at least 94%, at least 93%, at least 92%, at least 91%, at least 90%, at least 85%, at least 80%, or at least 75% sequence identity with a polynucleotide encoding a polypeptide selected from the group consisting of SEQ ID NOs: 9 to 12.

Meganucleases, ZFNs, TALENs, CRISPR/Cas9, CRISPR/Csm1 and CRISPR/Cpf1 induce a double-strand DNA break at a target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of donor nucleic acid sequences by HR. In an aspect, a method provided comprises editing a plant genome with a nuclease provided to mutate at least 1, at least 2, at least 3, at least 4, at least 5, at least 6, at least 7, at least 8, at least 9, at least 10, or more than 10 nucleotides in the plant genome via HR with a donor polynucleotide. In an aspect, a mutation provided is caused by genome editing using a nuclease. In another aspect, a mutation provided is caused by non-homologous end-joining or homologous recombination.

Meganucleases, which are commonly identified in microbes, are unique enzymes with high activity and long recognition sequences (>14 bp) resulting in site-specific digestion of target DNA. Engineered versions of naturally occurring meganucleases typically have extended DNA recognition sequences (for example, 14 to 40 bp). The engineering of meganucleases can be more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

ZFNs are synthetic proteins consisting of an engineered zinc finger DNA-binding domain fused to the cleavage domain of the FokI restriction endonuclease. ZFNs can be designed to cleave almost any long stretch of double-stranded DNA for modification of the zinc finger DNA-binding domain. ZFNs form dimers from monomers composed of a non-specific DNA cleavage domain of FokI endonuclease fused to a zinc finger array engineered to bind a target DNA sequence.

The DNA-binding domain of a ZFN is typically composed of 3-4 zinc-finger arrays. The amino acids at positions −1, +2, +3, and +6 relative to the start of the zinc finger ∞-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

The FokI nuclease domain requires dimerization to cleave DNA and therefore two ZFNs with their C-terminal regions are needed to bind opposite DNA strands of the cleavage site (separated by 5-7 bp). The ZFN monomer can cute the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can in principle be re-engineered using one of various methods, customized ZFNs can theoretically be constructed to target nearly any gene sequence. Publicly available methods for engineering zinc finger domains include Context-dependent Assembly (CoDA), Oligomerized Pool Engineering (OPEN), and Modular Assembly.

TALENs are artificial restriction enzymes generated by fusing the transcription activator-like effector (TALE) DNA binding domain to a FokI nuclease domain. When each member of a TALEN pair binds to the DNA sites flanking a target site, the FokI monomers dimerize and cause a double-stranded DNA break at the target site. The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus *Xanthomonas*. The *Xanthomonas* pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

A relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al, *Nucleic Acids Research* (2012) 40: W117-122; Cermak et al., *Nucleic Acids Research* (2011). 39:e82; and tale-nt.cac.cornell.edu/about.

A CRISPR/Cas9 system, CRISPR/Csm1, or a CRISPR/Cpf1 system are alternatives to the FokI-based methods ZFN and TALEN. The CRISPR systems are based on RNA-guided engineered nucleases that use complementary base pairing to recognize DNA sequences at target sites.

CRISPR/Cas9, CRISPR/Csm1, and a CRISPR/Cpf1 systems are part of the adaptive immune system of bacteria and archaea, protecting them against invading nucleic acids such as viruses by cleaving the foreign DNA in a sequence-dependent manner. The immunity is acquired by the integration of short fragments of the invading DNA known as spacers between two adjacent repeats at the proximal end of a CRISPR locus. The CRISPR arrays, including the spacers, are transcribed during subsequent encounters with invasive DNA and are processed into small interfering CRISPR RNAs (crRNAs) approximately 40 nt in length, which combine with the trans-activating CRISPR RNA (tracrRNA) to activate and guide the Cas9 nuclease. This cleaves homologous double-stranded DNA sequences known as protospacers in the invading DNA. A prerequisite for cleavage is the presence of a conserved protospacer-adjacent motif (PAM) downstream of the target DNA, which usually has the sequence 5-NGG-3 but less frequently NAG. Specificity is provided by the so-called "seed sequence" approximately 12 bases upstream of the PAM, which must match between the RNA and target DNA. Cpf1 and Csm1 act in a similar manner to Cas9, but Cpf1 and Csm1 do not require a tracrRNA.

In still another aspect, a tobacco plant provided here comprises one or more qpt mutations and further comprises one or more mutations in one or more loci encoding a nicotine demethylase (e.g., CYP82E4, CYP82E5, CYP82E10) that confer reduced amounts of nornicotine (See U.S. Pat. Nos. 8,319,011; 8,124,851; 9,187,759; 9,228, 194; 9,228,195; 9,247,706) compared to a control plant lacking one or more mutations in one or more loci encoding a nicotine demethylase. In an aspect, a tobacco plant described further comprises reduced nicotine demethylase activity compared to a control plant when grown and cured under comparable conditions.

In an aspect, a qpt mutant tobacco plant further comprises a mutation capable of producing a leaf comprising an anabasine level less than the anabasine level of a leaf from a wild-type control tobacco plant when grown and processed under comparable conditions. In another aspect, a qpt mutant tobacco plant further comprises a mutation capable of producing a leaf comprising an anabasine level less than 5%, 10%, 20%, 25%, 30%, 40%, 50%, 60%, 70%, or 80% of the anabasine level of a leaf from a wild-type control tobacco plant when grown and processed under comparable conditions.

In an aspect, a qpt mutant tobacco plant comprises a further mutation capable of producing a leaf comprising a more than two-fold reduction of the anatabine level compared to a leaf from a control tobacco plant when grown and processed under comparable conditions. In another aspect, a qpt mutant tobacco plant comprises a further mutation capable of producing a leaf comprising a more than 3-, 4-, 5-, 6-, 7-, 8-, 9-, 10-, 11-, 12-, or 13-fold reduction of the anatabine level compared to a leaf from a wild-type control tobacco plant when grown and processed under comparable conditions. In an aspect, a mutation providing lower level of anatabine is a mutation described in US Application Publication No. 2014/0283165 and US Application Publication No. 2016/0010103. In another aspect, a qpt mutant further comprises a mutation in a PMT gene. In a further aspect, a qpt mutant plant further comprises a transgene or mutation suppressing the expression or activity of a PMT gene.

In an aspect, a qpt mutant tobacco plant further comprises a mutation capable of providing a nornicotine level less than 80%, 75%, 70%, 65%, 60%, 55%, 50%, 45%, 40%, or 35% of the nornicotine level of a leaf from a wild-type control tobacco plant when grown and processed under comparable conditions.

In an aspect, a qpt mutant tobacco plant is capable of producing a cured leaf comprising a total N-nitrosonornicotine (NNN) level of less than 2, less than 1.9, less than 1.8, less than 1.7, less than 1.6, less than 1.5, less than 1.4, less than 1.3, less than 1.2, less than 1.1, less than 1.0, less than 0.9, less than 0.8, less than 0.7, less than 0.6, less than 0.5, less than 0.4, less than 0.3, less than 0.2, less than 0.15, less than 0.1, or less than 0.05 ppm.

In another aspect, a qpt mutant tobacco plant is capable of producing a cured leaf comprising a total NNN level of between 2 and 0.05, between 1.9 and 0.05, between 1.8 and between 1.7 and 0.05, between 1.6 and 0.05, between 1.5 and 0.05, between 1.4 and 0.05, between 1.3 and 0.05, between 1.2 and 0.05, between 1.1 and 0.05, between 1.0 and 0.05, between 0.9 and 0.05, between 0.8 and 0.05, between 0.7 and 0.05, between 0.6 and 0.05, between 0.5 and 0.05, between 0.4 and 0.05, between 0.3 and 0.05, between 0.2 and 0.05, between 0.15 and 0.05, or between 0.1 and 0.05 ppm.

In an aspect, a qpt mutant tobacco plant is capable of producing a cured leaf comprising a total nicotine-derived nitrosamine ketone (NNK) level of less than 2, less than 1.9, less than 1.8, less than 1.7, less than 1.6, less than 1.5, less than 1.4, less than 1.3, less than 1.2, less than 1.1, less than 1.0, less than 0.9, less than 0.8, less than 0.7, less than 0.6, less than 0.5, less than 0.4, less than 0.3, less than 0.2, less than 0.15, less than 0.1, or less than 0.05 ppm.

In another aspect, a qpt mutant tobacco plant is capable of producing a cured leaf comprising a total NNK level of between 2 and 0.05, between 1.9 and 0.05, between 1.8 and 0.05, between 1.7 and 0.05, between 1.6 and 0.05, between 1.5 and 0.05, between 1.4 and 0.05, between 1.3 and 0.05, between 1.2 and 0.05, between 1.1 and 0.05, between 1.0 and 0.05, between 0.9 and 0.05, between 0.8 and 0.05, between 0.7 and 0.05, between 0.6 and 0.05, between 0.5 and 0.05, between 0.4 and 0.05, between 0.3 and 0.05, between 0.2 and 0.05, between 0.15 and 0.05, or between 0.1 and 0.05 ppm.

In an aspect, a qpt mutant tobacco plant further comprises a mutation or transgene providing an increased level of one or more antioxidants. In another aspect, a qpt mutant tobacco plant further comprises a genetic modification in an endogenous gene and further comprises an increased level of one or more antioxidants in a cured leaf compared to a control cured tobacco leaf lacking the genetic modification, where the endogenous gene encodes an antioxidant biosynthetic enzyme, a regulatory transcription factor of an antioxidant, an antioxidant transporter, an antioxidant metabolic enzyme, or a combination thereof. In a further aspect, a qpt mutant tobacco plant further comprises a transgene and further comprises an increased level of one or more antioxidants in a cured leaf compared to a control cured tobacco leaf lacking the transgene, where the transgene encodes or directly modulates an antioxidant biosynthetic enzyme, a regulatory transcription factor of an antioxidant, an antioxidant transporter, an antioxidant metabolic enzyme, or a combination thereof. In an aspect, a qpt mutant tobacco plant further comprises a transgene or a cisgenic construct expressing one or more genes selected from the group consisting of AtPAP1, NtAN2, NtAN1, NtJAF13, NtMyb3, chorismate mutase, and arogenate dehydratase (ADT). In another aspect, a qpt mutant tobacco plant further comprises one or more transgenes or genetic modification for increasing antioxidants or decreasing one or more TSNAs as described in WIPO Publication No. 2018/067985 or US Publication No. 2018/0119163.

In an aspect, a tobacco plant described is a modified tobacco plant. As used herein, "modified", in the context of a plant, refers to a plant comprising a genetic alteration introduced for certain purposes and beyond natural polymorphisms.

In an aspect, a tobacco plant described is a cisgenic plant. As used herein, "cisgenesis" or "cisgenic" refers to genetic modification of a plant, plant cell, or plant genome in which all components (e.g., promoter, donor nucleic acid, selection gene) have only plant origins (i.e., no non-plant origin components are used). In an aspect, a plant, plant cell, or plant genome provided is cisgenic. Cisgenic plants, plant cells, and plant genomes provided can lead to ready-to-use tobacco lines. In another aspect, a tobacco plant provided comprises no non-tobacco genetic material or sequences.

As used herein, "gene expression" or expression of a gene refers to the biosynthesis or production of a gene product, including the transcription and/or translation of the gene product.

In an aspect, a tobacco plant provided comprises one or more qpt mutations and further comprises reduced expression or activity of one or more genes involved in nicotine biosynthesis or transport. Genes involved in nicotine biosynthesis include, but are not limited to, arginine decarboxylase (ADC), methylputrescine oxidase (MPO), NADH dehydrogenase, ornithine decarboxylase (ODC), phosphoribosylanthranilate isomerase (PRAI), quinolate phosphoribosyl transferase (QPT), and S-adenosyl-methionine synthetase (SAMS). Nicotine Synthase, which catalyzes the condensation step between a nicotinic acid derivative and methylpyrrolinium cation, has not been elucidated although two candidate genes (A622 and NBB1) have been proposed. See US 2007/0240728 A1 and US 2008/0120737A1. A622 encodes an isoflavone reductase-like protein. In addition, several transporters may be involved in the translocation of nicotine. A transporter gene, named MATE, has been cloned and characterized (Morita et al., *PNAS* 106:2447-52 (2009)).

In an aspect, a tobacco plant provided comprises one or more qpt mutations and further comprises a reduced level of mRNA, protein, or both of one or more genes encoding a product selected from the group consisting of MPO, QPT, ADC, ODC, PRAI, SAMS, BBL, MATE, A622, and NBB1, compared to a control tobacco plant. In another aspect, a tobacco plants provided comprises one or more qpt mutations and further comprises a transgene directly suppressing the expression of one or more genes encoding a product selected from the group consisting of MPO, QPT, ADC, ODC, PRAI, SAMS, BBL, MATE, A622, and NBB1. In another aspect, a tobacco plant provided comprises one or more qpt mutations and further comprises a transgene or mutation suppressing the expression or activity of one or more genes encoding a product selected from the group consisting of MPO, QPT, ADC, ODC, PRAI, SAMS, BBL, MATE, A622, and NBB1.

In an aspect, a tobacco plant provided is from a tobacco type selected from the group consisting of flue-cured tobacco, air-cured tobacco, dark air-cured tobacco, dark fire-cured tobacco, Galpao tobacco, and Oriental tobacco. In another aspect, a tobacco plant provided is from a tobacco type selected from the group consisting of Burley tobacco, Maryland tobacco, and dark tobacco.

Flue-cured tobaccos (also called "Virginia" or "bright" tobaccos) amount to approximately 40% of world tobacco production. Flue-cured tobaccos are often also referred to as "bright tobacco" because of the golden-yellow to deep-orange color it reaches during curing. Flue-cured tobaccos have a light, bright aroma and taste. Flue-cured tobaccos are generally high in sugar and low in oils. Major flue-cured tobacco growing countries are Argentina, Brazil, China, India, Tanzania and the United States of America. In one aspect, tobacco plants or seeds or modified tobacco plants or seeds provided herein are of a flue-cured tobacco variety selected from the group consisting of the varieties listed in Table 1, and any variety essentially derived from any one of the foregoing varieties. See WO 2004/041006 A1. In a further aspect, modified tobacco plants or seeds provided herein are in a flue-cured variety selected from the group consisting of K326, K346, and NC196.

TABLE 1

| Flue-cured Tobacco Varieties |
| --- |
| 400 (TC 225) |
| 401 (TC 226) |
| 401 Cherry Red (TC 227) |
| 401 Cherry Red Free (TC 228) |
| Cash (TC 250) |
| Cash (TI 278) |
| CC 101 |
| CC 1063 |
| CC 13 |
| CC 143 |
| CC 200 |
| CC 27 |
| CC 301 |
| CC 33 |
| CC 35 |
| CC 37 |
| CC 400 |
| CC 500 |
| CC 600 |
| CC 65 |
| CC 67 |
| CC 700 |
| CC 800 |
| CC 900 |
| Coker 139 (TC 259) |
| Coker 139 yb1, yb2 |
| Coker 140 (TC 260) |
| Coker 176 (TC 262) |
| Coker 187 (TC 263) |
| Coker 187-Hicks (TC 265) |
| Coker 209 (TC 267) |
| Coker 258 (TC 270) |
| Coker 298 (TC 272) |
| Coker 316 (TC 273) |
| Coker 319 (TC 274) |
| Coker 347 (TC 275) |
| Coker 371-Gold (TC 276) |
| Coker 411 (TC 277) |
| Coker 48 (TC 253) |
| Coker 51 (TC 254) |
| Coker 86 (TC 256) |
| CU 263 (TC 619) |
| CU 561 |
| DH95-1562-1 |
| Dixie Bright 101 (TC 290) |
| Dixie Bright 102 (TC 291) |
| Dixie Bright 244 (TC 292) |
| Dixie Bright 27 (TC 288) |
| Dixie Bright 28 (TC 289) |
| GF 157 |

TABLE 1-continued

| Flue-cured Tobacco Varieties |
| --- |
| GF 318 |
| GL 26H |
| GL 338 |
| GL 350 |
| GL 368 |
| GL 395 |
| GL 600 |
| GL 737 |
| GL 939 |
| GL 939 (TC 628) |
| Hicks (TC 310) |
| Hicks Broadleaf (TC 311) |
| K 149 (TC 568) |
| K 317 |
| K 326 |
| K 326 (TC 319) |
| K 340 (TC 320) |
| K 346 |
| K 346 (TC 569) |
| K 358 |
| K 394 (TC 321) |
| K 399 |
| K 399 (TC 322) |
| K 730 |
| Lonibow (TI 1573) |
| Lonibow (TI 1613) |
| McNair 10 (TC 330) |
| McNair 135 (TC 337) |
| McNair 30 (TC 334) |
| McNair 373 (TC 338) |
| McNair 944 (TC 339) |
| MK94 (TI 1512) |
| MS K 326 |
| MS NC 71 |
| MS NC 72 |
| NC 100 |
| NC 102 |
| NC 1071 (TC 364) |
| NC 1125-2 |
| NC 12 (TC 346) |
| NC 1226 |
| NC 196 |
| NC 2326 (TC 365) |
| NC 27 NF (TC 349) |
| NC 291 |
| NC 297 |
| NC 299 |
| NC 37 NF (TC 350) |
| NC 471 |
| NC 55 |
| NC 567 (TC 362) |
| NC 60 (TC 352) |
| NC 606 |
| NC 6140 |
| NC 71 |
| NC 72 |
| NC 729 (TC 557) |
| NC 810 (TC 659) |
| NC 82 (TC 356) |
| NC 8640 |
| NC 89 (TC 359) |
| NC 92 |
| NC 925 |
| NC 95 (TC 360) |
| NC 98 (TC 361) |
| NC EX 24 |
| NC PY 10 (TC 367) |
| NC TG 61 |
| Oxford 1 (TC 369) |
| Oxford 1-181 (TC 370) |
| Oxford 2 (TC 371) |
| Oxford 207 (TC 632) |
| Oxford 26 (TC 373) |
| Oxford 3 (TC 372) |
| Oxford 414 NF |
| PD 611 (TC 387) |
| PVH 03 |
| PVH 09 |

TABLE 1-continued

| Flue-cured Tobacco Varieties |
| --- |
| PVH 1118 |
| PVH 1452 |
| PVH 1600 |
| PVH 2110 |
| PVH 2275 |
| R 83 (Line 256-1) (TI 1400) |
| Reams 134 |
| Reams 158 |
| Reams 713 |
| Reams 744 |
| Reams M1 |
| RG 11 (TC 600) |
| RG 13 (TC 601) |
| RG 17 (TC 627) |
| RG 22 (TC 584) |
| RG 8 (TC 585) |
| RG 81 (TC 618) |
| RG H51 |
| RG4H 217 |
| RGH 12 |
| RGH 4 |
| RGH 51 |
| RGH 61 |
| SC 58 (TC 400) |
| SC 72 (TC 403) |
| Sp. G-168 |
| SPEIGHT 168 |
| Speight 168 (TC 633) |
| Speight 172 (TC 634) |
| Speight 178 |
| Speight 179 |
| Speight 190 |
| Speight 196 |
| SPEIGHT 220 |
| SPEIGHT 225 |
| SPEIGHT 227 |
| SPEIGHT 236 |
| Speight G-10 (TC 416) |
| Speight G-102 |
| Speight G-108 |
| Speight G-111 |
| Speight G-117 |
| Speight G-126 |
| Speight G-15 (TC 418) |
| Speight G-23 |
| Speight G-28 (TC 420) |
| Speight G-33 |
| Speight G-41 |
| Speight G-5 |
| Speight G-52 |
| Speight G-58 |
| Speight G-70 |
| Speight G-70 (TC 426) |
| Speight G-80 (TC 427) |
| Speight NF3 (TC 629) |
| STNCB |
| VA 182 |
| VA 45 (TC 559) |
| Vesta 30 (TC 439) |
| Vesta 33 (TC 440) |
| Vesta 5 (TC 438) |
| Vesta 62 (TC 441) |
| Virginia (TI 220) |
| Virginia (TI 273) |
| Virginia (TI 877) |
| Virginia 115 (TC 444) |
| Virginia 21 (TC 443) |
| Virginia Bright (TI 964) |
| Virginia Bright Leaf (TC 446) |
| Virginia Gold (TC 447) |
| White Stem Orinoco (TC 451) |

Air-cured tobaccos include "Burley," "Maryland," and "dark" tobaccos. The common factor linking air-cured tobaccos is that curing occurs primarily without artificial sources of heat and humidity. Burley tobaccos are light to dark brown in color, high in oil, and low in sugar. Burley tobaccos are typically air-cured in barns. Major Burley growing countries include Argentina, Brazil, Italy, Malawi, and the United States of America.

Maryland tobaccos are extremely fluffy, have good burning properties, low nicotine and a neutral aroma. Major Maryland growing countries include the United States of America and Italy.

In one aspect, tobacco plants or seeds or modified tobacco plants or seeds provided herein are of a Burley tobacco variety selected from the group consisting of the tobacco varieties listed in Table 2, and any variety essentially derived from any one of the foregoing varieties. In a further aspect, modified tobacco plants or seeds provided herein are in a Burley variety selected from the group consisting of TN 90, KT 209, KT 206, KT212, and HB 4488.

TABLE 2

| Burley Tobacco Varieties |
| --- |
| 4407 LC |
| AA-37-1 |
| Burley 21 (TC 7) |
| Burley 49 (TC 10) |
| Burley 64 (TC 11) |
| Burley Mammoth KY 16 (TC 12) |
| Clay 402 |
| Clay 403 |
| Clay 502 |
| Clays 403 |
| GR 10 (TC 19) |
| GR 10 (TC 19) |
| GR 10A (TC 20) |
| GR 13 (TC 21) |
| GR 14 (TC 22) |
| GR 149 LC |
| GR 153 |
| GR 17 (TC 23) |
| GR 17B (TC 24) |
| GR 18 (TC 25) |
| GR 19 (TC 26) |
| GR 2 (TC 15) |
| GR 24 (TC 27) |
| GR 36 (TC 28) |
| GR 38 (TC 29) |
| GR 38A (TC 30) |
| GR 40 (TC 31) |
| GR 42 (TC 32) |
| GR 42C (TC 33) |
| GR 43 (TC 34) |
| GR 44 (TC 35) |
| GR 45 (TC 36) |
| GR 46 (TC 37) |
| GR 48 (TC 38) |
| GR 5 (TC 16) |
| GR 53 (TC 39) |
| GR 6 (TC 17) |
| GR 9 (TC 18) |
| GR139 NS |
| GR139 S |
| HB 04P |
| HB 04P LC |
| HB 3307P LC |
| HB 4108P |
| HB 4151P |
| HB 4192P |
| HB 4194P |
| HB 4196 |
| HB 4488 |
| HB 4488P |
| HB04P |
| HB 4488 LC |
| HIB 21 |
| HPB 21 |
| HY 403 |
| Hybrid 403 LC |
| Hybrid 404 LC |
| Hybrid 501 LC |

TABLE 2-continued

| Burley Tobacco Varieties |
| --- |
| KDH-959 (TC 576) |
| KDH-960 (TC 577) |
| KT 200 LC |
| KT 204 LC |
| KT 206 LC |
| KT 209 LC |
| KT 210 LC |
| KT 212 LC |
| KT 215 LC |
| KY 1 (TC 52) |
| KY 10 (TC 55) |
| KY 12 (TC 56) |
| KY 14 (TC 57) |
| KY 14 × L8 LC |
| KY 15 (TC 58) |
| KY 16 (TC 59) |
| KY 17 (TC 60) |
| KY 19 (TC 61) |
| KY 21 (TC 62) |
| KY 22 (TC 63) |
| KY 24 (TC 64) |
| KY 26 (TC 65) |
| KY 33 (TC 66) |
| KY 34 (TC 67) |
| KY 35 (TC 68) |
| KY 41A (TC 69) |
| KY 5 (TC 53) |
| KY 52 (TC 70) |
| KY 54 (TC 71) |
| KY 56 (TC 72) |
| KY 56 (TC 72) |
| KY 57 (TC 73) |
| KY 58 (TC 74) |
| KY 8654 (TC 77) |
| KY 8959 |
| KY 9 (TC 54) |
| KY 907 LC |
| KY 908 (TC 630) |
| NBH 98 (Screened) |
| NC 1206 |
| NC 129 |
| NC 2000 LC |
| NC 2002 LC |
| NC 3 LC |
| NC 5 LC |
| NC 6 LC |
| NC 7 LC |
| NC BH 129 LC |
| NC03-42-2 |
| Newton 98 |
| R 610 LC |
| R 630 LC |
| R 7-11 |
| R 7-12 LC |
| RG 17 |
| TKF 1801 LC |
| TKF 2002 LC |
| TKF 4024 LC |
| TKF 4028 LC |
| TKF 6400 LC |
| TKF 7002 LC |
| TKS 2002 LC |
| TN 86 (TC 82) |
| TN 90 LC |
| TN 97 Hybrid LC |
| TN 97 LC |
| VA 116 |
| VA 119 |
| Virgin A Mutant (TI 1406) |
| Virginia 509 (TC 84) |

In another aspect, tobacco plants or seeds or modified tobacco plants or seeds provided herein are of a Maryland tobacco variety selected from the group consisting of the tobacco varieties listed in Table 3, and any variety essentially derived from any one of the foregoing varieties.

TABLE 3

| Maryland Tobacco Varieties |
| --- |
| Maryland 10 (TC 498) |
| Maryland 14 D2 (TC 499) |
| Maryland 201 (TC 503) |
| Maryland 21 (TC 500) |
| Maryland 341 (TC 504) |
| Maryland 40 |
| Maryland 402 |
| Maryland 59 (TC 501) |
| Maryland 601 |
| Maryland 609 (TC 505) |
| Maryland 64 (TC 502) |
| Maryland 872 (TC 506) |
| Maryland Mammoth (TC 507) |

Dark air-cured tobaccos are distinguished from other tobacco types primarily by its curing process, which gives dark air-cured tobacco its medium-brown to dark-brown color and a distinct aroma. Dark air-cured tobaccos are mainly used in the production of chewing tobacco and snuff. In one aspect, modified tobacco plants or seeds provided herein are of a dark air-cured tobacco variety selected from the group consisting of Sumatra, Jatim, Dominican Cubano, Besuki, One sucker, Green River, Virginia sun-cured, and Paraguan Passado, and any variety essentially derived from any one of the foregoing varieties.

Dark fire-cured tobaccos are generally cured with low-burning wood fires on the floors of closed curing barns. Dark fire-cured tobaccos are typically used for making pipe blends, cigarettes, chewing tobacco, snuff, and strong-tasting cigars. Major growing regions for dark fire-cured tobaccos are Tennessee, Kentucky, and Virginia in the United States of America. In one aspect, tobacco plants or seeds or modified tobacco plants or seeds provided herein are of a dark fire-cured tobacco variety selected from the group consisting of the tobacco varieties listed in Table 4, and any variety essentially derived from any one of the foregoing varieties.

TABLE 4

| Dark Fire-Cured Tobacco Varieties |
| --- |
| Black Mammoth (TC 461) |
| Black Mammoth Small Stalk (TC 641) |
| Certified Madole (TC 463) |
| D-534-A-1 (TC 464) |
| DAC ULT 302 |
| DAC ULT 303 |
| DAC ULT 306 |
| DAC ULT 308 |
| DAC ULT 312 |
| DF 300 (TC 465) |
| DF 485 (TC 466) |
| DF 516 (TC 467) |
| DF 911 (TC 468) |
| DT 508 |
| DT 518 (Screened) |
| DT 538 LC |
| DT 592 |
| Improved Madole (TC 471) |
| Jernigan's Madole (TC 472) |
| KT 14LC |
| KT D17LC |
| KT D4 LC |
| KT D6 LC |
| KT D8 LC |
| KY 153 (TC 216) |
| KY 157 (TC 217) |
| KY 160 |
| KY 160 (TC 218) |
| KY 163 (TC 219) |

TABLE 4-continued

| Dark Fire-Cured Tobacco Varieties |
| --- |
| KY 165 (TC 220) |
| KY 170 (TC 474) |
| KY 171 (PhPh) |
| KY 171 (TC 475) |
| KY 171 LC |
| KY 171 NS |
| KY 180 (TC 573) |
| KY 190 (TC 574) |
| Little Crittenden |
| Little Crittenden (TC 476) |
| Little Crittenden LC (certified) |
| Little Crittenden PhPh |
| Lizard Tail Turtle Foot |
| Madole (TC 478) |
| Madole (TC 479) |
| MS KY 171 |
| MS NL Madole LC |
| MS TN D950 LC |
| Nance (TC 616) |
| Narrow Leaf Madole LC (certified) |
| Neal Smith Madole (TC 646) |
| Newtons VH Madole |
| NL Madole |
| NL Madole (PhPh) |
| NL Madole (TC 484) |
| NL Madole LC |
| NL Madole LC (PhPh) |
| NL Madole NS |
| One Sucker (TC 224) |
| OS 400 |
| PD 302H |
| PD 312H |
| PD 318H |
| PD 7302 LC |
| PD 7305 |
| PD 7309 LC |
| PD 7312 LC |
| PD 7318 LC |
| PD 7319 LC |
| Petico M PG04 |
| PY KY 160 (TC 612) |
| PY KY 171 (TC 613) |
| Shirey |
| TI 1372 |
| TN D94 |
| TN D94 (TC 621) |
| TN D950 |
| TN D950 (PhPh) |
| TN D950 |
| TN D950 (TC 622) |
| TR Madole (TC 486) |
| VA 309 |
| VA 309 (TC 560) |
| VA 309 LC (certified) |
| VA 310 (TC 487) |
| VA 331 (TC 592) |
| VA 355 (TC 638) |
| VA 359 |
| VA 359 (Screened) |
| VA 359 (TC 639) |
| VA 359 LC (certified) |
| VA 403 (TC 580) |
| VA 405 (TC 581) |
| VA 409 (TC 562) |
| VA 510 (TC 572) |

Oriental tobaccos are also referred to as Greek, aroma and Turkish tobaccos due to the fact that they are typically grown in eastern Mediterranean regions such as Turkey, Greece, Bulgaria, Macedonia, Syria, Lebanon, Italy, and Romania. The small plant size, small leaf size, and unique aroma properties of Oriental tobacco varieties are a result of their adaptation to the poor soil and stressful climatic conditions in which they have been developed. In one aspect, tobacco plants or seeds or modified tobacco plants or seeds provided herein are of an Oriental tobacco variety selected from the group consisting of the tobacco varieties listed in Table 5, and any variety essentially derived from any one of the foregoing varieties.

TABLE 5

| Oriental Tobacco Varieties |
| --- |
| Bafra (TI 1641) |
| Bahce (TI 1730) |
| Bahia (TI 1416) |
| Bahia (TI 1455) |
| Baiano (TI 128) |
| Basma |
| Basma (TI 1666) |
| Basma Drama |
| Basma Hybrid (PhPh) |
| Basma Zihna I |
| Bitlis (TI 1667) |
| Bitlis (TI 1725) |
| Bubalovac (TI 1282) |
| Bursa (TI 1650) |
| Bursa (TI 1668) |
| Canik (TI 1644) |
| Djebel 174 (TI 1492) |
| Djebel 359 (TI 1493) |
| Djebel 81 |
| Dubec 566 (TI 1409) |
| Dubec 7 (TI 1410) |
| Dubek 566 (TI 1567) |
| Duzce (TI 1670) |
| Edirne (TI 1671) |
| Ege (TI 1642) |
| Ege-64 (TI 1672) |
| Izmir (Akhisar) (TI 1729) |
| Izmir (Gavurkoy) (TI 1727) |
| Izmir Ege 64 |
| Izmir-Incekara (TI 1674) |
| Izmir-Ozbas (TI 1675) |
| Jaka Dzebel (TI 1326) |
| Kaba-Kulak |
| Kagoshima Maruba (TI 158) |
| Katerini |
| Katerini S53 |
| Krumovgrad 58 |
| MS Basma |
| MS Katerini S53 |
| Nevrokop 1146 |
| Ozbas (TI 1645) |
| Perustitza (TI 980) |
| Prilep (TI 1291) |
| Prilep (TI 1325) |
| Prilep 12-2/1 |
| Prilep 23 |
| Samsun (TC 536) |
| Samsun 959 (TI 1570) |
| Samsun Evkaf (TI 1723) |
| Samsun Holmes NN (TC 540) |
| Samsun Maden (TI 1647) |
| Samsun NO 15 (TC 541) |
| Samsun-BLK SHK Tol (TC 542) |
| Samsun-Canik (TI 1678) |
| Samsun-Maden (TI 1679) |
| Saribaptar 407 - Izmir Region |
| Smyrna (TC 543) |
| Smyrna No. 23 (TC 545) |
| Smyrna No. 9 (TC 544) |
| Smyrna-Blk Shk Tol (TC 546) |
| Trabzon (TI 1649) |
| Trabzon (TI 1682) |
| Trapezund 161 (TI 1407) |
| Turkish (TC 548) |
| Turkish Angshit (TI 90) |
| Turkish Samsum (TI 92) |
| Turkish Tropizoid (TI 93) |
| Turkish Varotic (TI 89) |
| Xanthi (TI 1662) |

In an aspect, tobacco plants or seeds or modified tobacco plants or seeds provided herein are of an cigar tobacco variety selected from the group consisting of the tobacco varieties listed in Table 6, and any variety essentially derived from any one of the foregoing varieties.

TABLE 6

| Cigar Tobacco Varieties |
| --- |
| Bahai (TI 62) |
| Beinhart 1000 |
| Beinhart 1000 (TI 1562) |
| Beinhart 1000-1 (TI 1561) |
| Bergerac C |
| Bergerac C (TI 1529) |
| Big Cuban (TI 1565) |
| Castillo Negro, Blanco, Pina (TI 448) |
| Castillo Negro, Blanco, Pina (TI 448A) |
| Castillo Negro, Blanco, Pina (TI 449) |
| Caujaro (TI 893) |
| Chocoa (TI 289) |
| Chocoa (TI 313) |
| Connecticut 15 (TC 183) |
| Connecticut Broadleaf |
| Connecticut Broadleaf (TC 186) |
| Connecticut Shade (TC 188) |
| Criollo, Colorado (TI 1093) |
| Enshu (TI 1586) |
| Florida 301 |
| Florida 301 (TC 195) |
| PA Broadleaf (TC 119) |
| Pennsylvania Broadleaf |
| Pennsylvania Broadleaf (TC 119) |
| Petite Havana SR1 |
| Petite Havana SR1 (TC 105) |

In an aspect, tobacco plants or seeds or modified tobacco plants or seeds provided herein are of a tobacco variety selected from the group consisting of the tobacco varieties listed in Table 7, and any variety essentially derived from any one of the foregoing varieties.

TABLE 7

| Other Tobacco Varieties |
| --- |
| Chocoa (TI 319) |
| Hoja Parada (TI 1089) |
| Hoja Parado (Galpoa) (TI 1068) |
| Perique (St. James Parrish) |
| Perique (TC 556) |
| Perique (TI 1374) |
| Sylvestris (TI 984) |
| TI 179 |

In an aspect, a tobacco plant, seed, or cell is from a variety selected from the group consisting of the tobacco varieties listed in Table 1, Table 2, Table 3, Table 4, Table 5, Table 6, and Table 7.

In an aspect, low-alkaloid or low-nicotine tobacco plants, seeds, hybrids, varieties, or lines are essentially derived from or in the genetic background of a variety selected from the group consisting of the tobacco varieties listed in Table 1, Table 2, Table 3, Table 4, Table 5, Table 6, and Table 7.

All foregoing mentioned specific varieties of flue-cured, dark air-cured, Burley, Maryland, dark fire-cured, cigar, or Oriental type are listed only for exemplary purposes. Any additional flue-cured, dark air-cured, Burley, Maryland, dark fire-cured, cigar, or Oriental varieties are also contemplated in the present application.

Also provided are populations of tobacco plants described. In an aspect, a population of tobacco plants has a planting density of between about 5,000 and about 8000, between about 5,000 and about 7,600, between about 5,000 and about 7,200, between about 5,000 and about 6,800, between about 5,000 and about 6,400, between about 5,000 and about 6,000, between about 5,000 and about 5,600, between about 5,000 and about 5,200, between about 5,200 and about 8,000, between about 5,600 and about 8,000, between about 6,000 and about 8,000, between about 6,400 and about 8,000, between about 6,800 and about 8,000, between about 7,200 and about 8,000, or between about 7,600 and about 8,000 plants per acre. In another aspect, a population of tobacco plants is in a soil type with low to medium fertility.

Also provided are containers of seeds from tobacco plants described. A container of tobacco seeds of the present disclosure may contain any number, weight, or volume of seeds. For example, a container can contain at least, or greater than, about 100, 200, 300, 400, 500, 600, 700, 800, 900, 1000, 1500, 2000, 2500, 3000, 3500, 4000 or more seeds. Alternatively, the container can contain at least, or greater than, about 1 ounce, 5 ounces, 10 ounces, 1 pound, 2 pounds, 3 pounds, 4 pounds, 5 pounds or more seeds. Containers of tobacco seeds may be any container available in the art. By way of non-limiting example, a container may be a box, a bag, a packet, a pouch, a tape roll, a tube, or a bottle.

Also provided is cured tobacco material made from a low-alkaloid or low-nicotine tobacco plant described. Further provided is cured tobacco material made from a tobacco plant described with higher levels of total alkaloid or nicotine.

"Curing" is the aging process that reduces moisture and brings about the destruction of chlorophyll giving tobacco leaves a golden color and by which starch is converted to sugar. Cured tobacco therefore has a higher reducing sugar content and a lower starch content compared to harvested green leaf. In an aspect, green leaf tobacco provided can be cured using conventional means, e.g., flue-cured, barn-cured, fire-cured, air-cured or sun-cured. See, for example, Tso (1999, Chapter 1 in Tobacco, Production, Chemistry and Technology, Davis & Nielsen, eds., Blackwell Publishing, Oxford) for a description of different types of curing methods. Cured tobacco is usually aged in a wooden drum (e.g., a hogshead) or cardboard cartons in compressed conditions for several years (e.g., two to five years), at a moisture content ranging from 10% to about 25%. See, U.S. Pat. Nos. 4,516,590 and 5,372,149. Cured and aged tobacco then can be further processed. Further processing includes conditioning the tobacco under vacuum with or without the introduction of steam at various temperatures, pasteurization, and fermentation. Fermentation typically is characterized by high initial moisture content, heat generation, and a 10 to 20% loss of dry weight. See, e.g., U.S. Pat. Nos. 4,528,993, 4,660,577, 4,848,373, 5,372,149; U.S. Publication No. 2005/0178398; and Tso (1999, Chapter 1 in Tobacco, Production, Chemistry and Technology, Davis & Nielsen, eds., Blackwell Publishing, Oxford). Cure, aged, and fermented tobacco can be further processed (e.g., cut, shredded, expanded, or blended). See, for example, U.S. Pat. Nos. 4,528,993; 4,660,577; and 4,987,907. In an aspect, the cured tobacco material of the present disclosure is sun-cured. In another aspect, the cured tobacco material of the present disclosure is flue-cured, air-cured, or fire-cured.

Tobacco material obtained from the tobacco lines, varieties or hybrids of the present disclosure can be used to make tobacco products. As used herein, "tobacco product" is defined as any product made or derived from tobacco that is intended for human use or consumption.

Tobacco products provided include, without limitation, cigarette products (e.g., cigarettes and bidi cigarettes), cigar products (e.g., cigar wrapping tobacco and cigarillos), pipe tobacco products, products derived from tobacco, tobacco-derived nicotine products, smokeless tobacco products (e.g., moist snuff, dry snuff, and chewing tobacco), films, chewables, tabs, shaped parts, gels, consumable units, insoluble matrices, hollow shapes, reconstituted tobacco, expanded tobacco, and the like. See, e.g., U.S. Patent Publication No. US 2006/0191548.

As used herein, "cigarette" refers a tobacco product having a "rod" and "filler". The cigarette "rod" includes the cigarette paper, filter, plug wrap (used to contain filtration materials), tipping paper that holds the cigarette paper (including the filler) to the filter, and all glues that hold these components together. The "filler" includes (1) all tobaccos, including but not limited to reconstituted and expanded tobacco, (2) non-tobacco substitutes (including but not limited to herbs, non-tobacco plant materials and other spices that may accompany tobaccos rolled within the cigarette paper), (3) casings, (4) flavorings, and (5) all other additives (that are mixed into tobaccos and substitutes and rolled into the cigarette).

As used herein, "reconstituted tobacco" refers to a part of tobacco filler made from tobacco dust and other tobacco scrap material, processed into sheet form and cut into strips to resemble tobacco. In addition to the cost savings, reconstituted tobacco is very important for its contribution to cigarette taste from processing flavor development using reactions between ammonia and sugars.

As used herein, "expanded tobacco" refers to a part of tobacco filler which is processed through expansion of suitable gases so that the tobacco is "puffed" resulting in reduced density and greater filling capacity. It reduces the weight of tobacco used in cigarettes.

Tobacco products derived from plants of the present disclosure also include cigarettes and other smoking articles, particularly those smoking articles including filter elements, where the rod of smokable material includes cured tobacco within a tobacco blend. In an aspect, a tobacco product of the present disclosure is selected from the group consisting of a cigarillo, a non-ventilated recess filter cigarette, a vented recess filter cigarette, a cigar, snuff, pipe tobacco, cigar tobacco, cigarette tobacco, chewing tobacco, leaf tobacco, hookah tobacco, shredded tobacco, and cut tobacco. In another aspect, a tobacco product of the present disclosure is a smokeless tobacco product. Smokeless tobacco products are not combusted and include, but not limited to, chewing tobacco, moist smokeless tobacco, snus, and dry snuff. Chewing tobacco is coarsely divided tobacco leaf that is typically packaged in a large pouch-like package and used in a plug or twist. Moist smokeless tobacco is a moist, more finely divided tobacco that is provided in loose form or in pouch form and is typically packaged in round cans and used as a pinch or in a pouch placed between an adult tobacco consumer's cheek and gum. Snus is a heat treated smokeless tobacco. Dry snuff is finely ground tobacco that is placed in the mouth or used nasally. In a further aspect, a tobacco product of the present disclosure is selected from the group consisting of loose leaf chewing tobacco, plug chewing tobacco, moist snuff, and nasal snuff. In yet another aspect, a tobacco product of the present disclosure is selected from the group consisting of an electronically heated cigarette, an e-cigarette, an electronic vaporing device.

In an aspect, a tobacco product of the present disclosure can be a blended tobacco product. In another aspect, a tobacco product of the present disclosure can be a low nicotine tobacco product. In a further aspect, a tobacco product of the present disclosure may comprise nornicotine at a level of less than about 3 mg/g. For example, the nornicotine content in such a product can be 3.0 mg/g, 2.5 mg/g, 2.0 mg/g, 1.5 mg/g, 1.0 mg/g, 750 μg/g, 500 pg/g, 250 pg/g, 100 pg/g, 75 pg/g, 50 pg/g, 25 pg/g, 10 pg/g, 7.0 pg/g, 5.0 pg/g, 4.0 pg/g, 2.0 pg/g, 1.0 pg/g, 0.5 pg/g, 0.4 pg/g, 0.2 pg/g, 0.1 pg/g, 0.05 pg/g, 0.01 pg/g, or undetectable.

In an aspect, cured tobacco material or tobacco products provided comprise an average nicotine or total alkaloid level selected from the group consisting of about 0.01%, 0.02%, 0.05%, 0.75%, 0.1%, 0.15%, 0.2%, 0.3%, 0.35%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, 2%, 2.1%, 2.2%, 2.3%, 2.4%, 2.5%, 2.6%, 2.7%, 2.8%, 2.9%, 3%, 3.1%, 3.2%, 3.3%, 3.4%, 3.5%, 3.6%, 3.7%, 3.8%, 3.9%, 4%, 5%, 6%, 7%, 8%, and 9% on a dry weight basis. In another aspect, cured tobacco material or tobacco products provided comprise an average nicotine or total alkaloid level selected from the group consisting of about between 0.01% and 0.02%, between 0.02% and 0.05%, between 0.05% and 0.75%, between 0.75% and 0.1%, between 0.1% and 0.15%, between 0.15% and 0.2%, between 0.2% and 0.3%, between 0.3% and 0.35%, between 0.35% and 0.4%, between 0.4% and 0.5%, between 0.5% and 0.6%, between 0.6% and 0.7%, between 0.7% and 0.8%, between 0.8% and 0.9%, between 0.9% and 1%, between 1% and 1.1%, between 1.1% and 1.2%, between 1.2% and 1.3%, between 1.3% and 1.4%, between 1.4% and 1.5%, between 1.5% and 1.6%, between 1.6% and 1.7%, between 1.7% and 1.8%, between 1.8% and 1.9%, between 1.9% and 2%, between 2% and 2.1%, between 2.1% and 2.2%, between 2.2% and 2.3%, between 2.3% and 2.4%, between 2.4% and 2.5%, between 2.5% and 2.6%, between 2.6% and 2.7%, between 2.7% and 2.8%, between 2.8% and 2.9%, between 2.9% and 3%, between 3% and 3.1%, between 3.1% and 3.2%, between 3.2% and 3.3%, between 3.3% and 3.4%, between 3.4% and 3.5%, and between 3.5% and 3.6% on a dry weight basis. In a further aspect, cured tobacco material or tobacco products provided comprise an average nicotine or total alkaloid level selected from the group consisting of about between 0.01% and 0.1%, between 0.02% and 0.2%, between 0.03% and 0.3%, between 0.04% and 0.4%, between 0.05% and 0.5%, between 0.75% and 1%, between 0.1% and 1.5%, between 0.15% and 2%, between 0.2% and 3%, and between 0.3% and 3.5% on a dry weight basis.

The present disclosure also provides methods for breeding tobacco lines, cultivars, or varieties comprising a desirable level of total alkaloid or nicotine, e.g., low nicotine or nicotine free. Breeding can be carried out via any known procedures. DNA fingerprinting, SNP mapping, haplotype mapping or similar technologies may be used in a marker-assisted selection (MAS) breeding program to transfer or breed a desirable trait or allele into a tobacco plant. For example, a breeder can create segregating populations in a $F_2$ or backcross generation using F1 hybrid plants or further crossing the F1 hybrid plants with other donor plants with an agronomically desirable genotype. Plants in the $F_2$ or backcross generations can be screened for a desired agronomic trait or a desirable chemical profile using one of the techniques known in the art or listed herein. Depending on the expected inheritance pattern or the MAS technology used, self-pollination of selected plants before each cycle of backcrossing to aid identification of the desired individual plants can be performed. Backcrossing or other breeding procedure can be repeated until the desired phenotype of the recurrent parent is recovered. A recurrent parent in the present disclosure can be a flue-cured variety, a Burley variety, a dark air-cured variety, a dark fire-cured variety, or an Oriental variety. Other breeding techniques can be found, for example, in Wernsman, E. A., and Rufty, R. C. 1987. Chapter Seventeen. Tobacco. Pages 669-698 In: Cultivar Development. Crop Species. W.H. Fehr (ed.), MacMillan Publishing Go., Inc., New York, N.Y., incorporated herein by reference in their entirety.

Results of a plant breeding program using the tobacco plants described includes useful lines, cultivars, varieties, progeny, inbreds, and hybrids of the present disclosure. As used herein, the term "variety" refers to a population of plants that share constant characteristics which separate them from other plants of the same species. A variety is often, although not always, sold commercially. While possessing one or more distinctive traits, a variety is further characterized by a very small overall variation between individuals within that variety. A "pure line" variety may be created by several generations of self-pollination and selection, or vegetative propagation from a single parent using tissue or cell culture techniques. A variety can be essentially derived from another line or variety. As defined by the International Convention for the Protection of New Varieties of Plants (Dec. 2, 1961, as revised at Geneva on Nov. 10, 1972; on Oct. 23, 1978; and on Mar. 19, 1991), a variety is "essentially derived" from an initial variety if: a) it is predominantly derived from the initial variety, or from a variety that is predominantly derived from the initial variety, while retaining the expression of the essential characteristics that result from the genotype or combination of genotypes of the initial variety; b) it is clearly distinguishable from the initial variety; and c) except for the differences which result from the act of derivation, it conforms to the initial variety in the expression of the essential characteristics that result from the genotype or combination of genotypes of the initial variety. Essentially derived varieties can be obtained, for example, by the selection of a natural or induced mutant, a somaclonal variant, a variant individual from plants of the initial variety, backcrossing, or transformation. A first tobacco variety and a second tobacco variety from which the first variety is essentially derived, are considered as having essentially identical genetic background. A "line" as distinguished from a variety most often denotes a group of plants used non-commercially, for example in plant research. A line typically displays little overall variation between individuals for one or more traits of interest, although there may be some variation between individuals for other traits.

In an aspect, this disclosure provides a tobacco plant, variety, line, or cell comprising one or more qpt mutations provided in any one of Tables 10A, 10B, 11A, and 11B.

In another aspect, this disclosure provides a tobacco plant, variety, line, or cell derived from any tobacco plant, variety, or line provided in any one of Tables 11A and 11B.

In an aspect, this disclosure provides the tobacco line 19GH655 and $F_1$ or $F_2$ tobacco plants, or male sterile tobacco plants, derived therefrom. In an aspect, this disclosure provides the tobacco line 19GH756 and $F_1$ or $F_2$ tobacco plants, or male sterile tobacco plants, derived therefrom. In an aspect, this disclosure provides the tobacco line 19GH752 and $F_1$ or $F_2$ tobacco plants, or male sterile tobacco plants, derived therefrom. In an aspect, this disclosure provides the tobacco line 19GH753 and $F_1$ or $F_2$ tobacco plants, or male sterile tobacco plants, derived therefrom. In an aspect, this disclosure provides the tobacco line 19GH754 and $F_1$ or $F_2$ tobacco plants, or male sterile tobacco plants, derived therefrom. In an aspect, this disclosure provides the tobacco line 19GH755 and $F_1$ or $F_2$ tobacco plants, or male sterile tobacco plants, derived therefrom. In an aspect, this disclosure provides the tobacco line 19GH749 and $F_1$ or $F_2$ tobacco plants, or male sterile tobacco plants, derived therefrom. In an aspect, this disclosure provides the tobacco line 19GH971 and $F_1$ or $F_2$ tobacco plants, or male sterile tobacco plants, derived therefrom. In an aspect, this disclosure provides the tobacco line 19GH757 and $F_1$ or $F_2$ tobacco plants, or male sterile tobacco plants, derived therefrom. In an aspect, this disclosure provides the tobacco line 19GH972 and $F_1$ or $F_2$ tobacco plants, or male sterile tobacco plants, derived therefrom. In an aspect, this disclosure provides the tobacco line 19GH973 and $F_1$ or $F_2$ tobacco plants, or male sterile tobacco plants, derived therefrom. In an aspect, this disclosure provides the tobacco line 19GH750 and $F_1$ or $F_2$ tobacco plants, or male sterile tobacco plants, derived therefrom. In an aspect, this disclosure provides the tobacco line 19GH796 and $F_1$ or $F_2$ tobacco plants, or male sterile tobacco plants, derived therefrom. In an aspect, this disclosure provides the tobacco line 19GH975 and $F_1$ or $F_2$ tobacco plants, or male sterile tobacco plants, derived therefrom. In an aspect, this disclosure provides the tobacco line 19GH661 and $F_1$ or $F_2$ tobacco plants, or male sterile tobacco plants, derived therefrom. In an aspect, this disclosure provides the tobacco line 19GH662 and $F_1$ or $F_2$ tobacco plants, or male sterile tobacco plants, derived therefrom. In an aspect, this disclosure provides the tobacco line 19GH663 and $F_1$ or $F_2$ tobacco plants, or male sterile tobacco plants, derived therefrom. In an aspect, this disclosure provides the tobacco line 19GH974 and $F_1$ or $F_2$ tobacco plants, or male sterile tobacco plants, derived therefrom. In an aspect, this disclosure provides the tobacco line 19GH352 and $F_1$ or $F_2$ tobacco plants, or male sterile tobacco plants, derived therefrom. In an aspect, this disclosure provides the tobacco line 19GH353 and $F_1$ or $F_2$ tobacco plants, or male sterile tobacco plants, derived therefrom. In an aspect, this disclosure provides the tobacco line 19GH354 and $F_1$ or $F_2$ tobacco plants, or male sterile tobacco plants, derived therefrom. In an aspect, this disclosure provides the tobacco line 19GH797 and $F_1$ or $F_2$ tobacco plants, or male sterile tobacco plants, derived therefrom. In an aspect, this disclosure provides the tobacco line 19GH759 and $F_1$ or $F_2$ tobacco plants, or male sterile tobacco plants, derived therefrom. In an aspect, this disclosure provides the tobacco line 19GH798 and $F_1$ or $F_2$ tobacco plants, or male sterile tobacco plants, derived therefrom. In an aspect, this disclosure provides the tobacco line 19GH1025 and $F_1$ or $F_2$ tobacco plants, or male sterile tobacco plants, derived therefrom. In an aspect, this disclosure provides the tobacco line 19GH355 and $F_1$ or $F_2$ tobacco plants, or male sterile tobacco plants, derived therefrom. In an aspect, this disclosure provides the tobacco line 19GH351 and $F_1$ or $F_2$ tobacco plants, or male sterile tobacco plants, derived therefrom. In an aspect, this disclosure provides the tobacco line 19GH744 and $F_1$ or $F_2$ tobacco plants, or male sterile tobacco plants, derived therefrom. In an aspect, this disclosure provides the tobacco line 19GH746 and $F_1$ or $F_2$ tobacco plants, or male sterile tobacco plants, derived therefrom. In an aspect, this disclosure provides the tobacco line 19GH744 and $F_1$ or $F_2$ tobacco plants, or male sterile tobacco plants, derived therefrom. In an aspect, this disclosure provides the tobacco line 19GH760 and $F_1$ or $F_2$ tobacco plants, or male sterile tobacco plants, derived therefrom.

In an aspect, the present disclosure provides a method of introgressing a low nicotine trait into a tobacco variety, the method comprising: (a) crossing a first tobacco variety comprising a low nicotine trait with a second tobacco variety without the low nicotine trait to produce one or more progeny tobacco plants; (b) genotyping the one or more progeny tobacco plants for a qpt mutant allele selected from those listed in Tables 11A and 11B; and (c) selecting a progeny tobacco plant comprising the qpt mutant allele. In another aspect, these methods further comprise backcrossing the selected progeny tobacco plant with the second tobacco variety. In a further aspect, these methods further comprise: (d) crossing the selected progeny plant with itself or with the second tobacco variety to produce one or more further progeny tobacco plants; and (e) selecting a further progeny tobacco plant comprising a low nicotine trait. In an aspect, the step (e) of selecting comprises marker-assisted selection. In an aspect, these methods produce a single gene conversion comprising a low nicotine trait. In an aspect, these methods produce a single gene conversion comprising a qpt mutant allele. In an aspect, the second tobacco variety is an elite variety. In another aspect, the genotyping step of these methods involve one or more molecular marker assays. In another aspect, the genotyping may involve a polymorphic marker comprising a polymorphism selected from the group consisting of single nucleotide polymorphisms (SNPs), insertions or deletions in DNA sequence (Indels), simple sequence repeats of DNA sequence (SSRs), a restriction fragment length polymorphism (RFLP), and a tag SNP.

As used herein, "locus" is a chromosomal locus or region where a polymorphic nucleic acid, trait determinant, gene, or marker is located. A "locus" can be shared by two homologous chromosomes to refer to their corresponding locus or region. As used herein, "allele" refers to an alternative nucleic acid sequence of a gene or at a particular locus (e.g., a nucleic acid sequence of a gene or locus that is different than other alleles for the same gene or locus). Such an allele can be considered (i) wild-type or (ii) mutant if one or more mutations or edits are present in the nucleic acid sequence of the mutant allele relative to the wild-type allele. A mutant allele for a gene may have a reduced or eliminated activity or expression level for the gene relative to the wild-type allele. For diploid organisms such as tobacco, a first allele can occur on one chromosome, and a second allele can occur at the same locus on a second homologous chromosome. If one allele at a locus on one chromosome of a plant is a mutant allele and the other corresponding allele on the homologous chromosome of the plant is wild-type, then the plant is described as being heterozygous for the mutant allele. However, if both alleles at a locus are mutant alleles, then the plant is described as being homozygous for the mutant alleles. A plant homozygous for mutant alleles at a locus may comprise the same mutant allele or different mutant alleles if heteroallelic or biallelic.

As used herein, "introgression" or "introgress" refers to the transmission of a desired allele of a genetic locus from one genetic background to another.

As used herein, "crossed" or "cross" means to produce progeny via fertilization (e.g. cells, seeds or plants) and includes crosses between plants (sexual) and self-fertilization (selfing).

As used herein, "backcross" and "backcrossing" refer to the process whereby a progeny plant is repeatedly crossed back to one of its parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. The initial cross gives rise to the F1 generation. The term "BC1" refers to the second use of the recurrent parent, "BC2" refers to the third use of the recurrent parent, and so on. In an aspect, a backcross is performed repeatedly, with a progeny individual of each successive backcross generation being itself backcrossed to the same parental genotype.

As used herein, "single gene converted" or "single gene conversion" refers to plants that are developed using a plant breeding technique known as backcrossing, or via genetic engineering, where essentially all of the desired morphological and physiological characteristics of a variety are recovered in addition to the single gene transferred into the variety via the backcrossing technique or via genetic engineering.

As used herein, "elite variety" means any variety that has resulted from breeding and selection for superior agronomic performance.

As used herein, "selecting" or "selection" in the context of marker-assisted selection or breeding refer to the act of picking or choosing desired individuals, normally from a population, based on certain pre-determined criteria.

As used herein, the term "trait" refers to one or more detectable characteristics of a cell or organism which can be influenced by genotype. The phenotype can be observable to the naked eye, or by any other means of evaluation known in the art, e.g., microscopy, biochemical analysis, genomic analysis, an assay for a particular disease tolerance, etc. In some cases, a phenotype is directly controlled by a single gene or genetic locus, e.g., a "single gene trait." In other cases, a phenotype is the result of several genes.

As used herein, "marker assay" means a method for detecting a polymorphism at a particular locus using a particular method, e.g., measurement of at least one phenotype (such as seed color, flower color, or other visually detectable trait), restriction fragment length polymorphism (RFLP), single base extension, electrophoresis, sequence alignment, allelic specific oligonucleotide hybridization (ASO), random amplified polymorphic DNA (RAPD), microarray-based technologies, and nucleic acid sequencing technologies, etc.

As used herein, "marker assisted selection" (MAS) is a process by which phenotypes are selected based on marker genotypes. "Marker assisted selection breeding" refers to the process of selecting a desired trait or traits in a plant or plants by detecting one or more nucleic acids from the plant, where the nucleic acid is linked to the desired trait, and then selecting the plant or germplasm possessing those one or more nucleic acids.

As used herein, "polymorphism" means the presence of one or more variations in a population. A polymorphism may manifest as a variation in the nucleotide sequence of a nucleic acid or as a variation in the amino acid sequence of a protein. Polymorphisms include the presence of one or more variations of a nucleic acid sequence or nucleic acid feature at one or more loci in a population of one or more individuals. The variation may comprise but is not limited to one or more nucleotide base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs), a restriction fragment length polymorphism (RFLP), and a tag SNP. A genetic marker, a gene, a DNA-derived sequence, a RNA-derived sequence, a promoter, a 5' untranslated region of a gene, a 3' untranslated region of a gene, microRNA, siRNA, a tolerance locus, a satellite marker, a transgene, mRNA, ds mRNA, a transcriptional profile, and a methylation pattern may also comprise polymorphisms. In addition, the presence, absence, or variation in copy number of the preceding may comprise polymorphisms.

As used herein, "SNP" or "single nucleotide polymorphism" means a sequence variation that occurs when a single nucleotide (A, T, C, or G) in the genome sequence is altered or variable. "SNP markers" exist when SNPs are mapped to sites on the genome.

As used herein, "marker" or "molecular marker" or "marker locus" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed.

It is understood that any tobacco plant of the present disclosure can further comprise additional agronomically desirable traits, for example, by transformation with a genetic construct or transgene using a technique known in the art. Without limitation, an example of a desired trait is herbicide resistance, pest resistance, disease resistance; high yield; high grade index value; curability; curing quality; mechanical harvestability; holding ability; leaf quality; height, plant maturation (e.g., early maturing, early to medium maturing, medium maturing, medium to late maturing, or late maturing); stalk size (e.g., a small, medium, or a large stalk); or leaf number per plant (e.g., a small (e.g., 5-10 leaves), medium (e.g., 11-15 leaves), or large (e.g., 16-21) number of leaves), or any combination. In an aspect, low-nicotine or nicotine-free tobacco plants or seeds disclosed comprise one or more transgenes expressing one or more insecticidal proteins, such as, for example, a crystal protein of *Bacillus thuringiensis* or a vegetative insecticidal protein from *Bacillus cereus*, such as VIP3 (see, for example, Estruch et al. (1997) *Nat. Biotechnol.* 15:137). In another aspect, tobacco plants further comprise an introgressed trait conferring resistance to brown stem rot (U.S. Pat. No. 5,689,035) or resistance to cyst nematodes (U.S. Pat. No. 5,491,081).

The present disclosure also provides qpt mutant tobacco plants comprising an altered nicotine or total alkaloid level but having a yield comparable to the yield of corresponding initial tobacco plants without such a nicotine level alternation. In an aspect, a qpt mutant tobacco variety provides a yield selected from the group consisting of about between 1200 and 3500, between 1300 and 3400, between 1400 and 3300, between 1500 and 3200, between 1600 and 3100, between 1700 and 3000, between 1800 and 2900, between 1900 and 2800, between 2000 and 2700, between 2100 and 2600, between 2200 and 2500, and between 2300 and 2400 lbs/acre. In another aspect, a qpt mutant tobacco variety provides a yield selected from the group consisting of about between 1200 and 3500, between 1300 and 3500, between 1400 and 3500, between 1500 and 3500, between 1600 and 3500, between 1700 and 3500, between 1800 and 3500, between 1900 and 3500, between 2000 and 3500, between 2100 and 3500, between 2200 and 3500, between 2300 and 3500, between 2400 and 3500, between 2500 and 3500, between 2600 and 3500, between 2700 and 3500, between 2800 and 3500, between 2900 and 3500, between 3000 and 3500, and between 3100 and 3500 lbs/acre. In a further aspect, qpt mutant tobacco plants provide a yield between 65% and 130%, between 70% and 130%, between 75% and 130%, between 80% and 130%, between 85% and 130%, between 90% and 130%, between 95% and 130%, between 100% and 130%, between 105% and 130%, between 110% and 130%, between 115% and 130%, or between 120% and 130% of the yield of a control plant having essentially identical genetic background except for qpt mutation(s). In a further aspect, qpt mutant tobacco plants provide a yield between 70% and 125%, between 75% and 120%, between 80% and 115%, between 85% and 110%, or between 90% and 100% of the yield of a control plant having essentially identical genetic background except for qpt mutation(s).

In an aspect, a tobacco plant disclosed (e.g., a low-nicotine, nicotine-free, or low-alkaloid tobacco variety) comprises a modification conferring a desired trait (e.g., low-nicotine, nicotine-free, or low-alkaloid) without substantially impacting a trait selected from the group consisting of yield, ripening and senescence, susceptibility to insect herbivory, polyamine content after topping, chlorophyll level, mesophyll cell number per unit leaf area, and end-product quality after curing.

In an aspect, a tobacco plant disclosed comprises a modification conferring a desired trait (e.g., low-nicotine, nicotine-free, or low-alkaloid) and further comprises a trait substantially comparable to an unmodified control plant, where the trait is selected from the group consisting of yield, ripening and senescence, susceptibility to insect herbivory, polyamine content after topping, chlorophyll level, meso-phyll cell number per unit leaf area, and end-product quality after curing.

In an aspect, a tobacco plant disclosed comprises a modification conferring a desired trait (e.g., low-nicotine, nicotine-free, or low-alkaloid) and further comprises a yield which is more than 80%, more than 85%, more than 90%, more than 95%, more than 100%, more than 105%, more than 110%, more than 115%, more than 120%, more than 125%, more than 130%, more than 135%, or more than 140% relative to the yield of an unmodified control plant. In an aspect, a tobacco plant disclosed comprises a modification conferring a desired trait (e.g., low-nicotine, nicotine-free, or low-alkaloid) and further comprises a yield which is between 70% and 140%, between 75% and 135%, between 80% and 130%, between 85% and 125%, between 90% and 120%, between 95% and 115%, or between 100% and 110% relative to the yield of an unmodified control plant. In an aspect, a tobacco plant disclosed comprises a modification conferring a desired trait (e.g., low-nicotine, nicotine-free, or low-alkaloid) and further comprises a yield which is between 70% and 80%, between 75% and 85%, between 80% and 90%, between 85% and 95%, between 90% and 100%, between 95% and 105%, between 105% and 115%, between 110% and 120%, between 115% to 125%, between 120% and 130%, between 125 and 135%, or between 130% and 140% relative to the yield of an unmodified control plant.

In an aspect, a low-nicotine or nicotine-free tobacco variety disclosed is adapted for machine harvesting. In another aspect, a low-nicotine or nicotine-free tobacco variety disclosed is harvested mechanically.

In an aspect, a tobacco plant comprising at least one mutant allele in a qpt gene comprises a low-nicotine trait. In another aspect, a tobacco plant comprising at least one mutant allele in a qpt gene comprises a nicotine-free trait. In another aspect, a tobacco plant comprising at least one mutant allele in a qpt gene comprises a low-alkaloid trait.

In an aspect, tobacco plants provided are hybrid plants. Hybrids can be produced by preventing self-pollination of female parent plants (e.g., seed parents) of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by male sterility (MS), or transgenic male sterility where a transgene inhibits microsporogenesis and/or pollen formation, or self-incompatibility. Female parent plants containing MS are particularly useful. In aspects in which the female parent plants are MS, pollen may be harvested from male fertile plants and applied manually to the stigmas of MS female parent plants, and the resulting F1 seed is harvested.

Plants can be used to form single-cross tobacco F1 hybrids. Pollen from a male parent plant is manually transferred to an emasculated female parent plant or a female parent plant that is male sterile to form F1 seed. Alternatively, three-way crosses can be carried out where a single-cross F1 hybrid is used as a female parent and is crossed with a different male parent. As another alternative, double-cross hybrids can be created where the F1 progeny of two different single-crosses are themselves crossed. Self-incompatibility can be used to particular advantage to prevent self-pollination of female parents when forming a double-cross hybrid.

In an aspect, a low-nicotine or nicotine-free tobacco variety is male sterile. In another aspect, a low-nicotine or nicotine-free tobacco variety is cytoplasmic male sterile. Male sterile tobacco plants may be produced by any method known in the art. Methods of producing male sterile tobacco are described in Wernsman, E. A., and Rufty, R. C. 1987. Chapter Seventeen. Tobacco. Pages 669-698 In: Cultivar Development. Crop Species. W.H. Fehr (ed.), MacMillan Publishing Go., Inc., New York, N.Y. 761 pp.

In an aspect, this disclosure provides a male sterile tobacco plant, variety, or line comprising one or more qpt mutations provided in any one of Tables 11A and 11B.

In another aspect, this disclosure provides a male sterile tobacco plant, variety, or line derived from any tobacco plant, variety, or line provided in any one of 10A, 10B, 11A, and 11B.

In a further aspect, tobacco parts provided include, but are not limited to, a leaf, a stem, a root, a seed, a flower, pollen, an anther, an ovule, a pedicel, a fruit, a meristem, a cotyledon, a hypocotyl, a pod, an embryo, endosperm, an explant, a callus, a tissue culture, a shoot, a cell, and a protoplast. In an aspect, tobacco part provided does not include seed. In an aspect, this disclosure provides tobacco plant cells, tissues, and organs that are not reproductive material and do not mediate the natural reproduction of the plant. In another aspect, this disclosure also provides tobacco plant cells, tissues, and organs that are reproductive material and mediate the natural reproduction of the plant. In another aspect, this disclosure provides tobacco plant cells, tissues, and organs that cannot maintain themselves via photosynthesis. In another aspect, this disclosure provides somatic tobacco plant cells. Somatic cells, contrary to germline cells, do not mediate plant reproduction.

Cells, tissues and organs can be from seed, fruit, leaf, cotyledon, hypocotyl, meristem, embryos, endosperm, root, shoot, stem, pod, flower, infloresence, stalk, pedicel, style, stigma, receptacle, petal, sepal, pollen, anther, filament, ovary, ovule, pericarp, phloem, vascular tissue. In another aspect, this disclosure provides a tobacco plant chloroplast. In a further aspect, this disclosure provides epidermal cells, stomata cell, leaf or root hairs, a storage root, or a tuber. In another aspect, this disclosure provides a tobacco protoplast.

Skilled artisans understand that tobacco plants naturally reproduce via seeds, not via asexual reproduction or vegetative propagation. In an aspect, this disclosure provides tobacco endosperm. In another aspect, this disclosure provides tobacco endosperm cells. In a further aspect, this disclosure provides a male or female sterile tobacco plant, which cannot reproduce without human intervention.

In an aspect, the present disclosure provides a nucleic acid molecule comprising at least about 40%, 45%, 50%, 55%, 60%, 65%, 70%, 75%, 80%, 85%, 90%, 91%, 92%, 93%, 94%, 95%, 96%, 97%, 98%, 99%, or 100% identity to a sequence selected from the group consisting of SEQ ID NOs: 1 to 8, and fragments thereof. In an aspect, the present disclosure provides a polypeptide or protein comprising at least about 40%, 45%, 50%, 55%, 60%, 65%, 70%, 75%, 80%, 85%, 90%, 91%, 92%, 93%, 94%, 95%, 96%, 97%, 98%, 99%, or 100% identity to an amino acid sequence selected from the group consisting of SEQ ID NOs: 9 to 12.

As used herein, the term "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution.

The present disclosure further provides a method manufacturing a tobacco product comprising tobacco material from tobacco plants disclosed. In an aspect, methods comprise conditioning aged tobacco material made from tobacco plants to increase its moisture content from between about 12.5% and about 13.5% to about 21%, blending the conditioned tobacco material to produce a desirable blend. In an aspect, the method of manufacturing a tobacco product further comprises casing or flavoring the blend. Generally, during the casing process, casing or sauce materials are added to blends to enhance their quality by balancing the chemical composition and to develop certain desired flavor characteristics. Further details for the casing process can be found in *Tobacco Production, Chemistry and Technology*, Edited by L. Davis and M. Nielsen, Blackwell Science, 1999.

Tobacco material provided can be also processed using methods including, but not limited to, heat treatment (e.g., cooking, toasting), flavoring, enzyme treatment, expansion and/or curing. Both fermented and non-fermented tobaccos can be processed using these techniques. Examples of suitable processed tobaccos include dark air-cured, dark fire cured, burley, flue cured, and cigar filler or wrapper, as well as the products from the whole leaf stemming operation. In an aspect, tobacco fibers include up to 70% dark tobacco on a fresh weight basis. For example, tobacco can be conditioned by heating, sweating and/or pasteurizing steps as described in U.S. Publication Nos. 2004/0118422 or 2005/0178398.

Tobacco material provided can be subject to fermentation. Fermenting typically is characterized by high initial moisture content, heat generation, and a 10 to 20% loss of dry weight. See, e.g., U.S. Pat. Nos. 4,528,993; 4,660,577; 4,848,373; and 5,372,149. In addition to modifying the aroma of the leaf, fermentation can change either or both the color and texture of a leaf. Also during the fermentation process, evolution gases can be produced, oxygen can be taken up, the pH can change, and the amount of water retained can change. See, for example, U.S. Publication No. 2005/0178398 and Tso (1999, Chapter 1 in Tobacco, Production, Chemistry and Technology, Davis & Nielsen, eds., Blackwell Publishing, Oxford). Cured, or cured and fermented tobacco can be further processed (e.g., cut, expanded, blended, milled or comminuted) prior to incorporation into the oral product. The tobacco, in some cases, is long cut fermented cured moist tobacco having an oven volatiles content of between 48 and 50 weight percent prior to mixing with the copolymer and optionally flavorants and other additives.

In an aspect, tobacco material provided can be processed to a desired size. In an aspect, tobacco fibers can be processed to have an average fiber size of less than 200 micrometers. In an aspect, tobacco fibers are between 75 and 125 micrometers. In another aspect, tobacco fibers are processed to have a size of 75 micrometers or less. In an aspect, tobacco fibers include long cut tobacco, which can be cut or shredded into widths of about 10 cuts/inch up to about 110 cuts/inch and lengths of about 0.1 inches up to about 1 inch. Double cut tobacco fibers can have a range of particle sizes such that about 70% of the double cut tobacco fibers falls between the mesh sizes of −20 mesh and 80 mesh.

Tobacco material provided can be processed to have a total oven volatiles content of about 10% by weight or greater; about 20% by weight or greater; about 40% by weight or greater; about 15% by weight to about 25% by weight; about 20% by weight to about 30% by weight; about 30% by weight to about 50% by weight; about 45% by weight to about 65% by weight; or about 50% by weight to about 60% by weight. Those of skill in the art will appreciate that "moist" tobacco typically refers to tobacco that has an oven volatiles content of between about 40% by weight and about 60% by weight (e.g., about 45% by weight to about 55% by weight, or about 50% by weight). As used herein, "oven volatiles" are determined by calculating the percentage of weight loss for a sample after drying the sample in a pre-warmed forced draft oven at 110° C. for 3.25 hours. The oral product can have a different overall oven volatiles content than the oven volatiles content of the tobacco fibers used to make the oral product. The processing steps described can reduce or increase the oven volatiles content.

Having now generally described the disclosure, the same will be more readily understood through reference to the following examples that are provided by way of illustration, and are not intended to be limiting of the present disclosure, unless specified.

EXAMPLES

Example 1: Expression Profiling of Four QPT Genes

Figure 2:
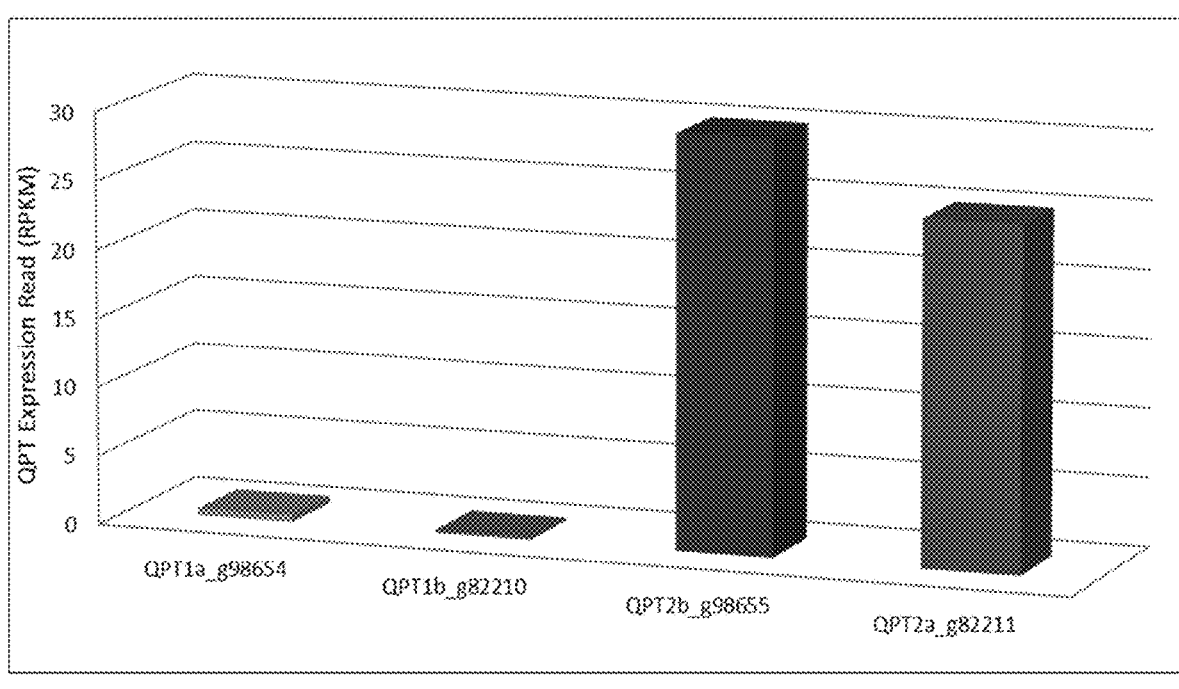
FIG. 2: RNA expression of four QPT genes in TN90 roots. RPKM=reads per kilobase of transcript per million mapped reads.

Nicotine biosynthesis involves the formation of nicotinate mononucleotide, which is later converted into the pyridine ring of nicotine. The formation of nicotinate mononucleotide is catalyzed by quinolinate phosphoribosyl transferase (QPT). Depending on the variety, up to four genes encoding QPT (QPT1a, QPT1b, QPT2a, and QPT2b) are present in the tobacco (*Nicotiana tabacum*) genome (FIG. 1). Table 8A lists genomic DNA sequences, cDNA sequences, and protein sequences of four QPT genes. Tables 8B and 8C provide cDNA and protein sequence identities among four QPT genes. RNA expression levels of four QPT genes in TN90 roots support that, without being limited by any particular theory, QPT2a and QPT2b represent two major QPT genes (FIG. 2).

TABLE 8A

Sequences of four tobacco QPT genes

| Gene Name | Genomic DNA Sequence (including regions such as promoter, 5' UTR, introns, 3' UTR, and terminator) (SEQ ID No.) | CDNA Sequence (SEQ ID No.) | Protein Sequence (SEQ ID No.) |
|---|---|---|---|
| QPT1a | 1 | 5 | 9 |
| QPT1b | 2 | 6 | 10 |
| QPT2a | 3 | 7 | 11 |
| QPT2b | 4 | 8 | 12 |

TABLE 8B cDNA sequence identity among four tobacco QPT genes determined by Clustal2.1

| cDNA % identity | QPT1a | QPT1b | QPT2a | QPT2b |
|---|---|---|---|---|
| QPT1a | 100 | 97.44 | 92.80 | 93.09 |
| QPT1b | 97.44 | 100 | 93.47 | 93.66 |
| QPT2a | 92.80 | 93.47 | 100 | 98.30 |
| QPT2b | 93.09 | 93.66 | 98.30 | 100 |

TABLE 8C

Protein sequence identity among four tobacco QPT genes determined by Clustal2.1

| Protein % identity | QPT1a | QPT1b | QPT2a | QPT2b |
|---|---|---|---|---|
| QPT1a | 100 | 97.72 | 90.06 | 91.48 |
| QPT1b | 97.72 | 100 | 91.76 | 92.33 |
| QPT2a | 90.06 | 91.76 | 100 | 98.30 |
| QPT2b | 91.48 | 92.33 | 98.30 | 100 |

TABLE 8D

QPT1a genomic sequence (SEQ ID No. 1) annotation

| Element | Nucleotide Positions |
|---|---|
| 5' sequence | 1 . . . 544 |
| exon1 | 545 . . . 603 |
| intron1 | 604 . . . 853 |
| exon2 | 854 . . . 987 |
| intron2 | 988 . . . 1649 |
| exon3 | 1650 . . . 1783 |
| intron3 | 1784 . . . 1885 |
| exon4 | 1886 . . . 1949 |
| intron4 | 1950 . . . 2024 |
| exon5 | 2025 . . . 2107 |
| intron5 | 2108 . . . 3209 |
| exon6 | 3210 . . . 3293 |
| intron6 | 3294 . . . 3390 |
| exon7 | 3389 . . . 3541 |
| intron7 | 3542 . . . 4545 |
| exon8 | 4546 . . . 4722 |
| intron8 | 4723 . . . 5114 |
| exon9 | 5115 . . . 5182 |
| intron9 | 5183 . . . 6368 |
| exon10 | 6369 . . . 6465 |
| 3' sequence | 6466 . . . 6749 |

TABLE 8E

QPT1b genomic sequence (SEQ ID No. 2) annotation

| Element | Nucleotide Positions |
|---|---|
| 5' sequence | 1 . . . 634 |
| exon1 | 635 . . . 693 |
| intron1 | 694 . . . 953 |
| exon2 | 954 . . . 1087 |
| intron2 | 1086 . . . 1716 |
| exon3 | 1717 . . . 1850 |
| intron3 | 1851 . . . 1951 |
| exon4 | 1952 . . . 2015 |
| intron4 | 2016 . . . 2090 |
| exon5 | 2091 . . . 2173 |
| intron5 | 2174 . . . 3137 |
| exon6 | 3138 . . . 3221 |
| intron6 | 3222 . . . 3316 |
| exon7 | 3317 . . . 3469 |
| intron7 | 3470 . . . 4607 |
| exon8 | 4608 . . . 4784 |
| intron8 | 4785 . . . 4981 |
| exon9 | 4982 . . . 5049 |
| intron9 | 5050 . . . 6044 |
| exon10 | 6045 . . . 6141 |
| 3' sequence | 6142 . . . 6607 |

TABLE 8F

QPT2a genomic sequence (SEQ ID No. 3) annotation

| Element | Nucleotide Positions |
|---|---|
| 5' sequence | 1 . . . 493 |
| exon1 | 494 . . . 552 |
| intron1 | 553 . . . 664 |
| exon2 | 665 . . . 801 |
| intron2 | 802 . . . 1602 |
| exon3 | 1603 . . . 1734 |
| intron3 | 1735 . . . 1838 |
| exon4 | 1839 . . . 1902 |
| intron4 | 1903 . . . 1975 |
| exon5 | 1976 . . . 2058 |
| intron5 | 2059 . . . 3156 |
| exon6 | 3157 . . . 3240 |
| intron6 | 3241 . . . 3331 |
| exon7 | 3332 . . . 3484 |
| intron7 | 3485 . . . 4055 |

TABLE 8F-continued

| QPT2a genomic sequence (SEQ ID No. 3) annotation | |
| --- | --- |
| Element | Nucleotide Positions |
| exon8 | 4056 . . . 4232 |
| intron8 | 4233 . . . 4524 |
| exon9 | 4525 . . . 4592 |
| intron9 | 4593 . . . 4936 |
| exon10 | 4937 . . . 5033 |
| 3' sequence | 5034 . . . 5494 |

TABLE 8G

| QPT2b genomic sequence (SEQ ID No. 4) annotation | |
| --- | --- |
| Element | Nucleotide Positions |
| 5' sequence | 1 . . . 464 |
| exon1 | 465 . . . 523 |
| intron1 | 524 . . . 634 |
| exon2 | 635 . . . 771 |
| intron2 | 772 . . . 1533 |
| exon3 | 1534 . . . 1667 |
| intron3 | 1668 . . . 1769 |
| exon4 | 1770 . . . 1833 |
| intron4 | 1834 . . . 1906 |
| exon5 | 1907 . . . 1989 |
| intron5 | 1990 . . . 2745 |
| exon6 | 2746 . . . 2829 |
| intron6 | 2830 . . . 2920 |
| exon7 | 2921 . . . 3073 |
| intron7 | 3074 . . . 3532 |
| exon8 | 3533 . . . 3709 |
| intron8 | 3710 . . . 3873 |
| exon9 | 3874 . . . 3941 |
| intron9 | 3942 . . . 4291 |
| exon10 | 4292 . . . 4388 |
| 3' sequence | 4389 . . . 4762 |

Example 2: QPT Genome Editing

QPT knockout mutants are produced by editing various QPT genes. Tobacco protoplasts are transfected using poly-ethylene glycol (PEG) with plasmids encoding a genome editing technology (GET) protein and a specific guide RNA (gRNA) targeting QPT genes at desired positions. Table 9 lists the gRNA sequence used for QPT editing.

Figure 3:
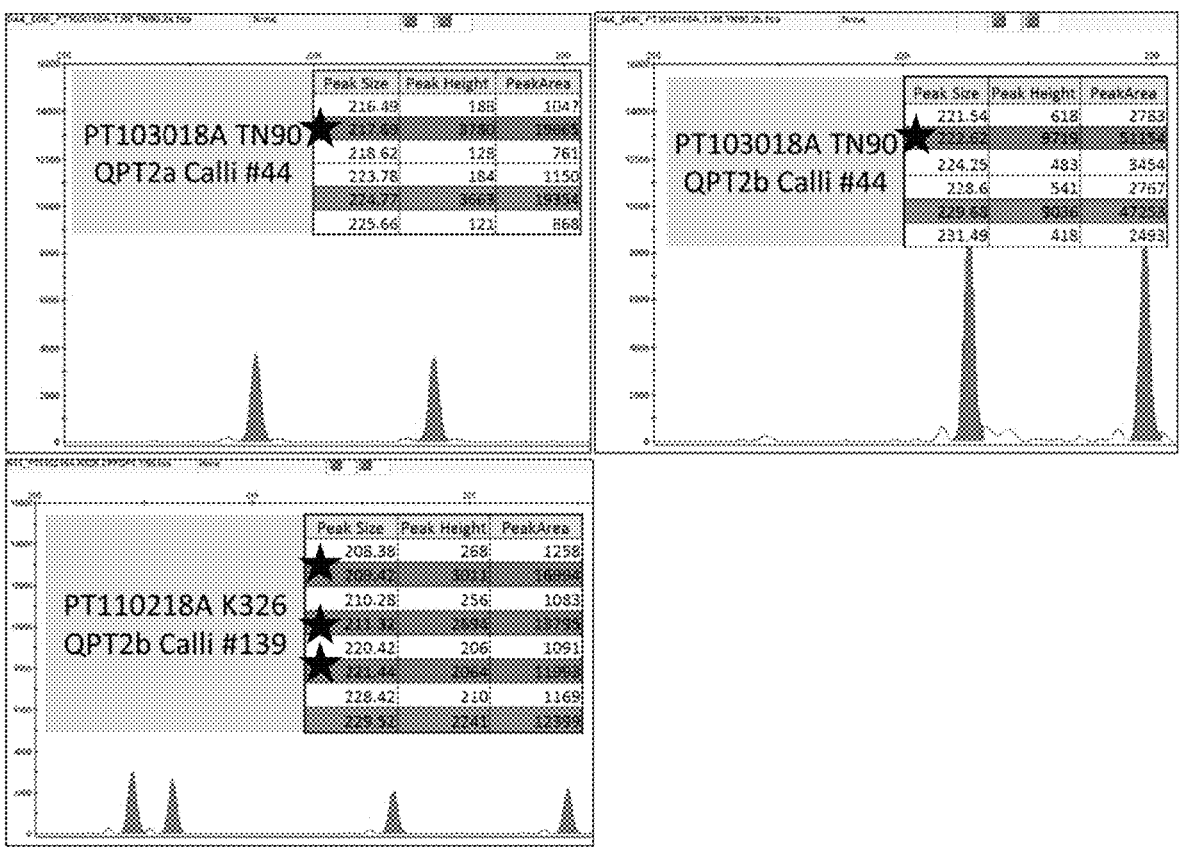
FIG. 3: Depiction of candidate tobacco calli comprising knock-out indels as identified by fragment analysis. Upper panels show the fragment analysis result of both QPT2a, and QPT2b from the TN90 candidate callus #44. The lower panel shows the fragment analysis result of QPT2b from the K326 candidate callus #139. The unmodified QPT gene fragments are shaded, and the edited QPT gene fragments are shaded and denoted with a black star.

Transfected protoplasts are immobilized in 1% agarose beads and subjected to tissue culture. When calli grow up to ~1 mm in diameter, they are spread on TOM2 plates. Calli are screened for insertions or deletions (indels) at the target positions using fragment analysis (FIG. 3). Candidates, showing size shifts compared to wildtype control, are selected for further culture. The consequent shoots and rooted shoots are potted and subject to Next Generation Sequencing (NGS) for the target positions to determine the exact deleted sequences.

TABLE 9 gRNA sequences used in the genome editing technology and its QPT target genes. "Y" represents that a gRNA targets that QPT gene, while "—" represents that a gRNA does not target that QPT gene.

| Genome Editing Techn- ology (GET) | gRNA sequence | QPT1a | QPT1b | QPT2a | QPT2b |
| --- | --- | --- | --- | --- | --- |
| gRNA-QPT1 | TAGCAAAGGAAGACG GGATCATAG (SEQ ID NO: 13) | — | — | Y | Y |

TABLE 10A

Mutant qpt alleles in K326 produced by genome editing using GET. The position of each edited site (e.g., indels) is relative to the nucleotide number on the corresponding cDNA sequence of each QPT gene. For example, line 19GH744 has tri-allelic mutations in OPT2b. One of the three alleles has an 8-nucleotide deletion corresponding to nucleotide positions 269 to 276 of the QPT2b cDNA sequence. The second allele has a 7-nucleotide deletion corresponding to nucleotide positions 270 to 276 of the QPT2b cDNA sequence. The third allele has an 11-nucleotide deletion corresponding to nucleotide positions 266 to 276 of the QPT2b cDNA sequence. SEQ ID numbers are assigned and shown for sequences of 10 or more nucleotides.

| | | QPT2a | | QPT2b | |
| --- | --- | --- | --- | --- | --- |
| Vari-ety | Line | Position | Deleted se-quence | Position | Deleted se-quence |
| K326 | 19GH744 | 268 . . . 274 | GGGAT CA | 269 . . . 276 | GGATCATA |
| | | | | 270 . . . 276 | GATCATA |
| | | | | 266 . . . 276 | ACGGGATC ATA (SEQ ID NO: 14) |
| K326 | 19GH746 | 270 . . . 274 | GATCA | 269 . . . 288 | GGATCATA GCAGGGAT TGCA (SEQ ID NO: 15) |
| | | | | 270 . . . 277 | GATCATAG |
| K326 | 19GH745 | | | 269 . . . 288 | GGATCATA GCAGGGATT GCA (SEQ ID NO: 16) |
| K326 | 19GH794 | | | 266 . . . 276 | ACGGGATCA TA (SEQ ID NO: 17) |

TABLE 10B

Mutant qpt alleles in TN90 produced by genome editing using GET. The position of each edited site (e.g., indels) is relative to the nucleotide number on the corresponding cDNA sequence of each QPT gene. For example, line 19GH752 has bi-allelic mutations in QPT2b. One of the two alleles has a 10-nucleotide deletion corresponding to nucleotide positions 266 to 275 of the QPT2b cDNA sequence. The other allele has an 8-nucleotide deletion corresponding to nucleotide positions 268 to 275 of the QPT2b cDNA sequence. SEQ ID numbers are assigned and shown for sequences of 10 or more nucleotides.

| Variety | Line | QPT2a Position | QPT2a Deleted sequence | QPT2b Position | QPT2b Deleted sequence |
|---|---|---|---|---|---|
| TN90 | 19GH 655 | 268 ... 274 | GGGATCA | | |
| TN90 | 19GH 756 | 268 ... 274 | GGGATCA | | |
| TN90 | 19GH 752 | 269 ... 271 | GGA | 266 ... 275 | ACGGGAT CAT (SEQ ID NO: 19) |
| | | | | 268 ... 275 | GGGATCA T |
| TN90 | 19GH 753 | 269 ... 271 | GGA | 266 ... 275 | ACGGGAT CAT (SEQ ID NO: 19) |
| | | | | 268 ... 275 | GGGATCA T |
| TN90 | 19GH 754 | 269 ... 271 | GGA | 266 ... 275 | ACGGGAT CAT (SEQ ID NO: 19) |
| | | | | 268 ... 275 | GGGATCAT |
| TN90 | 19GH 755 | 264 ... 274 | AGACGGG ATCA (SEQ ID NO: 18) | 269 ... 276 | GGATCATA |
| | | 269 ... 274 | GGATCA | 270 ... 274 | GATCA |
| | | 270 ... 275 | GATCAT | | |
| TN90 | 19GH 749 | 264 ... 274 | AGACGGG ATCA (SEQ ID NO: 18) | 269 ... 276 | GGATCATA |
| | | 269 ... 274 | GGATCA | 270 ... 274 | GATCA |
| | | 270 ... 275 | GATCAT | | |
| TN90 | 19GH 971 | 264 ... 274 | AGACGGG ATCA (SEQ ID NO: 18) | 269 ... 276 | GGATCATA |
| | | 269 ... 274 | GGATCA | 270 ... 274 | GATCA |

TABLE 10B-continued

Mutant qpt alleles in TN90 produced by genome editing using GET. The position of each edited site (e.g., indels) is relative to the nucleotide number on the corresponding cDNA sequence of each QPT gene. For example, line 19GH752 has bi-allelic mutations in QPT2b. One of the two alleles has a 10-nucleotide deletion corresponding to nucleotide positions 266 to 275 of the QPT2b cDNA sequence. The other allele has an 8-nucleotide deletion corresponding to nucleotide positions 268 to 275 of the QPT2b cDNA sequence. SEQ ID numbers are assigned and shown for sequences of 10 or more nucleotides.

| Variety | Line | QPT2a Position | QPT2a Deleted sequence | QPT2b Position | QPT2b Deleted sequence |
|---|---|---|---|---|---|
| TN90 | 19GH 757 | 269 ... 275 | GGATCAT | 269 ... 275 | GGATCAT |
| TN90 | 19GH 972 | 270 ... 275 | GATCAT | 270 ... 274 | GATCA |
| | | | | 274 ... 275 | AT |
| TN90 | 19GH 973 | 268 ... 276 | GGGATCA TA | 268 ... 275 | GGGATCAT |
| | | | | 269 ... 276 | GGATCATA |
| TN90 | 19GH 750 | 268 ... 275 | GGGATCA T | 269 ... 276 | GGATCATA |
| | | 269 ... 275 | GGATCAT | 270 ... 274 | GATCA |
| TN90 | 19GH 796 | 269 ... 276 | GGATCAT A | 269 ... 275 | GGATCAT |
| TN90 | 19GH 975 | 269 ... 276 | GGATCAT A | 269 ... 275 | GGATCAT |
| TN90 | 19GH 661 | 268 ... 275 | GGGATCA T | 266 ... 274 | ACGGGAT CA |
| | | 270 ... 271 | GA | 270 ... 276 | GATCATA |
| TN90 | 19GH 662 | 268 ... 275 | GGGATCA T | 266 ... 274 | ACGGGAT CA |
| | | 270 ... 271 | GA | 270 ... 276 | GATCATA |
| TN90 | 19GH 663 | 268 ... 275 | GGGATCA T | 270 ... 276 | GATCATA |
| | | 270 ... 271 | GA | 266 ... 274 | ACGGGAT CA |
| TN90 | 19GH 974 | 269 ... 273 | GGATC | | |
| TN90 | 19GH 352 | 269 ... 272 | GGAT | 269 ... 276 | GGATCATA |
| TN90 | 19GH 353 | 269 ... 272 | GGAT | 269 ... 276 | GGATCATA |
| TN90 | 19GH 354 | 269 ... 272 | GGAT | 269 ... 276 | GGATCATA |
| TN90 | 19GH 797 | 269 ... 272 | GGAT | 269 ... 276 | GGATCATA |

TABLE 10B-continued

Mutant qpt alleles in TN90 produced by genome editing using GET. The position of each edited site (e.g., indels) is relative to the nucleotide number on the corresponding cDNA sequence of each QPT gene. For example, line 19GH752 has bi-allelic mutations in QPT2b. One of the two alleles has a 10-nucleotide deletion corresponding to nucleotide positions 266 to 275 of the QPT2b cDNA sequence. The other allele has an 8-nucleotide deletion corresponding to nucleotide positions 268 to 275 of the QPT2b cDNA sequence. SEQ ID numbers are assigned and shown for sequences of 10 or more nucleotides.

| Variety | Line | QPT2a Position | Deleted sequence | QPT2b Position | Deleted sequence |
|---|---|---|---|---|---|
| TN90 | 19GH 759 | 270 . . . 274 | GATCA | 269 . . . 275 | GGATCAT |
| TN90 | 19GH 798 | 270 . . . 274 | GATCA | 269 . . . 275 | GGATCAT |
| TN90 | 19GH 1025 | 270 . . . 274 | GATCA | 269 . . . 275 | GGATCAT |
| TN90 | 19GH 760 | | | 270 . . . 276 | GATCATA |
| TN90 | 19GH 355 | 270 . . . 276 | GATCATA | 269 . . . 276 | GGATCATA |
| TN90 | 19GH 351 | 270 . . . 276 | GATCATA | 269 . . . 276 | GGATCATA |
| TN90 | ??? | 270 . . . 276 | GATCATA | 269 . . . 276 | GGATCATA |

TABLE 11A

Exemplary mutant alleles obtained in the QPT2a gene

| Variety | Line | Position | Deleted sequence |
|---|---|---|---|
| TN90 | 19GH655 | 268 . . . 274 | GGGATCA |
| TN90 | 19GH756 | 268 . . . 274 | GGGATCA |
| TN90 | 19GH752 | 269 . . . 271 | GGA |
| TN90 | 19GH753 | 269 . . . 271 | GGA |
| TN90 | 19GH754 | 269 . . . 271 | GGA |
| TN90 | 19GH755 | 264 . . . 274 | AGACGGGATCA (SEQ ID NO: 18) |
| | | 269 . . . 274 | GGATCA |
| | | 270 . . . 275 | GATCAT |
| TN90 | 19GH749 | 264 . . . 274 | AGACGGGATCA (SEQ ID NO: 18) |
| | | 269 . . . 274 | GGATCA |
| | | 270 . . . 275 | GATCAT |
| TN90 | 19GH971 | 264 . . . 274 | AGACGGGATCA (SEQ ID NO: 18) |
| | | 269 . . . 274 | GGATCA |

TABLE 11A-continued

Exemplary mutant alleles obtained in the QPT2a gene

| Variety | Line | Position | Deleted sequence |
|---|---|---|---|
| TN90 | 19GH757 | 269 . . . 275 | GGATCAT |
| TN90 | 19GH972 | 270 . . . 275 | GATCAT |
| TN90 | 19GH973 | 268 . . . 276 | GGGATCATA |
| TN90 | 19GH750 | 268 . . . 275 | GGGATCAT |
| | | 269 . . . 275 | GGATCAT |
| TN90 | 19GH796 | 269 . . . 276 | GGATCATA |
| TN90 | 19GH975 | 269 . . . 276 | GGATCATA |
| TN90 | 19GH661 | 268 . . . 275 | GGGATCAT |
| | | 270 . . . 271 | GA |
| TN90 | 19GH662 | 268 . . . 275 | GGGATCAT |
| | | 270 . . . 271 | GA |
| TN90 | 19GH663 | 268 . . . 275 | GGGATCAT |
| | | 270 . . . 271 | GA |
| TN90 | 19GH974 | 269 . . . 273 | GGATC |
| TN90 | 19GH352 | 269 . . . 272 | GGAT |
| TN90 | 19GH353 | 269 . . . 272 | GGAT |
| TN90 | 19GH354 | 269 . . . 272 | GGAT |
| TN90 | 19GH797 | 269 . . . 272 | GGAT |
| TN90 | 19GH759 | 270 . . . 274 | GATCA |
| TN90 | 19GH798 | 270 . . . 274 | GATCA |
| TN90 | 19GH1025 | 270 . . . 274 | GATCA |
| TN90 | 19GH355 | 270 . . . 276 | GATCATA |
| TN90 | 19GH351 | 270 . . . 276 | GATCATA |
| TN90 | | 270 . . . 276 | GATCATA |
| K326 | 19GH744 | 268 . . . 274 | GGGATCA |
| K326 | 19GH746 | 270 . . . 274 | GATCA |

TABLE 11B

Exemplary mutant alleles obtained in the QPT2b gene

| Variety | Line | Position | Deleted sequence |
|---|---|---|---|
| TN90 | 19GH752 | 266 . . . 275 | ACGGGATCAT (SEQ ID NO: 19) |
| | | 268 . . . 275 | GGGATCAT |
| TN90 | 19GH753 | 266 . . . 275 | ACGGGATCAT (SEQ ID NO: 19) |
| | | 268 . . . 275 | GGGATCAT |

TABLE 11B-continued

Exemplary mutant alleles obtained in the QPT2b gene

| Vari-ety | Line | Position | Deleted sequence |
|---|---|---|---|
| TN90 | 19GH754 | 266 . . . 275 | ACGGGATCAT (SEQ ID NO: 19) |
| | | 268 . . . 275 | GGGATCAT |
| TN90 | 19GH755 | 269 . . . 276 | GGATCATA |
| | | 270 . . . 274 | GATCA |
| TN90 | 19GH749 | 269 . . . 276 | GGATCATA |
| | | 270 . . . 274 | GATCA |
| TN90 | 19GH971 | 269 . . . 276 | GGATCATA |
| | | 270 . . . 274 | GATCA |
| TN90 | 19GH757 | 269 . . . 275 | GGATCAT |
| TN90 | 19GH972 | 270 . . . 274 | GATCA |
| | | 274 . . . 275 | AT |
| TN90 | 19GH973 | 268 . . . 275 | GGGATCAT |
| | | 269 . . . 276 | GGATCATA |
| TN90 | 19GH750 | 269 . . . 276 | GGATCATA |
| | | 270 . . . 274 | GATCA |
| TN90 | 19GH796 | 269 . . . 275 | GGATCAT |
| TN90 | 19GH975 | 269 . . . 275 | GGATCAT |
| TN90 | 19GH661 | 266 . . . 274 | ACGGGATCA |
| | | 270 . . . 276 | GATCATA |
| TN90 | 19GH662 | 266 . . . 274 | ACGGGATCA |
| | | 270 . . . 276 | GATCATA |
| TN90 | 19GH663 | 270 . . . 276 | GATCATA |
| | | 266 . . . 274 | ACGGGATCA |
| TN90 | 19GH352 | 269 . . . 276 | GGATCATA |
| TN90 | 19GH353 | 269 . . . 276 | GGATCATA |
| TN90 | 19GH354 | 269 . . . 276 | GGATCATA |
| TN90 | 19GH797 | 269 . . . 276 | GGATCATA |
| TN90 | 19GH759 | 269 . . . 275 | GGATCAT |
| TN90 | 19GH798 | 269 . . . 275 | GGATCAT |
| TN90 | 19GH1025 | 269 . . . 275 | GGATCAT |
| TN90 | 19GH760 | 270 . . . 276 | GATCATA |
| TN90 | 19GH355 | 269 . . . 276 | GGATCATA |
| TN90 | 19GH351 | 269 . . . 276 | GGATCATA |
| TN90 | | 269 . . . 276 | GGATCATA |
| K326 | 19GH744 | 269 . . . 276 | GGATCATA |
| | | 270 . . . 276 | GATCATA |
| | | 266 . . . 276 | ACGGGATCATA |

TABLE 11B-continued

Exemplary mutant alleles obtained in the QPT2b gene

| Vari-ety | Line | Position | Deleted sequence |
|---|---|---|---|
| | | | (SEQ ID NO: 14) |
| K326 | 19GH746 | 269 . . . 288 | GGATCATAGCAGGGATTGCA (SEQ ID NO: 15) |
| | | 270 . . . 277 | GATCATAG |
| K326 | 19GH745 | 269 . . . 288 | GGATCATAGCAGGGATTGCA (SEQ ID NO: 16) |
| K326 | 19GH794 | 266 . . . 276 | ACGGGATCATA (SEQ ID NO: 17) |

Example 3: Alkaloid Analysis of QPT Edited Lines

Genome edited tobacco plants along with controls are grown in 10" pots in a greenhouse with 75 PPM fertilizer. At flowering stage, plants are topped and 2 weeks post topping lamina samples were collected from the third, fourth, and fifth leaves from the top of the plant, and alkaloid levels are measured using a method in accordance with CORESTA Method No 62, *Determination of Nicotine in Tobacco and Tobacco Products by Gas Chromatographic Analysis*, February 2005, and those defined in the Centers for Disease Control and Prevention's *Protocol for Analysis of Nicotine, Total Moisture and pH in Smokeless Tobacco Products*, as published in the Federal Register Vol. 64, No. 55 Mar. 23, 1999 (and as amended in Vol. 74, No. 4, Jan. 7, 2009).

Briefly, approximately 0.5 g of tobacco is extracted using liquid/liquid extraction into an organic solvent containing an internal standard and analyzed by gas chromatography (GC) with flame ionization detection (FID). Results can be reported as weight percent (Wt %) on either an as is or a dry weight basis. Reporting data on a dry weight basis requires an oven volatiles (OV) determination. Unless specified otherwise, total or individual alkaloid levels or nicotine levels shown herein are on a dry weight basis (e.g., percent total alkaloid or percent nicotine).

Plants are also planted in the field, harvested, and tested for alkaloids and TSNA levels in cured tobacco. Both leaf yield and leaf grade are also assessed for QPT edited plants. Further, different mutant combinations of individual QPT genes are generated and tested (e.g., single, double, triple, or quadruple).

Example 4: Obtaining Tobacco Lines with Edited Mutant Alleles in One or More QPT Genes Tobacco lines with mutations in individual QPT genes or selected combinations of QPT genes are obtained from the tobacco lines listed in Tables 10A and 10B. Crossing a single, double, triple, or quadruple mutant (having mutations in one, two, three, or four QPT genes, respectively) to a non-mutated control line and selecting segregating progeny plants for specific QPT mutation combinations. Each mutated gene can be either homozygous or heterozygous for the mutation. Exemplary individual qpt mutant alleles are listed in Tables 11A and 11B.

Example 5: Further Reduction of Total Alkaloids by Combining qpt Mutations with Mutations in Other Genes To further reduce total alkaloids and/or selected individual alkaloids, qpt mutants are combined with mutations in additional genes related to alkaloid biosynthesis in tobacco, such as a quintuple pint mutant or quinolinate synthase (QS). Briefly, gene editing is used to mutate select pmt or QS genes in a desired mutant background. In the resulting combined pmt/pmt or qs/pmt mutants, alkaloids and TSNA levels are tested in cured tobacco. Both leaf yield and leaf grade are also assessed.

---

The invention claimed is:

1. A tobacco plant, or part thereof, comprising:

(a) a first non-naturally occurring mutant allele of an endogenous QUINOLINATE PHOSPHORIBOSYL TRANSFERASE (QPT) 2a gene, the endogenous OPT2a gene having the nucleic acid sequence of SEQ ID NO: 7, wherein the first non-naturally occurring mutant allele comprises a first deletion as compared to the endogenous OPT2a gene, and wherein the first deletion either a deletion of nucleotide positions 264 to 274 as compared to the nucleic acid sequence of SEQ ID NO: 7 or a deletion of nucleotide positions 268 to 274 as compared to the nucleic acid sequence of SEQ ID NO: 7, and (b) a second non-naturally occurring mutant allele of an endogenous QPT2b gene, the endogenous OPT2b gene having the nucleic acid sequence of SEQ ID NO: 8, wherein the second non-naturally occurring mutant allele comprises a second deletion as compared to the endogenous OPT2b gene, and wherein the second deletion consists of a deletion of nucleotide positions 269 to 276 as compared to the nucleic acid sequence of SEQ ID NO: 8.

2. The tobacco plant, or part thereof, of claim 1, wherein the part thereof is a leaf.

3. A population of the tobacco plant of claim 1.

4. Cured tobacco material from the tobacco plant, or part thereof, of claim 1.

5. The cured tobacco material of claim 4, wherein the cured tobacco material is selected from the group consisting of flue-cured tobacco material, air-cured tobacco material, fire-cured tobacco material, and sun-cured tobacco material.

6. A tobacco blend comprising the cured tobacco material of claim 4.

7. The tobacco blend of claim 6, wherein the cured tobacco material constitutes at least 10% of cured tobacco in the tobacco blend by weight.

8. The tobacco blend of claim 6, wherein the cured tobacco material constitutes at least 10% of cured tobacco in the tobacco blend by volume.

9. A tobacco product comprising the cured tobacco material of claim 4 or 5.

10. The tobacco product of claim 9, wherein the tobacco product is selected from the group consisting of a cigarette, a cigarillo, a non-ventilated recess filter cigarette, a vented recess filter cigarette, a cigar, snuff, pipe tobacco, cigar tobacco, cigarette tobacco, chewing tobacco, leaf tobacco, shredded tobacco, and cut tobacco.

11. The tobacco product of claim 9, wherein the tobacco product is a smokeless tobacco product.

12. The tobacco product of claim 11, wherein the smokeless tobacco product is selected from the group consisting of loose leaf chewing tobacco, plug chewing tobacco, moist snuff, and nasal snuff.

13. A reconstituted tobacco comprising the cured tobacco material of claim 4.

14. The tobacco plant, or part thereof, of claim 1, wherein the tobacco plant is of a tobacco type selected from the group consisting of Burley tobacco, Maryland tobacco, and dark tobacco.

15. The tobacco plant, or part thereof, of claim 1, wherein the tobacco plant is from a tobacco type selected from the group consisting of flue-cured tobacco, dark air-cured tobacco, dark fire-cured tobacco, Galpão tobacco, and Oriental tobacco.

16. The tobacco plant, or part thereof, of claim 1, wherein the tobacco plant is of a tobacco variety selected from the group consisting of 400 (TC 225), 401 (TC 226), 401 Cherry Red (TC 227), 401 Cherry Red Free (TC 228), Cash (TC 250), Cash (TI 278), CC 101, CC 1063, CC 13, CC 143, CC 200, CC 27, CC 301, CC 33, CC 35, CC 37, CC 400, CC 500, CC 600, CC 65, CC 67, CC 700, CC 800, CC 900, Coker 139 (TC 259), Coker 139 yb1, yb2, Coker 140 (TC 260), Coker 176 (TC 262), Coker 187 (TC 263), Coker 187-Hicks (TC 265), Coker 209 (TC 267), Coker 258 (TC 270), Coker 298 (TC 272), Coker 316 (TC 273), Coker 319 (TC 274), Coker 347 (TC 275), Coker 371-Gold (TC 276), Coker 411 (TC 277), Coker 48 (TC 253), Coker 51 (TC 254), Coker 86 (TC 256), CU 263 (TC 619), CU 561, DH95-1562-1, Dixie Bright 101 (TC 290), Dixie Bright 102 (TC 291), Dixie Bright 244 (TC 292), Dixie Bright 27 (TC 288), Dixie Bright 28 (TC 289), GF 157, GF 318, GL 26H, GL 338, GL 350, GL 368, GL 395, GL 600, GL 737, GL 939, GL 939 (TC 628), Hicks (TC 310), Hicks Broadleaf (TC 311), K 149 (TC 568), K 317, K 326, K 326 (TC 319), K 340 (TC 320), K 346, K 346 (TC 569), K 358, K 394 (TC 321), K 399, K 399 (TC 322), K 730, Lonibow (TI 1573), Lonibow (TI 1613), McNair 10 (TC 330), McNair 135 (TC 337), McNair 30 (TC 334), McNair 373 (TC 338), McNair 944 (TC 339), MK94 (TI 1512), MS K 326, MS NC 71, MS NC 72, NC 100, NC 102, NC 1071 (TC 364), NC 1125-2, NC 12 (TC 346), NC 1226, NC 196, NC 2326 (TC 365), NC 27 NF (TC 349), NC 291, NC 297, NC 299, NC 37 NF (TC 350), NC 471, NC 55, NC 567 (TC 362), NC 60 (TC 352), NC 606, NC 6140, NC 71, NC 72, NC 729 (TC 557), NC 810 (TC 659), NC 82 (TC 356), NC 8640, NC 89 (TC 359), NC 92, NC 925, NC 95 (TC 360), NC 98 (TC 361), NC EX 24, NC PY 10 (TC 367), NC TG 61, Oxford 1 (TC 369), Oxford 1-181 (TC 370), Oxford 2 (TC 371), Oxford 207 (TC 632), Oxford 26 (TC 373), Oxford 3 (TC 372), Oxford 414 NF, PD 611 (TC 387), PVH 03, PVH 09, PVH 1118, PVH 1452, PVH 1600, PVH 2110, PVH 2275, R 83 (Line 256-1) (TI 1400), Reams 134, Reams 158, Reams 713, Reams 744, Reams M1, RG 11 (TC 600), RG 13 (TC 601), RG 17 (TC 627), RG 22 (TC 584), RG 8 (TC 585), RG 81 (TC 618), RG H51, RG4H 217, RGH 12, RGH 4, RGH 51, RGH 61, SC 58 (TC 400), SC 72 (TC 403), Sp. G-168, SPEIGHT 168, Speight 168 (TC 633), Speight 172 (TC 634), Speight 178, Speight 179, Speight 190, Speight 196, SPEIGHT 220, SPEIGHT 225, SPEIGHT 227, SPEIGHT 236, Speight G-10 (TC 416), Speight G-102, Speight G-108, Speight G-111, Speight G-117, Speight G-126, Speight G-15 (TC 418), Speight G-23, Speight G-28 (TC 420), Speight G-33, Speight G-41, Speight G-5, Speight G-52, Speight G-58, Speight G-70, Speight G-70 (TC 426), Speight G-80 (TC 427), Speight NF3 (TC 629), STNCB, VA 182, VA 45 (TC 559), Vesta 30 (TC 439), Vesta 33 (TC 440), Vesta 5 (TC 438), Vesta 62 (TC 441), Virginia (TI 220), Virginia (TI 273), Virginia (TI 877), Virginia 115 (TC 444), Virginia 21 (TC 443), Virginia Bright (TI 964), Virginia Bright Leaf (TC 446), Virginia Gold (TC 447), White Stem Orinoco (TC 451), 4407 LC, AA-37-1, Burley 21 (TC 7), Burley 49 (TC 10), Burley 64 (TC 11), Burley Mammoth KY 16 (TC 12), Clay 402, Clay 403, Clay 502, Clays 403, GR 10 (TC 19), GR 10 (TC 19), GR 10A (TC 20), GR 13 (TC 21), GR 14 (TC 22), GR 149 LC, GR 153, GR 17 (TC 23), GR 17B (TC 24), GR 18 (TC 25), GR 19 (TC 26), GR 2 (TC 15), GR 24 (TC 27), GR 36 (TC 28), GR 38 (TC 29), GR 38A (TC 30), GR 40 (TC 31), GR 42 (TC 32), GR 42C (TC 33), GR 43 (TC 34), GR 44 (TC 35), GR 45 (TC 36), GR 46 (TC 37), GR 48 (TC 38), GR 5 (TC 16), GR 53 (TC 39), GR 6 (TC 17), GR 9 (TC 18), GR139 NS, GR139 S, HB 04P, HB 04P LC, HB 3307P LC, HB 4108P, HB 4151P, HB 4192P, HB 4194P, HB 4196, HB 4488, HB 4488P, HB04P, HB 4488 LC, HIB 21, HPB 21, HY 403, Hybrid 403 LC, Hybrid 404 LC, Hybrid 501 LC, KDH-959 (TC 576), KDH-960 (TC 577), KT 200 LC, KT 204 LC, KT 206 LC, KT 209 LC, KT 210 LC, KT 212 LC, KT 215 LC, KY 1 (TC 52), KY 10 (TC 55), KY 12 (TC 56), KY 14 (TC 57), KY 14 x L8 LC, KY 15 (TC 58), KY 16 (TC 59), KY 17 (TC 60), KY 19 (TC 61), KY 21 (TC 62), KY 22 (TC 63), KY 24 (TC 64), KY 26 (TC 65), KY 33 (TC 66), KY 34 (TC 67), KY 35 (TC 68), KY 41A (TC 69), KY 5 (TC 53), KY 52 (TC 70), KY 54 (TC 71), KY 56 (TC 72), KY 56 (TC 72), KY 57 (TC 73), KY 58 (TC 74), KY 8654 (TC 77), KY 8959, KY 9 (TC 54), KY 907 LC, KY 908 (TC 630), NBH 98 (Screened), NC 1206, NC 129, NC 2000 LC, NC 2002 LC, NC 3 LC, NC 5 LC, NC 6 LC, NC 7 LC, NC BH 129 LC, NC03-42-2, Newton 98, R 610 LC, R 630 LC, R 7-11, R 7-12 LC, RG 17, TKF 1801 LC, TKF 2002 LC, TKF 4024 LC, TKF 4028 LC, TKF 6400 LC, TKF 7002 LC, TKS 2002 LC, TN 86 (TC 82), TN 90 LC, TN 97 Hybrid LC, TN 97 LC, VA 116, VA 119, Virgin A Mutante (TI 1406), Virginia 509 (TC 84), Maryland 10 (TC 498), Maryland 14 D2 (TC 499), Maryland 201 (TC 503), Maryland 21 (TC 500), Maryland 341 (TC 504), Maryland 40, Maryland 402, Maryland 59 (TC 501), Maryland 601, Maryland 609 (TC 505), Maryland 64 (TC 502), Maryland 872 (TC 506), Maryland Mammoth (TC 507), Black Mammoth (TC 461), Black Mammoth Small Stalk (TC 641), Certified Madole (TC 463), D-534-A-1 (TC 464), DAC ULT 302, DAC ULT 303, DAC ULT 306, DAC ULT 308, DAC ULT 312, DF 300 (TC 465), DF 485 (TC 466), DF 516 (TC 467), DF 911 (TC 468), DT 508, DT 518 (Screened), DT 538 LC, DT 592, Improved Madole (TC 471), Jernigan's Madole (TC 472), KT 14LC, KT D17LC, KT D4 LC, KT D6 LC, KT D8 LC, KY 153 (TC 216), KY 157 (TC 217), KY 160, KY 160 (TC 218), KY 163 (TC 219), KY 165 (TC 220), KY 170 (TC 474), KY 171 (PhPh), KY 171 (TC 475), KY 171 LC, KY 171 NS, KY 180 (TC 573), KY 190 (TC 574), Little Crittenden, Little Crittenden (TC 476), Little Crittenden LC (certified), Little Crittenden PhPh, Lizard Tail Turtle Foot, Madole (TC 478), Madole (TC 479), MS KY 171, MS NL Madole LC, MS TN D950 LC, Nance (TC 616), Narrow Leaf Madole LC (certified), Neal Smith Madole (TC 646), Newtons VH Madole, NL Madole, NL Madole (PhPh), NL Madole (TC 484), NL Madole LC, NL Madole LC (PhPh), NL Madole NS, One Sucker (TC 224), OS 400, PD 302H, PD 312H, PD 318H, PD 7302 LC, PD 7305, PD 7309 LC, PD 7312 LC, PD 7318 LC, PD 7319 LC, Petico M PG04, PY KY 160 (TC 612), PY KY 171 (TC 613), Shirey, TI 1372, TN D94, TN D94 (TC 621), TN D950, TN D950 (PhPh), TN D950, TN D950 (TC 622), TR Madole (TC 486), VA 309, VA 309 (TC 560), VA 309 LC (certified), VA 310 (TC 487), VA 331 (TC 592), VA 355 (TC 638), VA 359, VA 359 (Screened), VA 359 (TC 639), VA 359 LC (certified), VA 403 (TC 580), VA 405 (TC 581), VA 409 (TC 562), VA 510 (TC 572), Bafra (TI 1641), Bahce (TI 1730), Bahia (TI 1416), Bahia (TI 1455), Baiano (TI 128), Basma, Basma (TI 1666), Basma Drama, Basma Hybrid (PhPh), Basma Zihna I, Bitlis (TI 1667), Bitlis (TI 1725), Bubalovac (TI 1282), Bursa (TI 1650), Bursa (TI 1668), Canik (TI 1644), Djebel 174 (TI 1492), Djebel 359 (TI 1493), Djebel 81, Dubec 566 (TI 1409), Dubec 7 (TI 1410), Dubek 566 (TI 1567), Duzce (TI 1670), Edirne (TI 1671), Ege (TI 1642), Ege-64 (TI 1672), Izmir (Akhisar) (TI 1729), Izmir (Gavurkoy) (TI 1727), Izmir Ege 64, Izmir-Incekara (TI 1674), Izmir-Ozbas (TI 1675), Jaka Dzebel (TI 1326), Kaba-Kulak, Kagoshima Maruba (TI 158), Katerini, Katerini S53, Krumovgrad 58, MS Basma, MS Katerini S53, Nevrokop 1146, Ozbas (TI 1645), Perustitza (TI 980), Prilep (TI 1291), Prilep (TI 1325), Prilep 12-2/1, Prilep 23, Samsun (TC 536), Samsun 959 (TI 1570), Samsun Evkaf (TI 1723), Samsun Holmes NN (TC 540), Samsun Maden (TI 1647), Samsun NO 15 (TC 541), Samsun-BLK SHK Tol (TC 542), Samsun-Canik (TI 1678), Samsun-Maden (TI 1679), Saribaptar 407-Izmir Region, Smyrna (TC 543), Smyrna No. 23 (TC 545), Smyrna No. 9 (TC 544), Smyrna-Blk Shk Tol (TC 546), Trabzon (TI 1649), Trabzon (TI 1682), Trapezund 161 (TI 1407), Turkish (TC 548), Turkish Angshit (TI 90), Turkish Samsum (TI 92), Turkish Tropizoid (TI 93), Turkish Varotic (TI 89), Xanthi (TI 1662), Bahai (TI 62), Beinhart 1000, Beinhart 1000 (TI 1562), Beinhart 1000-1 (TI 1561), Bergerac C, Bergerac C (TI 1529), Big Cuban (TI 1565), Castillo Negro, Blanco, Pina (TI 448), Castillo Negro, Blanco, Pina (TI 448A), Castillo Negro, Blanco, Pina (TI 449), Caujaro (TI 893), Chocoa (TI 289), Chocoa (TI 313), Connecticut 15 (TC 183), Connecticut Broadleaf, Connecticut Broadleaf (TC 186), Connecticut Shade (TC 188), Criollo Colorado (TI 1093), Enshu (TI 1586), Florida 301, Florida 301 (TC 195), PA Broadleaf (TC 119), Pennsylvania Broadleaf, Pennsylvania Broadleaf (TC 119), Petite Havana SR1, Petite Havana SR1 (TC 105), Chocoa (TI 319), Hoja Parada (TI 1089), Hoja Parado (Galpoa) (TI 1068), Perique (St. James Parrish), Perique (TC 556), Perique (TI 1374), Sylvestris (TI 984), and TI 179.

17. The tobacco plant, or part thereof, of claim 1, wherein the tobacco plant or part thereof is homozygous for both the first non-naturally occurring mutant allele and the second non-naturally occurring mutant allele.

18. A tobacco seed from the tobacco plant of claim 1, wherein the tobacco seed comprises the first non-naturally occurring mutant allele and the second non-naturally occurring mutant allele.

19. The tobacco plant, or part thereof, of claim 1, wherein the tobacco plant is a male sterile tobacco plant.

* * * * *

SEQUENCE LISTING

```
<160> NUMBER OF SEQ ID NOS: 19

<210> SEQ ID NO 1
<211> LENGTH: 6749
<212> TYPE: DNA
<213> ORGANISM: Nicotiana tabacum

<400> SEQUENCE: 1
cctggtaagt cgaactctta gtctttataa tttgcaggag caactctcat aagttatata      60
cgattaaacg ataacaaacg ttataattta gaaaagaaat gccttattta tttttataca     120
tttatttatt tatcaccgtt gttattgatc ttttgtctct gaaccgatat tttctgaaaa     180
cagtctctct atccctccgg gttatggata gagtatgcgt acgttctacc atctcaaacc     240
ccaagattat taatggattg ttattgttgt acatttattt atttatttat ctgcctatca     300
aatgttgtat cctgtttctt taatttgata tattctgaaa ggcatatgtt aattgttcgc     360
aaaatcagga aaagggaagt gaaaaataac ctattgtggt caccctgtta aaccatatag     420
accaaaacaa ccacaaattc acataattgg aggactattt tgttaaaaca aaagtcttca     480
cagaaagcat taagctccgc aaaagctatt tgctacaaaa ttccttgcat accccaaaat     540
ttcaatgttt aaagttcttc ctttcactgc aatagtccac cctaatgcaa ttacagctcc     600
aaggtttctt taaaacccct caatttaacc cagaagcaac aacaaaaaaa aggattcttg     660
aaaatcatgt ttttattttt gttatatact gataaagatt gttctttat gcaattacag      720 ctccaaggtt tctttaaaac cactcaattc cacccaggaa aaaaaagtct tgaacatcat     780 gttttttattg ttttatactg ataaagatta ttcctttatg agtttctgat taaaatttgt     840
ttgtaaattg cagattggtt gtgaaaatgt cagcaatagc caccaaaaat gcagtggagt     900
catttgtagt gaagccacca gcacacccaa cttatgattt aaagggtgtt attcaacttg     960
ccctctctga agatgctggg gatataggtt tggtttttagc ttatattgtt tttttaatctt    1020 atgtttgtca aatgggtttc aataagtttt tatacgtggg gaaatgctgt taaagaaaac    1080
taatggtaaa cgttttaatt aattgggagg tgctttatga agtttagcta tagtctattt    1140 ttttttttgtg aactccaagc ttcattcttt cttgtgtagc ctcaattagt tagagctaat    1200
tgtgttcttt ttcgataagg acagctaatg tgttcttaat aagtattatc ttcagtttaa    1260
ggaaagagga gggggagga atagttctgc caaaagttgc tttctttctt gttttccatc     1320
cgctgtgagg cccaactaat ccagattcgc gctaggaagt cccacgttga ggtaaaggtg    1380
acttcattct caggcttgaa cgttggacct cttgttaagg attgacgtat cgccccacca    1440
caacctttgg cgttaaaagt ttttttttttt aagttcaata tcaggaggat actgtcatgt    1500
actgtctgac tctctgcgtg atggaaaagt ttgtttgagt aaatttcttg gaactagcaa    1560
tattttcagc acctagctac cattgtgaat ttgagtactc aattatacaa aaaccaattt    1620
ttcctatgta ttatttgtgt gaaatgcagg agatgtgact tgtaaggcga caattcctat    1680
tgacatggaa tccgaagctc attttctagc aaaggaagac gggattgtag caggaattgc    1740
acttgctgag atgatattcg cagaggttga tccttcacta aaggtattga ttttttcaat    1800
```

-continued

```
taggttgttc tggtaaccgg tatttctact ttgaagaaat gtctgaaaaa agggtttttt    1860
aatttcttca tgttctcatt atcagatgga gtggtctata aatgatggcg ataaagttca    1920
taaaggcttg aaattcggca aagtacaagg taaactatat gtgagaaatg atgaattgct    1980
aatgattctt tgacttaata ataatcttgc cttaacgttt gtaggaaagg ctcacagcat    2040
tgttatagct gagagagttg ttctcaattt tatgcaaagg atgagcggaa ttgctacact    2100
aactaaggtg tgtttgtcct catgtaagta gctcatcatt aataaagatc tggaaagata    2160
ttgcaatgaa tggaaatggt tattgtcatt gatgtgttgg ttccagtatt ccaaagttaa    2220
gtcaagcgta ctagatctgt gactggtcaa ttgttctatg tccgaaatta ctgaattttg    2280
ttgcagaaca tatgtgttga tccaaattta cacattcctg tatgaattat gatatataaa    2340
atcaatgaaa tatccttcaa cgtttcgagt acaatagtcc agagtgcaag tcttggaaac    2400
agattccctg tactctttat aaggctgtgt acgtccgctc ttctgatacg ttagatggtg    2460
tgagagccac acactgaaaa caattctgca atcagtctat gacaaagatt cctcagttta    2520
atccagtgtt gcgcggactc tcaaaaatga tgccgcaccc gtgtcggatc ctccaaaaat    2580
acactttttt ggaggatccg acacgcaccc aataacattt tcggagagtc cgagaaacat    2640
aggtttaatc catcacaaac aataggtgca aatgcacatg caaagacgta actatacaca    2700
tgccattttc tagaactcag tagatgagaa taaattaacg aatgaatgtt aacttaaatt    2760
ataaagtacc aacaaaattt gtaactaata agaacggttc aaatattcac ccggaaatga    2820
aataatgtgt gaaatctaaa cagaattgtt gttggaattt gcaaaaggag ctgtgagttt    2880
tgatactttg ggtacaacta cttgcgttta cctttcaatg gatccccttt ggttctctaa    2940
atcaggtaac aaatatcaaa tatttgtcca caaaaattaa ttccatgtgt tccttttttca    3000 ggatatcgac actgctgctg gtgtcatgtt ttaaagaat atgaaaaatt tcattgaacc    3060
aaaaacaaaa tatcttcgtc tctctaatga aagacaatct agatgttttg tacctgataa    3120
tgctatttca agatgtcatg gagttcattg tcttgcctct gtattaatga ttagaattta    3180
gaagagagtg attttttttaa tatttgcagg cgatggcaga tgctgctcac cctgctacca    3240
tcttggagac taggaaaact gctccaggat tacgtttggt ggataaatgg gcggtaaata    3300
tttactcgcc aaaatcatcc attgtgaaag gctatcacat gtatatatag tttatcttgg    3360
ctgactttct acctggcttt aagtgaaggt attaatcggt gggggaaga atcacagaat    3420 gggcttattt gatatggtaa tgataaaga taatcacata tctgctgctg gaggtgtcag    3480
caaagctcta aattccgtgg atcagtattt ggaacaaaat aaacttcaga tgggggttga    3540
ggttggccac atataccttt ggattaaatt gttcgatatg gttatagttt gcgcatatga    3600
tatgtttgtt tcgacctgac agttcaatta cctattctgc tggaatatat taatcattta    3660
atcttagctt ctgccatcag ttgtgcaata ctcttttgtc aattttgtat tttgtcagat    3720
aaacattttt ctagagccat ttcaatcata aactatttat attgttgata atataaactt    3780
tatgattgat gctatttctg atatcctttc actgaagaac tgaattctta tctgttgaaa    3840
tcaaatgtta gttcaagttc agagatgttt gccctacacc tcaagacttt tattttacat    3900
ttttgtatct agatacactt taggggttga gagtagtatc ccaaaatata tcatgatttc    3960
ggataactga aacaagagtg gaaaattgtt ttatttgacc atgttaaagc agttagcgaa    4020
caaaatagtt tgtcaggtta cattttggac tagttttcga ggtcatgttt tttggatttc    4080
ggcacacaac aatgtacatg ggttccactc ccttggatat tctttcttga taatgttttg    4140
cttttgttac aaaagtaaag ggaaaagtaa aaataacatt atatattgct gaaaaaaccg    4200
```

```
ggaaaatttc tgctttcggg aattttttcaa tgttatcatc caccctaata taacctaaga   4260
ggtttgggag aaactgtatt tttggtctgt ctttgcataa cacttaatag tgttgtcatt   4320
aagttggtaa tttgcaccta ctttggatag ttaagaagac taattatgta gatacttttt   4380
ttttataagg caaaatctta taaatgtgtc accatcaaga atatgctggt aggaacccaa   4440
cttacgttat tgtatttagc agttttgagc gtatggtcct ttctgaatgt gctcaatatc   4500
tggtaattat tgtcagagtt ttaaaccttt tctcttatcc aacaggttga aaccaggaca   4560
attgcagaag tacatgaggt tctagaatat gcatctcaaa caaagacttc gttgactagg   4620
ataatgcttg ataatatggt tgttccatta tctaacggag atattgaggt atccatgctt   4680
gaggaggctg tagatttgat caatgggagg tttgagacag aggtacttct ggtttcattt   4740
aaaattttta ctgctccaca aactgtcagt atatacgaag cttagaaata gcatttaaga   4800
tttgatttta tgaaaaaaac tcctaactca taaaaaaaga tactgcgcgg tttcagaggc   4860
gaatccagga tttaatgctt atggtttcct gcaacaatct cgagtaaatt ttcaataata   4920
actgagttca cattcaaaca tttatagata tttagtaaat tttcgaacac atttacactg   4980
tttggacaaa atctactaga ttcacttgaa cccttaggtc gggaggtgga tccgcccctt   5040
cttggtttcc cgtttattat ttttgtcagc ggatatcttg tgatgacatg ctttgtttgc   5100
tgtaatggtg gcaggcttca ggaaatgtta cccttgaaac agtgcacaag attggacaaa   5160
ctggtgttac ctacatttct aggtatgtat ttcgctcttg ctattttta dacaagaggg    5220 gttgctctga tgataagcaa cctccacttt caaccaagag gttgtgagtt cgagtcaccc   5280
caagagcaag gtggggagtt cttggaggga aggatgtcga gggtctattg gaaacagcct   5340
ctctacctca tggtaggggt aaggtctgcg tacacactac cctccctaga ccccactagt   5400
gggattatac tgggttgttg ttgttatttt ttcagaagat cttcattaaa gaaattggaa   5460
gataataaaa atagaataga cttctcattg tgtgttattt gtattgctgg gacgtctttc   5520
ttttcctctt tttttatact aataagatgg ttagtttact cgcacacatc agacaaaagc   5580
tcccattaga tggtctatgt tatgcataat tttcttgata aaattgataa acaggagaac   5640
ttacatggat tgctaaagta caacaacaac tataaaccta gtgtaatccc acaagtaggg   5700
tatggggaag gtagtgtgta cgcagacctt actttcatct tgaaggtaga gaggtggttt   5760
tcgatagacc ctcggctcac gaaagacgag aagaaaagca atagcaccaa gcaataacca   5820
ataagatagt aagagaacga aacgaaagga acaagtaata ctaaaaaaat ctaacaaaaa   5880
tagaatatag gactaatact ctcgacgacc tacttaccgt ctaccttgat tcttgagctt   5940
cacacattcc tatcaagggt catgtcctct gtaagttgta gtaaagtcat atcctgccta   6000
atcacctctc ctctatactt cttcggccaa tctctacctc ttctcagccc ctttagcttc   6060
aacctctcac acctccttac atggattgct aaagtgctga caattaggtt gttgacctct   6120
tcggttattt ataagttaac aaaggcttta cttttaagca catgatttag tgtggggtac   6180
aatttcctcg ctaggagtgg actcaatact tgagaaagtt caatatatgt ttgtttcatc   6240
cactaatgat acccttttgtc agatattagc ctgttatttt gataaaaacg aatctatctt   6300
ttgtttggtc catatgtatt aggcacctga aggttttgtt atgatactta tagtatgaat   6360
atttgcagtg gtgcactaac gcattctgtg aaagcacttg acatttccct gaagatcgat   6420
acagagctcg cccttgaagt cggacgacgt acaaaacgag catgaccgcc attacttttg   6480
ttgtagggtt ggagtaaaag cagctgaatg gcacaaagtg caaataagaa ttattttact   6540
```

```
agttgtcaaa caaataagat gtaagttgct ggaataattc ggtggctctt ttacaaccta    6600
attgcttgag ttgatatttc attatagctt tgctttcatg ttttggtgtg tgtgaagttc    6660
tgtgttactt caaatctttt atggctctct tccaacctac ctacctctga atattttggt    6720
gcactacttt gtaaaggaaa cagcaaagt                                       6749

<210> SEQ ID NO 2
<211> LENGTH: 6607
<212> TYPE: DNA
<213> ORGANISM: Nicotiana tabacum

<400> SEQUENCE: 2
tttttgctat ttttagtata tttttctttt gtctttagta caattttttt tcttcgcttt      60
ttaggatttg atagaccttt cctaaggtta aatctttttt tatcataata ctcatcaaat     120
ctaagagaca cagagctcat taatagcccg tttggccaag ctgcaaaaat cagcttattt     180
tgataagtgc ttttttttcaa aagtactttt gatgagaagc agtttgtgtt tggctaatta     240
gtttaaaaag cacttctgag tagcaattag tgtttcgcca agctttaaaa aactgtttct     300
aagtgtattt ctcaaaagtg cttctcaaaa aagtaatttt ggagagaagc tactttttt     360 ctgcttctcc aaaattattt ttttccttcc agaagcttgg ccaaacacct caatttttgg     420
ccaaaagtac ttttggcaaa aaaaaaaaag aactttggc caaaaataag cttggccaaa     480
ttttaggacc aaaagtattc agagtatact taagggacta ctttgaactt atcctcaaac     540
ataagggact atatttgtca ttttctcgaa gttctcacaa cccaagaaac cactaagctc     600
agcaaagcta tttgctccaa aaatcaaaat ttcaatgttt aaagtttttc ctttcactgc     660
aatagtgcac cctcatgcaa ttacagcacc aaggtttctt tagaacccct caatttaacc     720
cagaagcaaa aaaaaaaaaa aggattcttg aaaatcatgt tttatttttt gttatatata     780
ctgataaaga ttgttctttt atgcaattac agctcccaat gtttctttaa aaccactcaa     840
ttccacccag aaaggaaaaa aaagattct tgaaaatcat gttcttattg ttttgtactg     900
ataaagatta ttcctttatg agtttctgat taaattttgt ctgtaaattg caggttggtt     960
gtgaaaatgt cagcaatagc caccaaaaat gcagtggagt cattagtagt gaagccacca    1020
gcacacccaa cttatgattt aaagggtgtt attcaacttg ccctctctga agatgctggg    1080
gatttaggtt tggttttagc tcatattatt ttaatcttat tatattgtca aatgaggtgc    1140
actcagtttc aatactttag taaatactgt taagggaagc taatggtaga cttttttaatt    1200 aattgggagt agctttatga agtttagcta tagtcttttt ttgttttgtg tgaactccaa    1260
gcttcaattt ttcttgtgta gcctcaatta atttatagct aattgtgttc ttttttccata    1320 agaacagcta atgtgttctt aataaggatt atcttcagtt taaccggggg gggggggggg    1380
ggaggagaat agttctgcca aaagttgttt tcctttcttg tttcccacct ggtgtccggt    1440
acccgctttg tggcccaact aatccggaga actcttgtta aggattgagg agtatgtatc    1500
gccccaccgc aacctttggt gtcaatagtt gttttttttaa gttcaagagc ccgaggatat    1560
tgtcatgtac tgtctgactc tctgcgtgat ggaaaagttt gtttgagtaa atttcttggt    1620
actagcaata ttttcagcac ctagctacca ttgtgaattt gagtactcaa ttataaaaaa    1680
ccaatttgtc ctgtgtatta tttgtgtgaa atgcaggaga tgtgacttgt aaggcaacaa    1740
ttcctattga catggaatcc gaagctcatt ttctagcaaa ggaagacggg attgtagcag    1800
gaattgcact tgctgagatg atattcgcag aggttgatcc ttcactaaag gtattgatttt    1860 tttcaattag gttgttctgg taaccggtat ttctactttg aagaaatgtc tgaaaaaagg    1920
```

-continued

```
ttttttaatt tcttcatgtt ctcattatca gatggagtgg tctataaatg atggtgataa    1980
agttcataaa ggcttgaaat tcggcaaagt acaaggtaaa ctatatgtga gaaatgatga    2040
attactaatg attttttgaa ttaataataa tcttgccttg acgtctgcag gaaaggctca    2100
cagcattgtt atagctgaga gagttgttct caatttcatg caaagaatga gcggaatagc    2160
tacactaact aaggtgtgtt tgtcctcatg taagtagcac atcattaata aagatctgga    2220
aagatagcaa tgaatgcaaa tggttatgtc attgatgagt tggtttcagt attccaaagt    2280
taagtcaagc gtaccagatc tgagactgtc aattgttcta tgcccgaaat tactggattt    2340
tgttgcagaa catatgcatt gatctaaatt tacacattcc tgtatgatat ataaaatcaa    2400
tgaaatatcc ttcaacggtt caagtacaat ggtcaagagt tcaagtctta gaaacagatt    2460
ccgcgtattc tttataaggc tgtgtacgtc cactcttctg atacattaga tggtgtgaga    2520
gccgcacact gaaaacaatt ctgcaatcag tctatgacaa agattcctca gtttattcca    2580
tcacaaacaa aaggtgcaaa tgcacatgca aagacttaac tatacacatg ccattttcta    2640
aaactcagta gacgagaata aattaactaa tgaatgttaa cataaattat gaagtaccaa    2700
caaaatttgt aactaataag aacggtacaa atattcaccc ggaatgaaat aatgtgtgaa    2760
atctaaacag atattgctgt tagaatttgc aaacggagct gtgagttttg acacttttgg    2820
tacaactact tgcgtttacc tttcaatgga accccttttgg ttctctaaat caggtaataa    2880
atatcaaata tctgtccaca aaaattaatt ccatgtgttc cttttttcagg atatggacac    2940 tgctgcaggt gtcatgtttt aaaagaattt gaaagatttc attgaaccag aaccaaacat    3000
cttcatctct ttaatgaata gacaaactag acattttgta cctgataatg ctatctcaag    3060
atgtcatgga gttcattgtc ttgcctctgt agtaatgatt agaatttaga agagagtgag    3120
ttctttaata tttgcaggcg atggcagatg ctgcacaccc tgctaccatc ttggagacta    3180
ggaaaactgc tccaggatta cgtttggtgg ataaatgggc ggtaaatatt tactcgccaa    3240
aatcatccat tgtgagaggc tatcacatgt atatatagtt catcttggct gactttctac    3300
ctggctttaa gtgaaggtat tgatcggtgg ggggaagaat cacagaatgg gcttatttga    3360
tatggtaatg ataaaagata atcacatatc tgctgctgga ggtgtcagca aagctctaaa    3420
ttccgtggat cagtatttgg aacaaaataa actccagatg ggggttgagg ttggccccat    3480
ttacctttgg attaaattgt gtggttatag ttatgtttat ttcaacctga cagttcaatt    3540
acctattctg ctggaataga ttaatcattt aatcttagct tctgccatca gttgtgcaat    3600
actcttttgt cagtttttgta tttggtcaga taaatatctt tctagagcta ttttcaatca    3660
aaaactattt atagtgttga tgatataaac tttataattg atgctatttc tgatatcctt    3720
tcattgaaga attgaattct tatctgttga aatcaaatgt tagtccaagt tcagagatgt    3780
ttgcactaca cctcgagact tttatttttac atttttgtat ctagatacac ttgtaggggt    3840
tgagagcaac aacaacaaac ccagtataat cccacaagtg gggtctggtg agggtggtgt    3900
atacgcagac cttgaagcta gagaggctgt tttcgaaaga cccccagcgt agaggttgag    3960
agtagtatcc cagaatatat catgattttt gataactgaa acaagagtgg aaaattgtgt    4020
tatttgacca tgttaaagca gttagcgaac aaaatagttt gtcaggttac attttggact    4080
agttttcaag gtcatctttt ttggatttcg gcacacaaca atgttcatgg ttccactccc    4140
ttgggtattc tttcttgata atgttttgct tttgttacaa aagtaaaggg aaaagtaaaa    4200
ataacattat atattgctga aagagctggg aaaatttctt cttccaggaa ttttttcaatg    4260
```

-continued

```
ttatcatcca ccctaatata acctaagagc caaaaggttt gggggatatt gtattttagg     4320
tctgtctttg catactactt attggtgttg tctttcatta agttggtaat ttgcacctac     4380
ttttggatag ttaagaatac taataatgta gatacttttt ttataaggta agatcttata     4440
aatgtgtcag catcaagaat atgctggtag gaacccaaat tgtctgattt aagatacccg     4500
aacttacgtt attgtattta gcagttttga gcatatggtc ctttctgaat ctgctcaatt     4560
tctggtaatt attggcagag ttttaaacct tttctcctat ccaacaggtt gaaaccagga     4620
caattgcaga agtacgagag gttctggact atgcatctca aacaaagact tcgttgacta     4680
ggataatgct ggacaatatg gttgttccat tatctaatgg agatattgat gtatccatgc     4740
ttaaggaggc tgtagatttg atcaatggga ggtttgagac agaggtactt ctggtttcat     4800
tttaaaattt tactgctcca caaactgtca gtatatacgc agcttagaaa tagcatttaa     4860
gatttgattt tatgataaaa actcctaact cataaaaaat ggtactgctt ggtttcccgt     4920
ttattatttt tgtcagtgga tatcttgtga tgacatgctt tgtttgctgt aatggtggca     4980
ggcttcagga aatgttaccc ttgaaacagt gcacaagatt ggacaaactg gtgttaccta     5040
catttctagg tatgtatttc gctcttgcta tttttttcaga agatcttcat taaaaaaatt     5100
ggaagataat aaaaatagaa gagacttctt ggtttgtgtt atttgtgttg ctgcgacgtc     5160 tttctttttcc tctttttttt tatactaata agatggttag tttactcgca cacatcagac     5220
aaaagctccc attagatagt ctatgttatg tataattttc ttgataaaat tgataaacag     5280
gagaacttgc atggattgct aaagtacaac aacaacaaca acaacaaaat acccagtgta     5340
atcccacaag tggagtctag ggaggatagt gtgtacgcat accttacccc caccttgaag     5400
gtagagaggc tgtttccgat agactctcgg ctcatgaaag acgagaagaa aagcaatagc     5460
accaagcaat aaccaacaag atagtaagag aacgaaacga aaggaacaat aagtaatact     5520
aaaaaaatct aacaaaaata gaatacggga ctaacactaa tactctcaac tacctactag     5580
tcgtatacct tgagtctcga cctccacacc ttcctatcaa ggatcatgtc cttggtaagc     5640
tgaactaatg tcatatcctg cctaatcacc tctccccaat acttcttcgg cctacctcta     5700
cctcttctca acccctccag ctccaacctc tcacacctcc ttacctggat tgctaaagta     5760
cttaaaatta ttaggttgtt gacctcttcg gttatttatt ggttaacaaa ggcttcacgt     5820
ttaagcacat gatttagtgt ggggtacaat ttcctcggct aggagtggac tcaatacttg     5880
agaaagttca atatatgttt gtttcatcca ggaatgatgc cctttatcag atattagcct     5940
gttattttga taaaaaacga atctatcttt tgtttagtcc atatgtatta ggcacataaa     6000
ggtttgttat gatactcata ctatgaaaaa tttaatgttt gcagtggtgc cctaacgcat     6060
tctgtgaaag cacttgacat atccctgaag atcgatacag agctcgccct tgaagttgga     6120
cgacgtacaa aacgagcatg accgccatta cttttgttgt agggttggag taaaagcagc     6180
tgaatggcac aaagtgcaaa taagaatcat tttactagtt gtcaaacaaa taagatgtaa     6240
gttgctggaa tatttcgatg gctttttttcc aacctaattg cttgagttgg tatttcatta     6300
tatctttgct ttcatgtttc atggaatttg acacaatgta aaaagttgat ttaaaagttt     6360
ggtgtatgtg aagttttgtg ttacttcaca tcttttatgg ctctcttcca acctaaattc     6420
agtcaaacct ctctctaaca gcctcttttg ttccgatatt ttttggttgc tatcgtgaag     6480
tgctgttata aaagacatat attataatat agcataaaaa tccgtttcga aaaaaatttg     6540
acttttatag tgaattgttg ttatataagg atgtatggag atatctgact gtagctctgt     6600
atatttt                                                               6607
```

-continued

```
<210> SEQ ID NO 3
<211> LENGTH: 5494
<212> TYPE: DNA
<213> ORGANISM: Nicotiana tabacum

<400> SEQUENCE: 3
aaaatccaac ggacaaaaaa atcggctgaa tttgatttgg ttccaacatt taaaaaagtt      60
tcagtgagaa agaatacggt gactgttgat gatataaaca aagggcacat tggtcaataa     120
ccataaaaaa ttatatgaca gctacagttg gtagcatgtg ctcagctatt gaacaaatct     180
aaagaaggta catctgtaac cggaacagca cttaaatgac taaattaccc tcatcagaaa     240
gcagatggag tgctacaaat aacacactat tcaacaacca taaataaaac gtgttcagct     300
actaaaacaa atataaataa atctatgttt gtaagcactc cagccatgtt aatggagtgc     360
tattgcctgt taactctcac ttataaaata gtagtagaaa aaatatgaac caaaacacaa     420
ccaaagaaag cattaagctc cccaaaaact attttccaca aaattcattt cacaacccccc    480 ccaaaaaaaa accatgttta gagctattcc tttcactgct acagtgcatc cttatgcaat     540
tacagctcca aggtctcttt aagaagaaaa aaagattctt gaaaatcatg ttttttttggt    600 tatattctga taaagattgg gttttttctg agtttgtgat taaattttgt gtgtaaaatt     660
gcaggttggt ggtgaaaatg tcagcaatag ccaccaagaa tacaagagtg gagtcattag     720
aggtgaaacc accagcacac ccaacttatg atttaaagga agttatgaaa cttgcactct     780
ctgaagatgc tgggaattta ggtttggtct tagcttatat cttttttctt tttaatctta     840
ttatattgtt aaatgggttg cactcaattt tattacttta gtaaatgctg taattaccta     900
atatgtggcc taactgtgta tatatttttt acccgttagt gcatagaact taagcaattt     960
atttaatttt ggagttgctt tatgaagttt agctatagtt ctttttgtta gtaagtgtta    1020
cctttagttt aaagaagggt gtgggtagag gcagatacac gatttgtgtt caacctttaa    1080
ggttcttagt attgaatcta tcatattttt gaagttacgg gttcagattc accatgtgtt    1140
gcaattttag tgaattttta cactaaaatt atgccccgtg tccaaactgg tactataacg    1200
ctacatatgc ctctgttggg tggattgtgg ggggggggg ggatagctct gtcaaaagtt     1260
atttttttgg tttctcgccc ggtgtccgtt gcctggtttg tggttcgacc aatccgtttg    1320
aggtaaagga acgactccat tctaatctga gacatatggt taaagataga gggtactaac    1380
caccccactt acaacctttg gtggtaaaag ttacattatt taagatcaat agttgtggat    1440
attgtcatgt actctatcag tttgtgcttg atgggaaact ttgtgtgatt aagtttcttg    1500
gaaatagcaa ttttttaagc acctggttac ctttgtgaat ttgagtactc aatttgaaaa    1560
agagatgtct atttattcaa tgttttcttg ggtgaaatgc aggagatgtg acttgtaagg    1620
cgacaattcc tcttgatatg gaatccgatg ctcattttct agcaaaggaa gacgggatca    1680
tagcaggaat tgcacttgct gagatgatat tcgcggaagt tgatccttca ttaaaggtat    1740
tgattttgct attaagttgt tccagtaacc ggcatatcta tttcgaaaaa gttttttgata   1800 aagggtaatt tttaatttct tcatgatctt attatcaggt ggagtggtat gtaaatgatg    1860
gcgataaagt tcataaaggc ttgaaatttg caaagtaca aggtaaacta aatgtgataa      1920
aatgatgact tgctaatgat ttttcagctt attaatcttt ccttgacttt tgtaggaaac    1980
gcttacaaca ttgttatagc tgagagggt gttctcaatt ttatgcaaag aatgagtgga     2040
atagctacac taactaaggt gtgtttctct tcatataaat agtttatcct taaaaaaaat    2100
```

-continued

```
atggaaagat attgccatga atggaaatgg ttagtgtcat tgatgagttg gtttcagtat    2160
ttcaagttaa gtgtaggtct gagactgctg aattgtttta tgtcgaagaa tactgagttt    2220
cgtgcagaac atatgtgttg ctccatattt agacattcct ctatgatata aaatagctat    2280
tgttgttcgt caggttgtgc aattggcttg ttaggtcatt gatccagctc aaagactgtt    2340
gaactaagag actttctccg tatttgcatt tcaatgtatt atggttgaaa aactaaagtc    2400
tccattcttc aatatttcga gtatgatagc ttctctgaga tgactatttg ccactgatgt    2460
tacttgcttg gcgtgtgagt gctattagta tgaccttatt tggattattt ttttcttctt    2520
cttaataacg gtggttcccg tttagtttgc gtgcgcctcg actattccac tgggtacatg    2580
ctgccttcca tcggcacagg tatcaggtaa ctctgttaat gaaggcttag ggataaaagg    2640
gcagcccggt gcactaagct ctcgctgtgc atggggtccg aggaagggcc ggaccacaag    2700
cttttgttgt cttttggaat ttgaatcctg gtatcccata gtttacaccc acttcattga    2760
ccgctaggtt gtcccttggg tgctaatgtt atttatattt tgaaacttct tgtttgtctt    2820
ttatgctgaa gatggtcctg aataggctag cattgtgggg atccaacttc ctgaattcat    2880
tgttttcata tttctatgag aagtagcctt gaccagaaag ataagagttc aagtcttgga    2940
aacaaatcgt gtgtattcgt tataaggcta tgcacatcca ctcttctgag accttagatg    3000
gtgccagagt aatatattga aaactatttt gcaatcagtc tatgagaaag actcctctgt    3060
ttaactaaat aattccattc cgagatgtca attagcttaa tttcttgcct ctatagtagt    3120
gattagaagg gactgagttt ttttttttat ttgcaggaaa tggcagatgc tgcacaccct    3180
gcttacatct tggagactag gaaaactgct cctggattac gtttggtgga taaatgggcg    3240
gtaaatattt actcaccaaa atcatctact tgtcaaggct atcacatgta tagtttatct    3300
tggctgactt tctacctggc tttaattaaa ggtattgatc ggtgggggga agaatcacag    3360
aatgggctta tttgatatgg taatgataaa agacaatcac atatctgctg ctggaggtgt    3420
cggcaaagct ctaaaatctg tggatcagta tttggagcaa aataaacttc aaataggggt    3480
tgaggttggc ctcatatacc tttgaattaa attcttcgat atggttttag atttgtgtcc    3540
ttatctttta attttatcgt ttgcacattt gatatgttta tttggacctg acagttcaat    3600
tacctattct accatccgtt acgctatact tttttgtcag ttttggtcag ataaacatct    3660
ttctagagcc attccaatca taaactattt atattttttga agatataaac tttatggctg    3720
atgctacttc caatatcctt tcactgaaga actaaattat tttctgttga aaacaaatgt    3780
tagtccaaga aagagatgtt tgacctatat gtgtctttca ttaagttggt attcgctcct    3840
actttggata gttaagaaga ctatagataa aatttgacaa ggtaaaattt aataaatgtg    3900
tcagcatcaa gaatatgctg gtaggaaccc aaattgtctg atttgcgatc cacgaagtta    3960
cgcaattgta tttggcagta gagctgtggt cctttcataa tgtattctat ttgtggtatt    4020
gaacagagtt ttaaaccttt tctcctatcc aacaggttga aaccaggaca attgaagaag    4080
tacgtgaggt tctagactat gcatctcaaa caaagacttc gttgactagg ataatgctgg    4140
acaatatggt tgttccatta tctaacggag atattgatgt atccatgctt aaggaggctg    4200
tagaattgat caatgggagg tttgatacgg aggtaacgcc tggtttcatt ttcattaact    4260
atttcacacg tgtcaactat gttgctcgga ctcttcaaat atgtagcagg atgcgtgtca    4320
aatcctccaa aagtagtgca ttttttggagg atctgacagg ggtgcggcat cattttaaga    4380
gaatctgcgc aacatagagt gtcagaatat ggaagactta ctgagatgca atgccttgat    4440
ttttcataaa aatgaagtaa cgcctggatt tcctgtaatc gtatatcttt tggtgacatg    4500
```

```
ctgttgttgt tgtaatggtg gcaggcttca ggaaatgtta cccttgaaac agtacacaag    4560
attggacaaa ctggtgttac ctacatttct aggtatgcat ttcgctcttg ctattttttt    4620
ccaaagatat ccatacaaga cagcagaaga cacatatata agagatttct cagtgtttgt    4680
tattagtata gctgggatgc ctttctgttt cttttctttt ccttcttata ataagatggt    4740
tagtatactt gccttgttca gacaaacgaa aaagatggtt actttacttg cgcatgttag    4800
accaaaaatg gtctcagtag atagtctatg ttatgtaaca attcttttga taggcaaaag    4860
tgacaggttt ttatccttag tattaggtgc gcgaaggttt gttatgatac taaaaataga    4920
gtttaaatct ttgcagtggt gccctgacgc attccgtgaa agcacttgac atttccctga    4980
agatcgatac agagctcgcc cttgaagttg gaaggcgtac aaaacgagca tgagcgccat    5040
tacttctgct ataggggttgg agtaaaagca gctgaatagc tgaaaggtgc aaataagaat    5100
cattttacta gttgtcaaac aaaagatcct tcactgtgta atcaaacaaa aagatgtaaa    5160
ttgctggaat atctcagatg gctctttttcc aaccttattg cttgagttgg taatttcatt    5220
atagctttgt tttcatgttt catggaattt gttacaatga aaatacttga tttataagtt    5280
tggtgtatgt aaaattctgt gttacttcaa atattttgag atgttgaata tcatgttctt    5340
aagctggatc agcaggatat agtcactaaa taatttctgt gtctgctcat ttacaaagat    5400
caatttatcc agctcattct tagggagtag taataaactg aagaattaac ccaaatagcc    5460
gcacacccaa catttaaact aaaaatagcc ggtg                               5494
```

```
<210> SEQ ID NO 4
<211> LENGTH: 4762
<212> TYPE: DNA
<213> ORGANISM: Nicotiana tabacum

<400> SEQUENCE: 4
tatggccaaa cggccccta attgatttat ttttctttta aggtgactat tgattatata      60
agcaaagggc acattggtca atagccataa aaatttatgt gacagctgta gttggggagc     120
atgtgctcag ttattaaaca aacaaatcta aagaaccctg tacacatgta atcagaacag     180
cacttaaatg actaaattac cctcatcagc aaagcagatg gagtgctaca aataatacat     240
tggtcaacaa ccaaaaataa aacgtgttca gctactaaaa caaatataaa gaaatctgtg     300
tttgtaagca ctccagccat gttaatggag tgctattgac agttaactca cttataaaat     360
agtagtagaa aaaatatgga ccaaaaacac aaccaaagaa agcattaagc tcctcaaaaa     420
ctattttcca caaaaatcat ttcacagccc caagaaaata aaccatgttt agggctcttc     480
ctttcactgc aacagtgcat ccatatgcaa ttacagctcc aaggtctctt taagaagaaa     540
aaaagattct tgaaaatcat gttttttttgg ttatattctg ataaagattg gatttttatg     600
agtttctgat tgaattttgt gtgtaaaatt gcaggttggt ggtgaaaatg tcagcaatag     660
ccaccaagaa tacaagagtg gagtcattag aggtgaagcc accagcacac ccaacttatg     720
atttaaaggg tgttatgcaa cttgcactct ctgaagatgc tgggaattta ggtctggtct     780
tagcctatat ttttttatttt atcttattat attgtcaaat gggttgcact caattttatt     840
attttagtaa atgatgtaat tacctaatat gtggcctaat tgtgtatata tatattttac     900
actgttagtg catagtaaca tataacttaa gctctttatt taatttgtag ttgctttatg     960
aagtttagct atagtatttt ttttttgggg ggcgggggag ctccaagctt caatttattt    1020
ttaattgtgt agcctcattt acttacagat aatgtgttct tagtaagtgt tacccttagt    1080
```

-continued

```
ttaaggaagg gggttggggg taggggcgga tccaggaggg tattgggggt agaggcagga   1140
gggtattggg ggtagaggcg gatccgcaaa tacccttagt tatttttatt ggtttctcgc   1200
cccatgtccg gtaattgctt tgtggtccga ctaatccgga ttgaggtaaa ggccgacttc   1260
attctcaggc ttgaacctga gacatttggt taaggatgga gggtactaac caccccactt   1320
acaacctttg gtggtaaaag tcgcattttt taagatccaa gagttgagga tgttgtcatg   1380
tactctatca gtttgtgctt gatgggaaac tttgcttaat taagtttctt ggaaatagca   1440
aatttttaag cacctagtta cctttgtgaa tttgagtact caatttgaaa aagatatatc   1500
tatttattca atgtttcctt gtgtggaatg caggagatgt gacttgtaag gcgacgattc   1560
ctgttgatat ggaatccgat gctcattttc tagcaaagga agacgggatc atagcaggga   1620
ttgcacttgc tgagatgata ttcgcggaag ttgatccttc actaaaggta ttgattttgc   1680
aattaagttg ttccagtaac cggcatatct atttcgaaga agttttttat acagggtaat   1740
ttttaaattg ttcatgttct tattatcagg tggagtggta tgtaaatgat ggtgataaag   1800
ttcataaagg cttgaaattt ggcaaagtac aaggtaaact aaatgtgata aaatgatgaa   1860
ttgctaatga ttttttcggct tattaatctt ccttgactt ttgtaggaaa cgcttacaac   1920
attgttatag ctgagagggt tgttctcaat tttatgcaaa gaatgagtgg aatagctaca   1980
ctaactaagg tgtgtttctc ttcatataaa tagctcatca ctaaaaaaaa tatggaaaga   2040
tattgccatg aatggaaatg gttagtgtca ttgacgagtt ggtttcagta tttcaagtta   2100
aatgtaggtc agagactgct gaattgttct atgtcgaaga atagaacaat caaatgatat   2160
ataatcaata aaatatgttg gtcatgaatg cggtaatgta tgacttaaaa tcttgtgatg   2220
gtacttctag tttaaccaat attcttactg atcaaatact tgaaccaata ctcaagcttc   2280
attatcaagc tcatagactg ttgaagtagg agactttgtc tgaatttgca attcaatgag   2340
aattagcctt aacctatggt aaaagttctc catctcacca gaaagtcaag agtgcaagtc   2400
ttggaaacaa atcctgtgta atcgttataa ggctgtgcac atccactctt ctgagacttt   2460
agatggtgcc agagccacat attgaaaacc attttgcaat caaacaacaa catacctagt   2520
aaaccaacaa tgaggtctgg ggagggtagc aagtacgcag gccttacccc taccctgtga   2580
aggtagagag actgtttcg atagaccta ttttgctctc agtctatgag aaaaactcct   2640
ctgtttaact agataattcc attccgagat gtcaatgagt ttaaattctt gcctctgtag   2700
tagtgattag aagagagtga gactgggttt ttctttatt tgcaggaaat ggcagatgct   2760
gcacaccctg cttacatctt ggagactagg aaaactgctc ctggattacg tttggtggat   2820
aaatgggcgg taaagattta ctcaccaaaa tcatttactt gtcaagtcca tcacatgtat   2880
agtttatctt ggctgacttt caacctggct ttaattaaag gtattgatcg gtggtgggaa   2940
gaatcacaga atgggcttat ttgatatggt aatgataaaa gacaatcaca tatctgctgc   3000
tggaggtgtc ggcaaagctc taaaatctgt ggatcagtat ttggagcaaa ataaacttca   3060
aataggggtt gaggttggcc tcatacccttt taattaaatt ctttgatatg tttataaatc   3120
tgagtcttta tcttttagtt ttattgtttg cacctttgat atgtttactt ggacctgaca   3180
gttcaattac ctattctacc aaccgttatg ctttactttt tttgtcattt ttggtcaaac   3240
atctttctag atatgtttga cctaaatatt tctgtctttc attaagttgg tatttgcacc   3300
tactttggat agttaagaat aattatgtag atactttttt ttgataagta aggtaaaatt   3360
ttataaatat gtcagcatca agaatatgct ggtaggaacc caaattgtct gatttgtgat   3420
ttccgaagtt acgatattgt atttggcagt agagatgtgg tcctttcaga gtgtgctcaa   3480
```

-continued

```
ttttgtggta attattgaac agaggtttaa acgtttttct cctatccaac aggttgaaac      3540
caggacaatt gcagaagtac gtgaggttct agaatatgca tctcaaacaa agacttcgtt      3600
gactaggata atgctggaca atatggttgt tccattatct aacggagata ttgatgtatc      3660
catgcttaag gaggctgtag aattgatcaa tgggaggttt gatacggagg taacgcctgg      3720
tttcatttgc attgtctgct tcacataagt gtcagaatat agaagaactg tgatgcaatg      3780
ccttgatttt tcataaaaaa gaagtaccgc atggatttcc tgtaaacgta tatcttttgg      3840
tgacatgctg ttgttgttgt aatggtgggg caggcttcag gaaatgttac ccttgaaaca      3900
gtacacaaga ttggacaaac tggtgttacc tacatttcta ggtatgcatt tcgctcttgc      3960
taatttactt caaaagatat ccatagaata cagcagaaga catatagaag agatttctca      4020
gtgtttgtta ctattagtat agctgggacg tctttctgtt cctttttgttt tccttcatat     4080 aataagatgg ttagtttaac ttgccttgtt cagaaaaacg aaaaagatga ttagtttact      4140
tgcacacaat agaccagaaa cggtctcagt agatagtcta tgttatgtta ataattcatt      4200
tgataggcaa aagtgacagg tttttatcct tagtattagg cgcgcgaagg tttgttatga      4260
tactaaaaat atagagttta aatctttgca gtggtgccct gacgcattct gtgaaagcac      4320
ttgacatttc cctgaagatt gatacagagc tcgcccttga agttggaagg cgtacaaaac      4380
gagcatgagc gccattactt ctgctatagg gttggagtaa aagcagctga atcgctgaaa      4440
gttcaaataa gaatcatttt actaatgtca aacaaaaaag atcgatcttt cactgtgtaa      4500
tcaaacaaaa agatgtaaat tgctggaata tctcagatgg ctcttttcca accttattgc      4560
ttgaattggt atttcaatat agctttgttt tcatgtttca tggaatttgt tacaatgaaa      4620
atacttgatt tacaagtttg gtgtatctga agctctgtgt tacttcaaat cttttgagat      4680
gttgaatatg ttcttaagct ggatcagcag gatatagtca ccaagtaatc tgtctaacat      4740
acaaagatca atttgtccac tt                                              4762
```

<210> SEQ ID NO 5
<211> LENGTH: 1053
<212> TYPE: DNA
<213> ORGANISM: Nicotiana tabacum

<400> SEQUENCE: 5

```
atgtttaaag ttcttccttt cactgcaata gtccacccta atgcaattac agctccaaga        60
ttggttgtga aaatgtcagc aatagccacc aaaaatgcag tggagtcatt tgtagtgaag       120
ccaccagcac acccaactta tgatttaaag ggtgttattc aacttgccct ctctgaagat       180
gctggggata taggagatgt gacttgtaag gcgacaattc ctattgacat ggaatccgaa       240
gctcattttc tagcaaagga agacgggatt gtagcaggaa ttgcacttgc tgagatgata       300
ttcgcagagg ttgatccttc actaaagatg gagtggtcta aaatgatgg cgataaagtt        360 cataaaggct tgaaattcgg caaagtacaa ggaaaggctc acagcattgt tatagctgag       420
agagttgttc tcaattttat gcaaaggatg agcggaattg ctacactaac taaggcgatg       480
gcagatgctg ctcaccctgc taccatcttg gagactagga aaactgctcc aggattacgt       540
ttggtggata aatgggcggt attaatcggt gggggggaaga atcacagaat gggcttattt       600
gatatggtaa tgataaaaga taatcacata tctgctgctg gaggtgtcag caaagctcta       660
aattccgtgg atcagtattt ggaacaaaat aaacttcaga tgggggttga ggttgaaacc       720
aggacaattg cagaagtaca tgaggttcta gaatatgcat ctcaaacaaa gacttcgttg       780
```

-continued

```
actaggataa tgcttgataa tatggttgtt ccattatcta acggagatat tgaggtatcc      840
atgcttgagg aggctgtaga tttgatcaat gggaggtttg agacagaggc ttcaggaaat      900
gttacccttg aaacagtgca caagattgga caaactggtg ttacctacat ttctagtggt      960
gcactaacgc attctgtgaa agcacttgac atttccctga agatcgatac agagctcgcc     1020
cttgaagtcg gacgacgtac aaaacgagca tga                                  1053

<210> SEQ ID NO 6
<211> LENGTH: 1053
<212> TYPE: DNA
<213> ORGANISM: Nicotiana tabacum

<400> SEQUENCE: 6
atgtttaaag tttttccttt cactgcaata gtgcaccctc atgcaattac agcaccaagg       60
ttggttgtga aaatgtcagc aatagccacc aaaaatgcag tggagtcatt agtagtgaag      120
ccaccagcac acccaactta tgatttaaag ggtgttattc aacttgccct ctctgaagat      180
gctggggatt taggagatgt gacttgtaag gcaacaattc ctattgacat ggaatccgaa      240
gctcattttc tagcaaagga agacgggatt gtagcaggaa ttgcacttgc tgagatgata      300
ttcgcagagg ttgatccttc actaaagatg gagtggtcta taaatgatgg tgataaagtt      360
cataaaggct tgaaattcgg caaagtacaa ggaaaggctc acagcattgt tatagctgag      420
agagttgttc tcaatttcat gcaaagaatg agcggaatag ctacactaac taaggcgatg      480
gcagatgctg cacaccctgc taccatcttg gagactagga aaactgctcc aggattacgt      540
ttggtggata atgggcggt attgatcggt gggggaaga atcacagaat gggcttattt       600
gatatggtaa tgataaaaga taatcacata tctgctgctg gaggtgtcag caaagctcta      660
aattccgtgg atcagtattt ggaacaaaat aaactccaga tggggggttga ggttgaaacc      720 aggacaattg cagaagtacg agaggttctg gactatgcat ctcaaacaaa gacttcgttg      780
actaggataa tgctggacaa tatggttgtt ccattatcta atggagatat tgatgtatcc      840
atgcttaagg aggctgtaga tttgatcaat gggaggtttg agacagaggc ttcaggaaat      900
gttacccttg aaacagtgca caagattgga caaactggtg ttacctacat ttctagtggt      960
gccctaacgc attctgtgaa agcacttgac atatccctga agatcgatac agagctcgcc     1020
cttgaagttg gacgacgtac aaaacgagca tga                                  1053

<210> SEQ ID NO 7
<211> LENGTH: 754
<212> TYPE: DNA
<213> ORGANISM: Nicotiana tabacum

<400> SEQUENCE: 7
atgtttagag ctattccttt cactgctaca gtgcatcctt atgcaattac agctccaagg       60
ttggtggtga aaatgtcagc aatagccacc aagaatacaa gagtggagtc attagaggtg      120
aaaccaccag cacacccaac ttatgattta aaggaagtta tgaaacttgc actctctgaa      180
gatgctggga atttaggaga tgtgacttgt aaggcgacaa ttcctcttga tatggaatcc      240
gatgctcatt ttctagcaaa ggaagacggg atcatagcag gaattgcact tgctgagatg      300
atattcgcgg aagttgatcc ttcattaaag gtggagtggt atgtaaatga tggcgataaa      360
gttcataaag gcttgaaatt tggcaaagta caaggaaacg cttacaacat tgttatagct      420
gagagggttg ttctcaattt tatgcaaaga atgagtggaa tagctacact aactaaggaa      480
atggcagatg ctgcacaccc tgcttacatc ttggagacta ggaaaactgc tcctggatta      540
```

-continued

```
cgtttggtgg ataaatgggc ggtattgatc ggtgggggga agaatcacag aatgggctta    600
tttgatatgg taatgataaa agacaatcac atatctgctg ctggaggtgt cggcaaagct    660
ctaaaatctg tggatcagta tttggagcaa aataaacttc aaataggggt tgaggttgaa    720
accaggacaa ttgaagaagt acgtgaggtt ctag                                754
```

```
<210> SEQ ID NO 8
<211> LENGTH: 754
<212> TYPE: DNA
<213> ORGANISM: Nicotiana tabacum

<400> SEQUENCE: 8
```

```
atgtttaggg ctcttccttt cactgcaaca gtgcatccat atgcaattac agctccaagg     60
ttggtggtga aatgtcagc aatagccacc aagaatacaa gagtggagtc attagaggtg    120
aagccaccag cacacccaac ttatgattta aagggtgtta tgcaacttgc actctctgaa    180
gatgctggga atttaggaga tgtgacttgt aaggcgacga ttcctgttga tatggaatcc    240
gatgctcatt ttctagcaaa ggaagacggg atcatagcag ggattgcact tgctgagatg    300
atattcgcgg aagttgatcc ttcactaaag gtggagtggt atgtaaatga tggtgataaa    360
gttcataaag gcttgaaatt tggcaaagta caaggaaacg cttacaacat tgttatagct    420
gagagggttg ttctcaattt tatgcaaaga atgagtggaa tagctacact aactaaggaa    480
atggcagatg ctgcacaccc tgcttacatc ttggagacta ggaaaactgc tcctggatta    540
cgtttggtgg ataaatgggc ggtattgatc ggtggtggga agaatcacag aatgggctta    600
tttgatatgg taatgataaa agacaatcac atatctgctg ctggaggtgt cggcaaagct    660
ctaaaatctg tggatcagta tttggagcaa aataaacttc aaataggggt tgaggttgaa    720
accaggacaa ttgcagaagt acgtgaggtt ctag                                754
```

```
<210> SEQ ID NO 9
<211> LENGTH: 350
<212> TYPE: PRT
<213> ORGANISM: Nicotiana tabacum

<400> SEQUENCE: 9
```

```
Met Phe Lys Val Leu Pro Phe Thr Ala Ile Val His Pro Asn Ala Ile
1               5                   10                  15

Thr Ala Pro Arg Leu Val Val Lys Met Ser Ala Ile Ala Thr Lys Asn
            20                  25                  30

Ala Val Glu Ser Phe Val Val Lys Pro Pro Ala His Pro Thr Tyr Asp
        35                  40                  45

Leu Lys Gly Val Ile Gln Leu Ala Leu Ser Glu Asp Ala Gly Asp Ile
    50                  55                  60

Gly Asp Val Thr Cys Lys Ala Thr Ile Pro Ile Asp Met Glu Ser Glu
65                  70                  75                  80

Ala His Phe Leu Ala Lys Glu Asp Gly Ile Val Ala Gly Ile Ala Leu
                85                  90                  95

Ala Glu Met Ile Phe Ala Glu Val Asp Pro Ser Leu Lys Met Glu Trp
            100                 105                 110

Ser Ile Asn Asp Gly Asp Lys Val His Lys Gly Leu Lys Phe Gly Lys
        115                 120                 125

Val Gln Gly Lys Ala His Ser Ile Val Ile Ala Glu Arg Val Val Leu
    130                 135                 140

Asn Phe Met Gln Arg Met Ser Gly Ile Ala Thr Leu Thr Lys Ala Met
```

```
145             150             155             160

Ala Asp Ala Ala His Pro Ala Thr Ile Leu Glu Thr Arg Lys Thr Ala
                165             170             175

Pro Gly Leu Arg Leu Val Asp Lys Trp Ala Val Leu Ile Gly Gly Gly
            180             185             190

Lys Asn His Arg Met Gly Leu Phe Asp Met Val Met Ile Lys Asp Asn
            195             200             205

His Ile Ser Ala Ala Gly Gly Val Ser Lys Ala Leu Asn Ser Val Asp
        210             215             220

Gln Tyr Leu Glu Gln Asn Lys Leu Gln Met Gly Val Glu Val Glu Thr
225             230             235             240

Arg Thr Ile Ala Glu Val His Glu Val Leu Glu Tyr Ala Ser Gln Thr
            245             250             255

Lys Thr Ser Leu Thr Arg Ile Met Leu Asp Asn Met Val Val Pro Leu
            260             265             270

Ser Asn Gly Asp Ile Glu Val Ser Met Leu Glu Glu Ala Val Asp Leu
            275             280             285

Ile Asn Gly Arg Phe Glu Thr Glu Ala Ser Gly Asn Val Thr Leu Glu
        290             295             300

Thr Val His Lys Ile Gly Gln Thr Gly Val Thr Tyr Ile Ser Ser Gly
305             310             315             320

Ala Leu Thr His Ser Val Lys Ala Leu Asp Ile Ser Leu Lys Ile Asp
            325             330             335

Thr Glu Leu Ala Leu Glu Val Gly Arg Arg Thr Lys Arg Ala
            340             345             350
```

<210> SEQ ID NO 10
<211> LENGTH: 350
<212> TYPE: PRT
<213> ORGANISM: Nicotiana tabacum

<400> SEQUENCE: 10

```
Met Phe Lys Val Phe Pro Phe Thr Ala Ile Val His Pro His Ala Ile
1               5               10              15

Thr Ala Pro Arg Leu Val Val Lys Met Ser Ala Ile Ala Thr Lys Asn
            20              25              30

Ala Val Glu Ser Leu Val Val Lys Pro Pro Ala His Pro Thr Tyr Asp
        35              40              45

Leu Lys Gly Val Ile Gln Leu Ala Leu Ser Glu Asp Ala Gly Asp Leu
    50              55              60

Gly Asp Val Thr Cys Lys Ala Thr Ile Pro Ile Asp Met Glu Ser Glu
65              70              75              80

Ala His Phe Leu Ala Lys Glu Asp Gly Ile Val Ala Gly Ile Ala Leu
            85              90              95

Ala Glu Met Ile Phe Ala Glu Val Asp Pro Ser Leu Lys Met Glu Trp
            100             105             110

Ser Ile Asn Asp Gly Asp Lys Val His Lys Gly Leu Lys Phe Gly Lys
        115             120             125

Val Gln Gly Lys Ala His Ser Ile Val Ile Ala Glu Arg Val Val Leu
    130             135             140

Asn Phe Met Gln Arg Met Ser Gly Ile Ala Thr Leu Thr Lys Ala Met
145             150             155             160

Ala Asp Ala Ala His Pro Ala Thr Ile Leu Glu Thr Arg Lys Thr Ala
                165             170             175
```

-continued

```
Pro Gly Leu Arg Leu Val Asp Lys Trp Ala Val Leu Ile Gly Gly Gly
            180                 185                 190

Lys Asn His Arg Met Gly Leu Phe Asp Met Val Met Ile Lys Asp Asn
        195                 200                 205

His Ile Ser Ala Ala Gly Gly Val Ser Lys Ala Leu Asn Ser Val Asp
    210                 215                 220

Gln Tyr Leu Glu Gln Asn Lys Leu Gln Met Gly Val Glu Val Glu Thr
225                 230                 235                 240

Arg Thr Ile Ala Glu Val Arg Glu Val Leu Asp Tyr Ala Ser Gln Thr
                245                 250                 255

Lys Thr Ser Leu Thr Arg Ile Met Leu Asp Asn Met Val Val Pro Leu
            260                 265                 270

Ser Asn Gly Asp Ile Asp Val Ser Met Leu Lys Glu Ala Val Asp Leu
        275                 280                 285

Ile Asn Gly Arg Phe Glu Thr Glu Ala Ser Gly Asn Val Thr Leu Glu
    290                 295                 300

Thr Val His Lys Ile Gly Gln Thr Gly Val Thr Tyr Ile Ser Ser Gly
305                 310                 315                 320

Ala Leu Thr His Ser Val Lys Ala Leu Asp Ile Ser Leu Lys Ile Asp
                325                 330                 335

Thr Glu Leu Ala Leu Glu Val Gly Arg Arg Thr Lys Arg Ala
            340                 345                 350

<210> SEQ ID NO 11
<211> LENGTH: 351
<212> TYPE: PRT
<213> ORGANISM: Nicotiana tabacum

<400> SEQUENCE: 11

Met Phe Arg Ala Ile Pro Phe Thr Ala Thr Val His Pro Tyr Ala Ile
1               5                   10                  15

Thr Ala Pro Arg Leu Val Val Lys Met Ser Ala Ile Ala Thr Lys Asn
            20                  25                  30

Thr Arg Val Glu Ser Leu Glu Val Lys Pro Pro Ala His Pro Thr Tyr
        35                  40                  45

Asp Leu Lys Glu Val Met Lys Leu Ala Leu Ser Glu Asp Ala Gly Asn
    50                  55                  60

Leu Gly Asp Val Thr Cys Lys Ala Thr Ile Pro Leu Asp Met Glu Ser
65                  70                  75                  80

Asp Ala His Phe Leu Ala Lys Glu Asp Gly Ile Ile Ala Gly Ile Ala
                85                  90                  95

Leu Ala Glu Met Ile Phe Ala Glu Val Asp Pro Ser Leu Lys Val Glu
            100                 105                 110

Trp Tyr Val Asn Asp Gly Asp Lys Val His Lys Gly Leu Lys Phe Gly
            115                 120                 125

Lys Val Gln Gly Asn Ala Tyr Asn Ile Val Ile Ala Glu Arg Val Val
        130                 135                 140

Leu Asn Phe Met Gln Arg Met Ser Gly Ile Ala Thr Leu Thr Lys Glu
145                 150                 155                 160

Met Ala Asp Ala Ala His Pro Ala Tyr Ile Leu Glu Thr Arg Lys Thr
                165                 170                 175

Ala Pro Gly Leu Arg Leu Val Asp Lys Trp Ala Val Leu Ile Gly Gly
            180                 185                 190

Gly Lys Asn His Arg Met Gly Leu Phe Asp Met Val Met Ile Lys Asp
            195                 200                 205
```

-continued

```
Asn His Ile Ser Ala Ala Gly Gly Val Gly Lys Ala Leu Lys Ser Val
    210                 215                 220

Asp Gln Tyr Leu Glu Gln Asn Lys Leu Gln Ile Gly Val Glu Val Glu
225                 230                 235                 240

Thr Arg Thr Ile Glu Glu Val Arg Glu Val Leu Asp Tyr Ala Ser Gln
                245                 250                 255

Thr Lys Thr Ser Leu Thr Arg Ile Met Leu Asp Asn Met Val Val Pro
                260                 265                 270

Leu Ser Asn Gly Asp Ile Asp Val Ser Met Leu Lys Glu Ala Val Glu
                275                 280                 285

Leu Ile Asn Gly Arg Phe Asp Thr Glu Ala Ser Gly Asn Val Thr Leu
    290                 295                 300

Glu Thr Val His Lys Ile Gly Gln Thr Gly Val Thr Tyr Ile Ser Ser
305                 310                 315                 320

Gly Ala Leu Thr His Ser Val Lys Ala Leu Asp Ile Ser Leu Lys Ile
                325                 330                 335

Asp Thr Glu Leu Ala Leu Glu Val Gly Arg Arg Thr Lys Arg Ala
                340                 345                 350

<210> SEQ ID NO 12
<211> LENGTH: 351
<212> TYPE: PRT
<213> ORGANISM: Nicotiana tabacum

<400> SEQUENCE: 12

Met Phe Arg Ala Leu Pro Phe Thr Ala Thr Val His Pro Tyr Ala Ile
1               5                   10                  15

Thr Ala Pro Arg Leu Val Val Lys Met Ser Ala Ile Ala Thr Lys Asn
                20                  25                  30

Thr Arg Val Glu Ser Leu Glu Val Lys Pro Pro Ala His Pro Thr Tyr
            35                  40                  45

Asp Leu Lys Gly Val Met Gln Leu Ala Leu Ser Glu Asp Ala Gly Asn
    50                  55                  60

Leu Gly Asp Val Thr Cys Lys Ala Thr Ile Pro Val Asp Met Glu Ser
65                  70                  75                  80

Asp Ala His Phe Leu Ala Lys Glu Asp Gly Ile Ile Ala Gly Ile Ala
                85                  90                  95

Leu Ala Glu Met Ile Phe Ala Glu Val Asp Pro Ser Leu Lys Val Glu
                100                 105                 110

Trp Tyr Val Asn Asp Gly Asp Lys Val His Lys Gly Leu Lys Phe Gly
            115                 120                 125

Lys Val Gln Gly Asn Ala Tyr Asn Ile Val Ile Ala Glu Arg Val Val
    130                 135                 140

Leu Asn Phe Met Gln Arg Met Ser Gly Ile Ala Thr Leu Thr Lys Glu
145                 150                 155                 160

Met Ala Asp Ala Ala His Pro Ala Tyr Ile Leu Glu Thr Arg Lys Thr
                165                 170                 175

Ala Pro Gly Leu Arg Leu Val Asp Lys Trp Ala Val Leu Ile Gly Gly
                180                 185                 190

Gly Lys Asn His Arg Met Gly Leu Phe Asp Met Val Met Ile Lys Asp
            195                 200                 205

Asn His Ile Ser Ala Ala Gly Gly Val Gly Lys Ala Leu Lys Ser Val
    210                 215                 220

Asp Gln Tyr Leu Glu Gln Asn Lys Leu Gln Ile Gly Val Glu Val Glu
```

```
225                 230                 235                 240

Thr Arg Thr Ile Ala Glu Val Arg Glu Val Leu Glu Tyr Ala Ser Gln
                245                 250                 255

Thr Lys Thr Ser Leu Thr Arg Ile Met Leu Asp Asn Met Val Val Pro
                260                 265                 270

Leu Ser Asn Gly Asp Ile Asp Val Ser Met Leu Lys Glu Ala Val Glu
                275                 280                 285

Leu Ile Asn Gly Arg Phe Asp Thr Glu Ala Ser Gly Asn Val Thr Leu
                290                 295                 300

Glu Thr Val His Lys Ile Gly Gln Thr Gly Val Thr Tyr Ile Ser Ser
305                 310                 315                 320

Gly Ala Leu Thr His Ser Val Lys Ala Leu Asp Ile Ser Leu Lys Ile
                325                 330                 335

Asp Thr Glu Leu Ala Leu Glu Val Gly Arg Arg Thr Lys Arg Ala
                340                 345                 350

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tagcaaagga agacgggatc atag                                           24

<210> SEQ ID NO 14
<211> LENGTH: 11
<212> TYPE: DNA
<213> ORGANISM: Nicotiana tabacum

<400> SEQUENCE: 14
acgggatcat a                                                         11

<210> SEQ ID NO 15
<211> LENGTH: 20
<212> TYPE: DNA
<213> ORGANISM: Nicotiana tabacum

<400> SEQUENCE: 15
ggatcatagc agggattgca                                                20

<210> SEQ ID NO 16
<211> LENGTH: 20
<212> TYPE: DNA
<213> ORGANISM: Nicotiana tabacum

<400> SEQUENCE: 16
ggatcatagc agggattgca                                                20

<210> SEQ ID NO 17
<211> LENGTH: 11
<212> TYPE: DNA
<213> ORGANISM: Nicotiana tabacum

<400> SEQUENCE: 17
acgggatcat a                                                         11

<210> SEQ ID NO 18
<211> LENGTH: 11
```

-continued

```
<212> TYPE: DNA
<213> ORGANISM: Nicotiana tabacum

<400> SEQUENCE: 18
agacgggatc a                                                                11

<210> SEQ ID NO 19
<211> LENGTH: 10
<212> TYPE: DNA
<213> ORGANISM: Nicotiana tabacum

<400> SEQUENCE: 19
acgggatcat                                                                  10
```